(12) United States Patent
Sasaki et al.

(10) Patent No.: US 6,448,386 B2
(45) Date of Patent: *Sep. 10, 2002

(54) HIGH MOLECULAR WEIGHT MAJOR OUTER MEMBRANE PROTEIN OF MORAXELLA

(75) Inventors: Ken Sasaki; Robin E. Harkness, both of Willowdale; Sheena M. Loosmore, Aurora; Pele Chong, Richmond Hill; Michel H. Klein, Willowdale, all of (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 08/945,567
(22) PCT Filed: Apr. 29, 1996
(86) PCT No.: PCT/CA96/00264
§ 371 (c)(1), (2), (4) Date: Mar. 19, 1998
(87) PCT Pub. No.: WO96/34960
PCT Pub. Date: Nov. 7, 1996

Related U.S. Application Data

(63) Continuation-in-part of application No. 08/621,944, filed on Mar. 20, 1996, which is a continuation-in-part of application No. 08/478,370, filed on Jun. 7, 1995, now Pat. No. 5,808,024, which is a continuation-in-part of application No. 08/431,718, filed on May 1, 1995, now Pat. No. 6,335,018.

(51) Int. Cl.[7] .................. C07H 21/02; C07H 21/04; C12N 1/20; C12N 15/00
(52) U.S. Cl. .................. 536/23.1; 536/23.5; 435/252.3; 435/320.1; 435/325; 435/69.7; 530/300
(58) Field of Search .................. 536/23.1, 23.5; 435/252.3, 320.1, 325, 69.7; 530/300

(56) References Cited

U.S. PATENT DOCUMENTS

| | | | |
|---|---|---|---|
| 4,258,029 A | | 3/1981 | Moloney et al. ............... 424/49 |
| 4,855,283 A | | 8/1989 | Lockhoff et al. ............... 514/8 |
| 5,292,869 A | * | 3/1994 | Schryvers |
| 5,552,146 A | * | 9/1996 | Hansen et al. |
| 5,599,693 A | * | 2/1997 | Hansen et al. |
| 5,607,846 A | * | 3/1997 | Murphy et al. |
| 5,759,813 A | * | 6/1998 | Hansen et al. |
| 5,766,607 A | * | 6/1998 | Fenwick et al. |
| 5,808,024 A | * | 9/1998 | Sasaki et al. |
| 5,981,213 A | * | 11/1999 | Hansen et al. |
| 5,993,826 A | * | 11/1999 | Hansen et al. |
| 6,214,981 B1 | * | 4/2001 | Tucker et al. |
| 6,335,018 B1 | * | 1/2002 | Sasaki et al. ............ 424/184.1 |

FOREIGN PATENT DOCUMENTS

| | | | |
|---|---|---|---|
| WO | WO A 93 03761 | | 3/1883 |
| WO | WO A 91 09952 | | 7/1991 |
| WO | 91/16072 | | 10/1991 |
| WO | 93 03761 | * | 3/1993 |
| WO | WO A 93 10214 | | 5/1993 |
| WO | 96/34960 | * | 11/1996 |
| WO | 01/07619 | * | 2/2001 |

OTHER PUBLICATIONS

Van Hare, G.F., P.A. Shurin, C.D. Marchant, N.A. Cartelli, C.E.Johnson, D. Fulton, S. Carlin, and C.H. Kim. Acute otitis media caused by *Branhamella catarrhalis*: biology and therapy. Rev. Infect. Dis. 9:16–27.

Chapman, A.J., D.M. Musher, S. Jonsson, J.E. Clarridge, and R.J. Wallace. 1985. Development of bactericidal antibody during *Branhamella catarrhalis* infection. J. Infect. Dis. 151:878–882.

Hager, H., A. Verghese, S. Alvarez, and S.L. Berk. 1987. *Branhamella catarrhalis* respiratory infections. Rev. Infect. Dis. 9:1140–1149.

McLeod, D.T., F. Ahmad, M.J. Croughan, and M.A. Calder. 1986. Bronchopulmonary Infection due to *M. catarrhalis*. Clinical features and therapeutic response. Drugs 31(Suppl.3):109–112.

Nicotra, B., M. Rivera, J.I. Luman, and R.J. Wallace. 1986. *Branhamella catarrhalis* as a lower respiratory tract pathogen in patients with chronic lung disease. Arch.Intern.Med. 146:890–893.

Ninane, G., J. Joly, and M. Kraytman. 1978. Bronchopulmonary infection due to *Branhamella catarrhalis* 11 cases assessed by transtracheal puncture. Br.Med.Jr. 1:276–278.

Srinivasan, G., M.J. Raff, W.C. Templeton, S.J. Givens, R.C. Graves, and J.C. Mel. 1981. *Branhamella catarrhalis* pneumonia. Report of two cases and review of the literature. Am.Rev. Respir. Dis. 123:553–555.

West, M., S.L. Berk, and J.K. Smith. 1982. *Branhamella catarrhalis* pneumonia. South.Med. J. 75:1021–1023.

Brorson, J–E., A. Axelsson, and S.E. Holm. 1976. Studies on *Branhamella catarrhalis* (*Nelsseria catarrhalls*) with special reference to maxillary sinusitis. Scan. J. Infect. Dis. 8:151–155.

Evans, F.O., Jr., J.B. Sydnor, W.E.C. Moore, G.R. Moore, J.L. Manwaring, A.H. Brill, R.T. Jackson, S. Hanna, J.S. Skaar, L.V. Holdeman, G.S. Fitz–Hugh, M.A. Sande, and J.M. Gwaltney, Jr. 1975. Sinusitis of the maxillary antrum. N.Engl.J.Med. 293:735–739.

Tinkelman, D.G., and H.J. Silk. 1989. Clinical and bacteriologic features of chronic sinusitis in children. Am.J.Dis. .Child. 143:938–942.

(List continued on next page.)

*Primary Examiner*—Nita Minnifield
(74) *Attorney, Agent, or Firm*—Sim & McBurney

(57) ABSTRACT

An isolated and purified outer membrane protein of a Moraxella strain, particularly *M. catarrhalis*, having a molecular mass of about 200 kDa, is provided. The about 200 kDa outer membrane protein as well as nucleic acid molecules encoding the same are useful in diagnostic applications and immunogenic compositions, particularly for in vivo administration to a host to confer protection against disease caused by a bacterial pathogen that produces the about 200 kDa outer membrane protein or produces a protein capable of inducing antibodies in a host specifically reactive with the about 200 kDa outer membrane protein.

10 Claims, 28 Drawing Sheets

OTHER PUBLICATIONS

Wald, E.R., C. Byers, N. Guerra, M. Casselbrant, and D. Beste. 1989. Subacute sinusitis in children. J.Pediatr. 115:28–32.

Wald, E.R., G.J. Milmoe, A. Bowen, J.Ledesma–Medina, N. Salamon, and C.D.Bluestone. 1981. Acute maxillary sinusitis in children. N. Engl.J.Med. 304:749–754.

Christensen, J.J., and B. Bruun. 1985. Bacteremia caused by a beta–lactamase producing strain of *Branhamella catarrhalis*. Acta.Pathol. Microbiol. Immunol. Scand. Sect.B 93:273–275.

Craig, D.B., and P.A. Wehrle. 1983. *Branhamella catarrhalis* septic arthritis. J. Rheumatol. 10:985–986.

Gray, L.D., R.E. Van Scoy, J.P. Anhalt, and P.K.W. Yu. 1989. Wound infection caused by *Branhamella catarrhalis*. J.Clin. Microbiol. 27:818–820.

Guthrie, R., K. Bakenhaster, R.Nelson, and R. Woskobnick. 1988. *Branhamella catarrhalis* sepsis: a case report and review of the literature. J.Infect.Dis. 158:907–908.

Hiroshi, S., E.J. Analssle, N. Khardori, and G.P. Bodey. 1988. *Branhamella catarrhalis* septicemia in patients with leukemia. Cancer 61:2315–2317.

O'Neill, J.H., and P.W. Mathieson. 1987. Meningitis due to *Branhamella catarrhalis*. Aust. N.Z. J. Med. 17:241–242.

Murphy, T.F. 1989. The surface of *Branhamella catarrhalis*: a systematic approach to the surface antigens of an emerging pathogen. Pediatr. Infect. Dis. J. 8:S75–S77.

Klingman, K.L., and T.F. Murphy. 1994. Purification and characterization of a high–molecular–weight outer membrane protein of *Moraxella (Branhamella) catarrhalis*. Infect. Immun. 62:1150–1155.

Helminen, M.E., I. MacIver, J.L. Latimer, J. Klesney–Talt, L.D. Cope, M. Paris, G.H. McCracken, Jr., and E.J. Hansen. 1994. A large, antigenically conserved protein on the surface of *Moraxella catarrhalis* is a target for protective antibodies. J. Infect. Dis. 170:867–872.

Panezutti H., O. James, E.J. Hanson, Y. Choi, R.E. Harkness, M.H. Klein and P. Chong, 1993. Identification of surface–exposed B–cell epitopes recognized by *Haemophilus influenzae* type b P1 specific monoclonal antibodies. Infec. Immun. 61: 1867–1872.

Nixon–George et al. (1990), J. Immunology 144:4798–4802.

Wiesmuller (1989), Vaccine 8:29–33.

Deres et al. (1989), Nature 342:561.

Lockhoff, O. Glycolipids as Immmunomodulators: Synthesis and Properties. 1991. Chem. Int. Ed. Engl. 30:1611–1620.

Journal of Infectious Diseases, 158 (4). 1988. 761–765., XP002013102 Bartos L C et al: Comparison of the Outer Membrane Proteins of 50 Strains of Branhamella–Catarrhalis.

Science, Apr. 14, 199, 268 (5208) P221–5, United States, XP002013103 Casey P.J.: "Protein lipidation in cell signalling" see the whole document.

Ostle et al, 1986. AM. J. Vet. Res. 47(7):1419–1421.

Burgess et al. J. Cell Biology 111:2129–38.

Lazar et al. M. Cell Biology 8(3):1297–52.

Timothy F. Murphy et al., Microbiol. Path. 1989, 6: 159–174.

Aebi, C,. et al, "A Protective Epitope of Moraxella Catarrhalis is Encoded by Two Different Genes"—Inf. And Immun. Nov. 1997, pp. 4367–4377. vol. 65, No. 11.

Kyd, et al—J. Med. Microbiol—vol. 47 (1998), pp. 159–168.

\* cited by examiner

FIG.6A

Nuclectide Sequence Between SalI and NcoI

```
         10         20         30         40         50         60         70
CCATGGATAT GGGCAGGTGT GCTCGCCTGC CGTATGATGG CGATGACACC CCATTGCCCC CATATCTGTA
         80         90        100        110        120        130        140
CGATTTGACA TGTGATATGA TTTAACATGT GACATGATTT AACATTGTTT AATACTGTTG CCATCATTAC
        150        160        170        180        190        200        210
CATAATTTAG TAACGCATTT AGTAACGCAT TTGTAAAAAT CATTGCGCCC CTTTATGTGT ATCATATGAA
        220        230        240        250        260        270        280
TAGAATATTA TGATTGTATC TGATTATTGT ATCAGAATGG TGATGCTATA TGATGATGCC TACGAGTTGA
        290        300        310        320        330        340        350
TTTGGGTTAA TCACTCTATG ATTTGATATA TTTTGAAACT AATCTATTGA CTTAAATCAC CATATGGTTA
        360        370        380        390        400        410        420
TAATTTAGCA TAATGGTAGG CTTTTTGTAA AAATCACATC GCAATATTGT TCTACTGTTA CTACCATGCT
        430        440        450        460        470        480        490
TGAATGACGA TCCCAATCAC CAGATTCATT CAAGTGATGT GTTTGTATAC GCACCATTTA CCCTAATTAT
        500        510        520        530        540        550        560
TTCAATCAAA TGCCTATGTC AGCATGTATC ATTTTTTTAA GGTAAACCAC CATGAATCAC ATCTATAAAG
        570        580        590        600        610        620        630
TCATCTTTAA CAAAGCCACA GGCACATTTA TGGCAGTGGC AGAGTACGCC AAATCCCACA GCACGGGGGG
```

FIG.6B

| | | | | | | |
|---|---|---|---|---|---|---|
| 640 | 650 | 660 | 670 | 680 | 690 | 700 |
| GGGTAGCTG | TGCTACAGGG | CAAGTTGGCA | GTGTATGCAC | TCTGAGCTTT | GCCCGTATTG | CCGGCTCGC |
| 710 | 720 | 730 | 740 | 750 | 760 | 770 |
| TGTCCTCGTG | ATCGGTGCAA | CGCTCAGTGG | CAGTGCTTAT | GCTCAAAAAA | AAGATACCAA | ACATATCGCA |
| 780 | 790 | 800 | 810 | 820 | 830 | 840 |
| ATTGGTGAAC | AAAACCAGCC | AAGACGCTCA | GGCACTGCCA | AGGCGGACGG | TGATCGAGCC | ATTGCTATTG |
| 850 | 860 | 870 | 880 | 890 | 900 | 910 |
| GTGAAAATGC | TAACGCACAG | GGCGGTCAAG | CCATCGCCAT | AGGCGGACGG | AATAAAACTG | TCAATGGAAG |
| 920 | 930 | 940 | 950 | 960 | 970 | 980 |
| CAGTTTGGAT | AAGATAGGTA | CCGATGCTAC | GGGTCAAGAG | TCCATCGCCA | TCGGTGGTGA | TGTAAAGGCT |
| 990 | 1000 | 1010 | 1020 | 1030 | 1040 | 1050 |
| AGTGGTGATG | CCTCGATTGC | CATCGGTAGT | GATGACTTAC | ATTTGCTTGA | TCAGCATGGT | AATCCTAAAC |
| 1060 | 1070 | 1080 | 1090 | 1100 | 1110 | 1120 |
| ATCCGAAAGG | TACTCTGATT | AACGATCTTA | TTAACGGCCA | TGCAGTATTA | AAAGAAATAC | GAAGCTCAAA |
| 1130 | 1140 | 1150 | 1160 | 1170 | 1180 | 1190 |
| GGATAATGAT | GTAAAATATA | GACGCACAAC | CGCAAGCGGA | CACGCCAGTA | CTGCAGTGGG | AGCCATGTCA |
| 1200 | 1210 | 1220 | 1230 | 1240 | 1250 | 1260 |
| TATGCACAGG | GTCATTTTTC | CAACGCCTTT | GGTACACGGG | CAACAGCTAA | AAGTGCCTAT | TCCTTGGCAG |

FIG.6C

| 1270 TGGGTCTTGC | 1280 CGCCACAGCC | 1290 GAGGGCCAAT | 1300 CTACAATCGC | 1310 TATTGGTTCT | 1320 GATGCAACAT | 1330 CTAGCTCGTT |
|---|---|---|---|---|---|---|
| 1340 GGGAGCCGATA | 1350 GCCCTTGGTG | 1360 CAGGTACTCG | 1370 TGCTCAGCTA | 1380 CAGGGCAGTA | 1390 TTGCCCTAGG | 1400 TCAAGGTTCT |
| 1410 GTTGTCACTC | 1420 AGAGTGATAA | 1430 TAATTCTAGA | 1440 CCGGCCTATA | 1450 CACCAAATAC | 1460 CCAGGCACTA | 1470 GACCCCAAGT |
| 1480 TTCAAGCCAC | 1490 CAATAATACG | 1500 AAGGCGGGTC | 1510 CACTTTCCAT | 1520 TGGTAGTAAC | 1530 TCTATCAAAC | 1540 GTAAAATCAT |
| 1550 CAATGTCGGT | 1560 GCAGGTGTTA | 1570 ATAAAACCGA | 1580 TGCGGTCAAT | 1590 GTGGCACAGC | 1600 TAGAAGCGGT | 1610 GGTGAAGTGG |
| 1620 GCTAAGGAGC | 1630 GTAGAATTAC | 1640 TTTTCAGGGT | 1650 GATGATAACA | 1660 GTACTGACGT | 1670 AAAAATAGGT | 1680 TTGGATAATA |
| 1690 CTTTAACTAT | 1700 TAAAGGTGGT | 1710 GCAGAGACCA | 1720 ACGCATTAAC | 1730 CGATAATAAT | 1740 ATCGGTGTGG | 1750 TAAAAGAGGC |
| 1760 GGTCTGAAAG | 1770 TTAAACTTGC | 1780 TAAAACTTTA | 1790 AACAATCTTA | 1800 AACAATCTTA | 1810 CTGAGGTGAA | 1820 TACAACTACA |
| 1830 TTAAATGCCA | 1840 CAACCACAGT | 1850 TAAGGTAGGT | 1860 AGTAGTAGTA | 1870 GTACTACAGC | 1880 TGAATTATTG | 1890 AGTGATAGTT |

FIG.6D

```
1900       1910       1920       1930       1940       1950       1960
TAACCTTTAC CCAGCCCAAT ACAGGCAGTC AAAGCACAAG CAAAACCGTC TATGGCGTTA ATGGGGTGAA
1970       1980       1990       2000       2010       2020       2030
GTTTACTAAT AATGCAGAAA CAACAGCAGC AATCGGCACT ACTCGTATTA CCAGAGATAA AATTGGCTTT
2040       2050       2060       2070       2080       2090       2100
GCTCGAGATG GTGATGTTGA TGAAAAACAA GCACCATATT TGGATAAAAA ACAACTTAAA GTGGGTAGTG
2110       2120       2130       2140       2150       2160       2170
TTGCAATTAC CATAGACAAT GGCATTGATG CAGGTAATAA AAAGATCAGT AATCTTGCCA AAGGTAGCAG
2180       2190       2200       2210       2220       2230       2240
TGCTAACGAT GCGGTTACCA TCGAACAGCT CAAAGCCGCC AAGCCTACTT TAAACGCAGG CGCTGGCATC
2250       2260       2270       2280       2290       2300       2310
AGTGTCACAC CTACTGAAAT ATCAGTTGAT GCTAAGAGTG GCAATGTTAC CGCCCCAACT TACAACATTG
2320       2330       2340       2350       2360       2370       2380
GCGTGAAAAC CACCGAGCTT AACAGTGATG GCACTAGTGA TAAATTTAGT GTTAAGGGTA GTGGTACGAA
2390       2400       2410       2420       2430       2440       2450
CAATAGCTTA GTTACCGCCG AACATTGGC  AAGCTATCTA AATGAAGTCA ATCGAACGGC TGACAGTGCT
2460       2470       2480       2490       2500       2510       2520
CTACAAAGCT TTACCGTTAA AGAAGAAGAC GATGATGACG CCAACGCTAT CACCGTGGCT AAAGATACGA
```

FIG. 6E

```
2530       2540       2550       2560       2570       2580       2590
CAAAAAATGC CGGGCGCAGTC AGCATCTTAA AACTCAAAGG TAAAAACGGT CTAACGGTTG CTACCAAAAA 2600       2610       2620       2630       2640       2650       2660
AGATGGTACG GTTACCTTTG GGCTTAGCCA AGATAGCGGT CTGACCATTG GCAAAAGCAC CCTAAACAAC 2670       2680       2690       2700       2710       2720       2730
GATGGCTTGA CTGTTAAAGA TACCAACGAA CAAATCCAAG TCGGTGCTAA TGGCATTAAA TTTACTAATG 2740       2750       2760       2770       2780       2790       2800
TGAATGGTAG TAATCCAGGT ACTGGCATTG CAAATACCGC TCGCATTACC AGAGATAAAA TTGGCTTTGC 2810       2820       2830       2840       2850       2860       2870
TGGTTCTGAT GGTGCAGTTG ATACAAACAA ACCTTATCTT GATCAAGACA AGCTACAAGT TGGCAATGTT 2880       2890       2900       2910       2920       2930       2940
AAGATTACCA ACACTGGCAT TAACGCAGGT GGTAAAGCCA TCACAGGGCT GTCCCCAACA CTGCCTAGCA 2950       2960       2970       2980       2990       3000       3010
TTGCCGATCA AAGTAGCCGC AACATAGAAC TGGGCAATAC AATCCAAGAC AAAGACAAAT CCAACGCTGC 3020       3030       3040       3050       3060       3070       3080
CAGCATTAAT GATATATTAA ATACAGGCTT TAACCTAAAA AATAATAACA ACCCCATTGA CTTTGTCTCC 3090       3100       3110       3120       3130       3140       3150
ACTTATGACA TTGTTGACTT TGCCAATGGC AATGCCACCA CCGCCACAGT AACCCATGAT ACCGCTAACA
```

FIG.6F

```
3160       3170       3180       3190       3200       3210       3220
AAACCAGTAA AGTGGTATAT GATGTGAATG TGGATGATAC AACCATTCAT CTAACAGGCA CTGATGACAA
      3230       3240       3250       3260       3270       3280       3290
TAAAAAACTT GGCGTCAAAA CCACCAAACT GAACAAAACA AGTGCTAATG GTAATACAGC AACTAACTTT
      3300       3310       3320       3330       3340       3350       3360
AATGTTAACT CTAGTGATGA AGATGCCCTT GTTAACGCCA AAGACATCGC CGAAAATCTA AACACCCTAG
      3370       3380       3390       3400       3410       3420       3430
TGAAAATAAT AATGCTGATG AAATGCTGATG CAGACACCGC CCTACAAACC TTTACCGTTA AAAAGGTAGA
      3440       3450       3460       3470       3480       3490       3500
CCAAGGAAAT TCACACCACC AAAGGCACAG CAGACACCGC CATCACCGTG GGTCAAAAGA ACGCAAATAA TCAAGTCAAC
      3510       3520       3530       3540       3550       3560       3570
ACCCTAACAC TCAAAGGTGA AAACGGTCTT AATATTAAAA CCGACAAAAA TGGTACGGTT ACCTTTGGCA
      3580       3590       3600       3610       3620       3630       3640
TTAACACCAC AAGCGGTCTT AAAGCCGGCA AAAGCACCCT AAACGACGGT GGCTTGTCTA TTAAAACCC
      3650       3660       3670       3680       3690       3700       3710
CACTGGTAGC GAACAAATCC AAGTCGGTGC TGATGGCGTG AAGTTTGCCA AGGTTAATAA TAATGGTGTT
      3720       3730       3740       3750       3760       3770       3780
GTAGGTGCTG GCATTGATGG CACAACTCGC ATTACCAGAG ATGAAATTGG CTTTACTGGG ACTAATGGCT
```

FIG. 6G

```
3790       3800       3810       3820       3830       3840       3850
CACTTGATAA AAGCAAACCC CACCTAAGCA AAGACGGCAT TAACGCAGGT GGTAAAAAGA TTACCAACAT
3860       3870       3880       3890       3900       3910       3920
TCAATCAGGT GAGATTGCCC AAAACAGCCA TGATGCTGTG ACAGGCGGCA AGATTTATGA TTTAAAAACC
3930       3940       3950       3960       3970       3980       3990
GAACTTGAAA ACAAAATCAG CAGTACTGCC AAAACAGCAC AAAAACTCATT ACACGAATTC TCAGTAGCAG
4000       4010       4020       4030       4040       4050       4060
ATGAACAAGG TAATAACTTT ACGGTTAGTA ACCCTTACTC CAGTTATGAC ACCTCAAAGA CCTCTGATGT
4070       4080       4090       4100       4110       4120       4130
CATCACCTTT GCAGGTGAAA ACGGCATTAC CACCAAGGTA AATAAAGGTG TGGTGCGTGT GGGCATTGAC
4140       4150       4160       4170       4180       4190       4200
CAAACCAAAG GCTTAACCAC GCCTAAGCTG ACCGTGGGTA ATAATAATGG CAAAGGCATT GTCATTGACA
4210       4220       4230       4240       4250       4260       4270
GCCAAAATGG TCAAAATACC ATCACAGGAC TAAGCAACAC TCTAGCTAAT GTTACCAATG ATAAAGGTAG
4280       4290       4300       4310       4320       4330       4340
CGTACGCACC ACAGAACAGG GCAATATAAT CAAAGACGAA GACAAAACCC GTGCCGCCAG CATTGTTGAT
4350       4360       4370       4380       4390       4400       4410
GTGCTAAGCG CAGGCTTTAA CTTGCAAGGC AATGGTGAAG CGGTTGACTT TGTCTCCACT TATGACACCG
```

FIG.6H

```
4420        4430        4440        4450        4460        4470        4480
TCAACTTTGC  CGATGGCAAT  GCCACCACCG  CTAAGGTGAC  CTATGATGAC  ACAAGCAAAA  CCAGTAAAGT
4490        4500        4510        4520        4530        4540        4550
GGTCTATGAT  GTCAATGTGG  ATGATACAAC  CATTGAAGTT  AAAGATAAAA  AACTTGGCGT  AAAACCACC
4560        4570        4580        4590        4600        4610        4620
ACATTGACCA  GTACTGGCAC  AGGTGCTAAT  AAATTTGCCC  TAAGCAATCA  AGCTACTGGC  GATGCGCTTG
4630        4640        4650        4660        4670        4680        4690
TCAAGGCCAG  TGATATCGTT  GCTCATCTAA  ACACCTTATC  TGGCGACATC  CAAACTGCCA  AAGGGGCAAG
4700        4710        4720        4730        4740        4750        4760
CCAAGCGAAC  AACTCAGCAG  GCTATGTGGA  TGCTGATGGC  AATAAGGTCA  TCTATGACAG  TACCGATAAC
4770        4780        4790        4800        4810        4820        4830
AAGTACTATC  AAGCCAAAAA  TGATGGCACA  GTTGATAAAA  CCAAAGAAGT  TGCCAAAGAC  AAACTGGTCG
4840        4850        4860        4870        4880        4890        4900
CCCAAGCCCA  AACCCCAGAT  GGCACATTGG  CTCAAAATGAA TGTCAAATCA  GTCATTAACA  AAGAACAAGT
4910        4920        4930        4940        4950        4960        4970
AAATGATGCC  AATAAAAAGC  AAGGCATCAA  TGAAGACAAC  GCCTTTGTTA  AAGGACTTGA  AAAAGCCGCT
4980        4990        5000        5010        5020        5030        5040
TCTGATAACA  AAACCAAAAA  CGCCGCAGTA  ACTGTGGGTG  ATTTAAATGC  CGTTGCCCAA  ACACCGCTGA
```

FIG.6I

| | | | | | | |
|---|---|---|---|---|---|---|
| 5050 CCTTTGCAGG | 5060 GGATACAGGC | 5070 ACAACGGCTA | 5080 AAAAACTGGG | 5090 CGAGACTTTG | 5100 ACCATCAAAG | 5110 GTGGGCAAAC |
| 5120 AGACACCAAT | 5130 AAGCTAACCG | 5140 ATAATAACAT | 5150 CGGTGTGGTA | 5160 GCAGGTACTG | 5170 ATGGCTTCAC | 5180 TGTCAAACTT |
| 5190 GCCAAAGACC | 5200 TAACCAATCT | 5210 TAACAGCGTT | 5220 AATGCAGGTG | 5230 GCACCAAAAT | 5240 TGATGACAAA | 5250 GGCGTGTCTT |
| 5260 TTGTAGACTC | 5270 AAGCGGTCAA | 5280 GCCAAAGCAA | 5290 ACACCCCTGT | 5300 GCTAAGTGCC | 5310 AATGGGCTGG | 5320 ACCTGGGTGG |
| 5330 CAAGGTCATC | 5340 AGTAATGTGG | 5350 GCAAAGGCAC | 5360 AAAAGATACC | 5370 GACGCTGCCA | 5380 ATGTACAACA | 5390 GTTAAACGAA |
| 5400 GTACGCCAACT | 5410 TGTTGGGTCT | 5420 TGGTAATGCT | 5430 GGTAATGATA | 5440 ACGCTGACGG | 5450 CAATCAGTA | 5460 AACATTGCCG |
| 5470 ACATCAAAAA | 5480 AGACCCAAAT | 5490 TCAGGTTCAT | 5500 CATCTAACCG | 5510 CACTGTCATC | 5520 AAAGCAGGCA | 5530 CGGTACTTGG |
| 5540 CGGTAAAGGT | 5550 AATAACGATA | 5560 CCGAAAAACT | 5570 TGCCACTGGT | 5580 GGTATACAAG | 5590 TGGGCGTGGA | 5600 TAAAGACGGC |
| 5610 AACGCTAACG | 5620 GCGATTTAAG | 5630 CAATGTTTGG | 5640 GTCAAAACCC | 5650 AAAAAGATGG | 5660 CAGCAAAAAA | 5670 GCCCTGCTCG |
| 5680 CCACTTATAA | 5690 CGCCGCAGGT | 5700 CAGACCAACT | 5710 ATTTGACCAA | 5720 CAACCCCGCA | 5730 GAAGCCATTG | 5740 ACAGAATAAA |

FIG.6J

```
      5750       5760       5770       5780       5790       5800       5810
TGAACAAGGT ATCCGCTTCT TCCATGTCAA CGATGGCAAT CAAGAGCCTG TGGTACAAGG GCGTAACGGC
      5820       5830       5840       5850       5860       5870       5880
ATTGACTCAA GTGCCTCAGG CAAGCACTCA GTGGCGATAG GTTTCCAGGC CAAGGCAGAT GGTGAAGCCG
      5890       5900       5910       5920       5930       5940       5950
CCGTTGCCAT AGGCAGACAA ACCCAAGCAG GCAACCAATC CATCGCCATC GGTGATAACG CACAAGCCAC
      5960       5970       5980       5990       6000       6010       6020
GGGCGATCAA TCCATCGCCA TCGGTACAGG CAATGTGGTA GCAGGTAAGC ACTCTGGTGC CATCGGCGAC
      6030       6040       6050       6060       6070       6080       6090
CCAAGCACTG TTAAGGCTGA TAACAGTTAC AGTGTGGGTA ATAACAACCA GTTTACCGAT GCCACTCAAA
      6100       6110       6120       6130       6140       6150       6160
CCGATGTCTT TGGTGTGGGC AATAACATCA CCGTGACCGA AAGTAACTCG GTTGCCTTAG GTTCAAACTC
      6170       6180       6190       6200       6210       6220       6230
TGCCATCAGT GCAGGCACAC ACGCAGGCAC ACAAGCCAAA AAATCTGACG GCACAGCAGG TACAACCACC
      6240       6250       6260       6270       6280       6290       6300
ACAGCAGGTG CAACCGGTAC GGTTAAAGGC TTTGCTGGAC AAACGGCGGT TGGTGCGGTC TCCGTGGGTG
      6310       6320       6330       6340       6350       6360       6370
CCTCAGGTGC TGAACGCCGT ATCCAAAATG TGGCAGCAGG TGAGGTCAGT GCCACCAGCA CCGATGCGGT
      6380       6390       6400       6410       6420       6430       6440
CAATGGTAGC CAGTTGTACA AAGCCACCCA AAGCATTGCC AACGCAACCA ATGAGCTTGA CCATCGTATC
```

FIG.6K

| | | | | | |
|---|---|---|---|---|---|
| 6450 | 6460 | 6470 | 6480 | 6490 | 6500 | 6510 |
| CACCAAAACG | AAAATAAGGC | CAATGCAGGG | ATTTCATCAG | CGATGGCGAT | GGCGTCCATG | CCACAAGCCT |
| 6520 | 6530 | 6540 | 6550 | 6560 | 6570 | 6580 |
| ACATTCCTGG | CAGATCCATG | GTTACCGGGG | GTATTGCCAC | CCACAACGGT | CAAGGTGCGG | TGGCAGTGGG |
| 6590 | 6600 | 6610 | 6620 | 6630 | 6640 | 6650 |
| ACTGTCGAAG | CTGTCGGATA | ATGGTCAATG | GGTATTTAAA | ATCAATGGTT | CAGCCGATAC | CCAAGGCCAT |
| 6660 | 6670 | 6680 | 6690 | 6700 | 6710 | 6720 |
| GTAGGGGCGG | CAGTTGGTGC | AGGTTTTCAC | TTTTAAGCCA | TAAATCGCAA | GATTTTACTT | AAAAATCAAT |
| 6730 | 6740 | 6750 | 6760 | 6770 | 6780 | 6790 |
| CTCACCATAG | TTGTATAAAA | CAGCATCAGC | ATCAGTCATA | TTACTGATGC | TGATGTTTTT | TATCACTTAA |
| 6800 | 6810 | 6820 | 6830 | 6840 | 6850 | 6860 |
| ACCATTTTAC | CGCTCAAGTG | ATTCTCTTTC | ACCATGACCA | AATCGCCATT | GATCATAGGT | AAACTTATTG |
| 6870 | 6880 | 6890 | 6900 | 6910 | 6920 | 6930 |
| AGTAAATTTT | ATCAATGTAG | TTGTTAGATA | TGGTTAAAAT | TGTGCCATTG | ACCAAAAAAT | GACCGATTTA |
| 6940 | 6950 | 6960 | 6970 | | | |
| TCCCGAAAAT | TTCTGATTAT | GATCCGTTGA | CCTGCAGGTC | GAC | | |

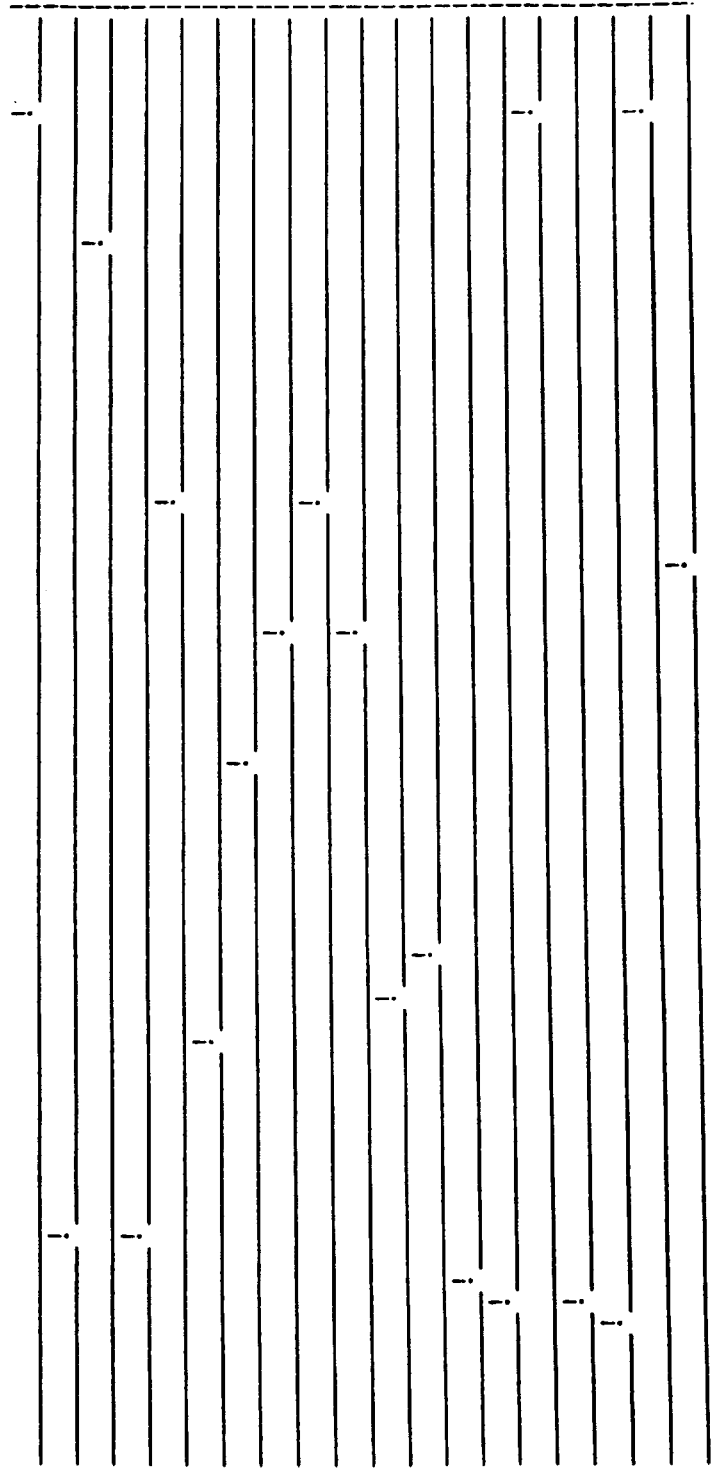
FIG. 7(a). con't.

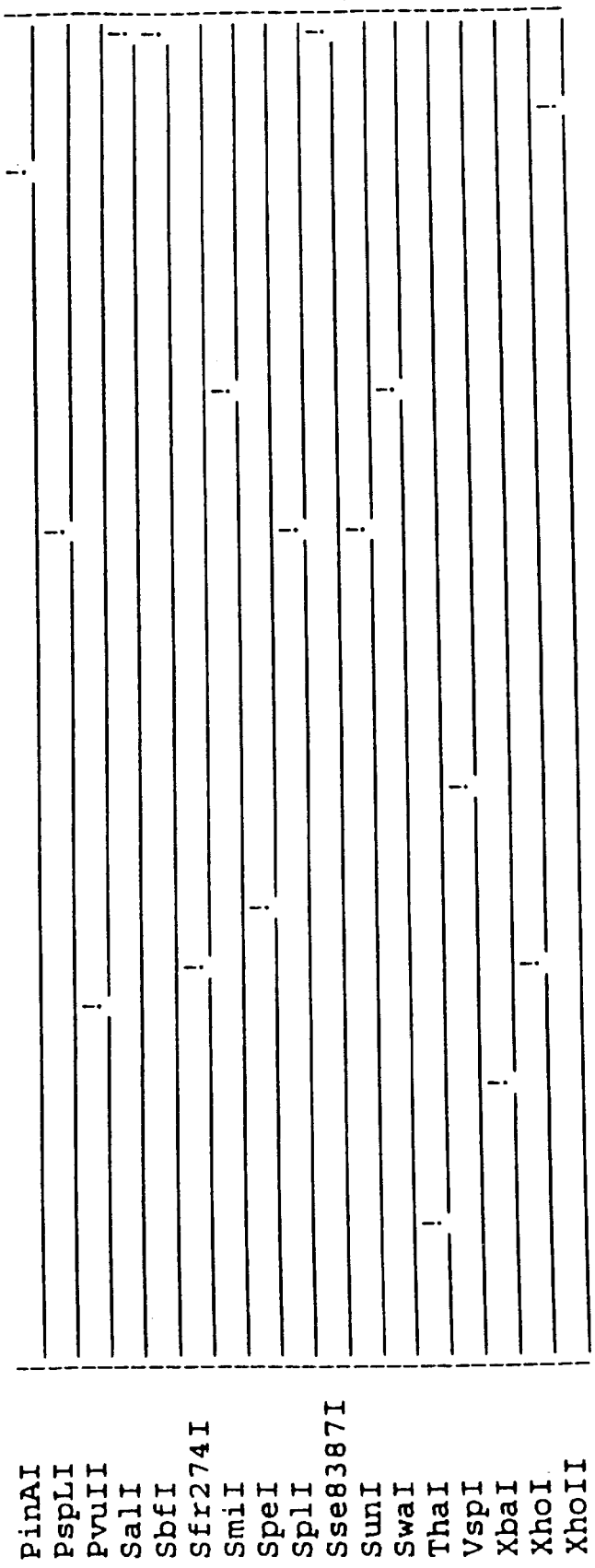
FIG. 7(a). con't.

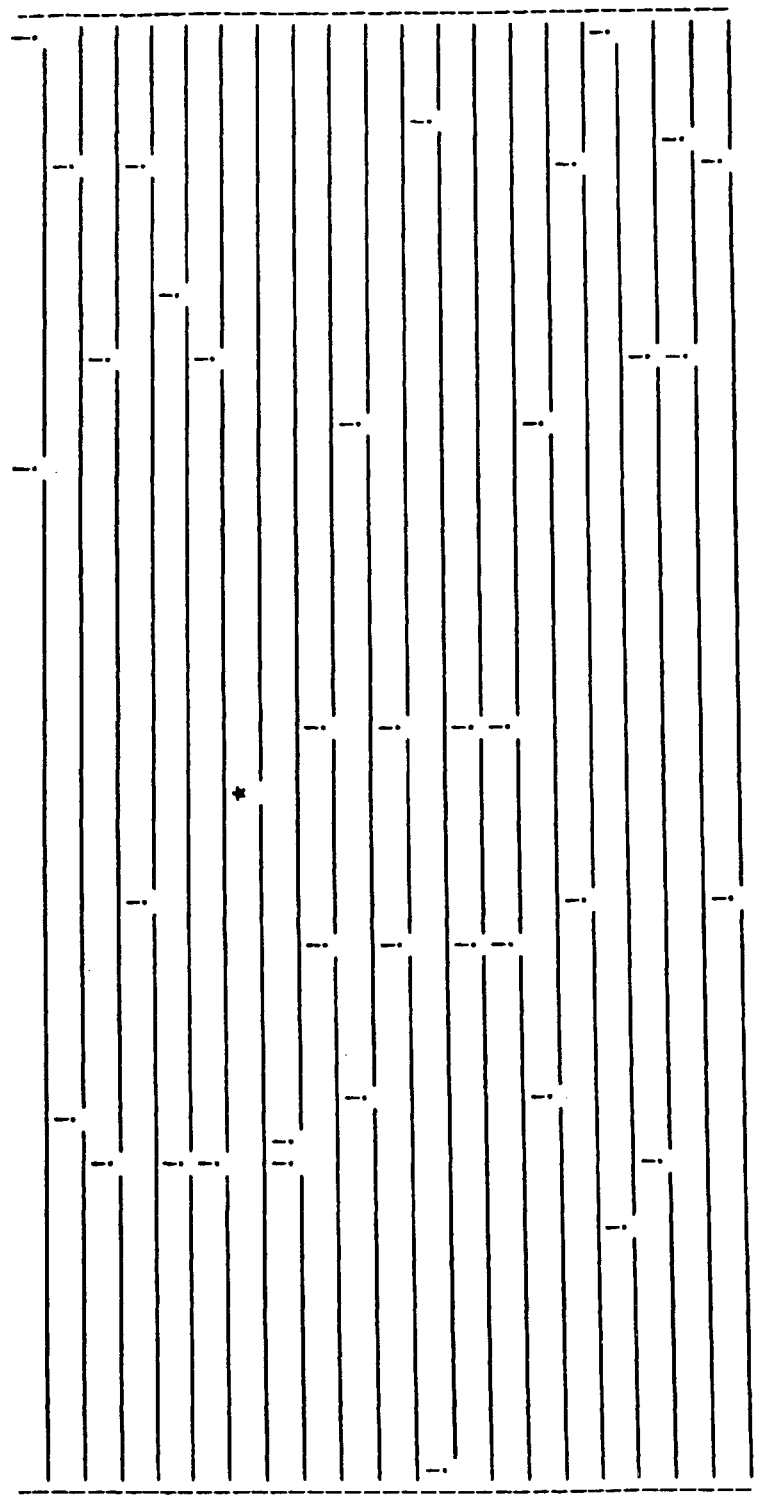
FIG. 7(b). con't.

_US 6,448,386 B2_

HIGH MOLECULAR WEIGHT MAJOR OUTER MEMBRANE PROTEIN OF MORAXELLA

REFERENCE TO RELATED APPLICATIONS

This application is a United States National Phase filing pursuant to 35 USC 371 of International Application PCT/CA96/00264 filed Apr. 29, 1996, which is a continuation-in-part of U.S. PAt. application No. 08/621,944 filed Mar. 20, 1996, which itself is a continuation-in-part of U.S. patent application Ser. No. 08/478,370, filed Jun. 7, 1995, (now U.S. Pat. No. 5,808,024) which itself is a continuation-in-part of U.S. patent application Ser. No. 08/431,718 filed May 1, 1995 now U.S. Pat. No. 6,335,018.

FIELD OF THE INVENTION

The present invention relates to the field of immunology and is particularly concerned with outer membrane proteins from Moraxella, methods of production thereof, genes encoding such proteins and uses thereof.

BACKGROUND OF THE INVENTION

Otitis media is the most common illness of early childhood with approximately 70% of all children suffering at least one bout of otitis media before the age of seven. Chronic otitis media can lead to hearing, speech and cognitive impairment in children. It is caused by bacterial infection with _Streptococcus pneumoniae_ (approximately 50%), non-typable _Haemophilus influenzae_ (approximately 30%) and _Moraxella (Branhamella) catarrhalis_ (approximately 20%). In the United States alone, treatment of otitis media costs between one and two billion dollars per year for antibiotics and surgical procedures, such as tonsillectomies, adenoidectomies and insertion of tympanostomy tubes. Because otitis media occurs at a time in life when language skills are developing at a rapid pace, developmental disabilities specifically related to learning and auditory perception have been documented in youngsters with frequent otitis media.

_M. catarrhalis_ mainly colonizes the respiratory tract and is predominantly a mucosal pathogen. Studies using cultures of middle ear fluid obtained by tympanocentesis have shown that _M. catarrhalis_ causes approximately 20% of cases of otitis media (ref. 1—Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure).

The incidence of otitis media caused by _M. catarrhalis_ is increasing. As ways of preventing otitis media caused by pneumococcus and non-typable _H. influenzae_ are developed, the relative importance of _M. catarrhalis_ as a cause of otitis media can be expected to further increase.

_M. catarrhalis_ is also an important cause of lower respiratory tract infections in adults, particularly in the setting of chronic bronchitis and emphysema (refs. 2, 3, 4, 5, 6, 7, and 8). _M. catarrhalis_ also causes sinusitis in children and adults (refs. 9, 10, 11, 12, and 13) and occasionally causes invasive disease (refs. 14, 15, 16, 17, 18, and 19).

Like other Gram-negative bacteria, the outer membrane of _M. catarrhalis_ consists of phospholipids, lipopolysaccharide (LPS), and outer membrane proteins (OMPs). Eight of the _M. catarrhalis_ OMPs have been identified as major components. These are designated by letters A to H, beginning with OMP A which has a molecular mass of 98 kDa to OMP H which has a molecular mass of 21 kDa (ref. 20).

Recently, a high-molecular-weight outer membrane protein of _M. catarrhalis_ was purified and characterized (ref. 21). The apparent molecular mass of this protein varies from 350 kDa to 720 kDa as judged by sodium dodecyl sulfate-polyacrylamide gel electrophoresis (SDS-PAGE). This protein appears to be an oligomer of much smaller proteins or subunits thereof of molecular mass 120 to 140 kDa and is antigenically conserved among strains of Moraxella.

A protein molecular mass of about 300 to 400 kDa named UspA was also reported to be present on the surface of Moraxella (ref. 22).

_M. catarrhalis_ infection may lead to serious disease. It would be advantageous to provide other outer membrane proteins for _M. catarrhalis_ and genes encoding such proteins for use as antigens in immunogenic preparations including vaccines, carriers for other antigens and immunogens and the generation of diagnostic reagents.

SUMMARY OF THE INVENTION

The present invention is directed towards the provision of a purified and isolated major outer membrane protein of _Moraxella catarrhalis_ and other Moraxella strains, having an apparent molecular mass of about 200 kDa, as well as genes encoding the same.

In accordance with one aspect of the invention, there is provided an isolated and purified, outer membrane protein of a Moraxella strain having a molecular weight of about 200 kDa, as determined by SDS-PAGE, or a fragment or an analog thereof. The outer membrane protein may be substantially in its native conformation (so as to have substantially retained the characteristic immunogenicity of the outer membrane protein in the Moraxella strain) and may be isolated from a _M. catarrhalis_ strain, such as from _M. catarrhalis_ 4223. Such isolated and purified about 200 kDa outer membrane protein is substantially free from non-200 kDa outer membrane proteins, phospholipids and lipopolysaccharide of Moraxella. The about 200 kDa outer membrane protein is at least about 70 wt % pure, preferably at least about 90 wt % pure, and may be in the form of an aqueous solution thereof. Such about 200 kDa outer membrane protein may have substantially the amino acid composition shown in Table III and a deduced amino acid sequence as shown in FIG. 6 (SEQ ID No: 3).

The present invention also provides a purified and isolated nucleic acid molecule encoding an outer membrane protein of a strain of Moraxella having a molecular mass of about 200 kDa, as determined by SDS-PAGE, or a fragment or an analog of the outer membrane protein. The protein encoded by the nucleic acid molecule may comprise a protein containing the amino acid sequence NH$_2$-Asn-Val-Lys-Ser-Val-Ile-Asn-Lys-Glu-Gln-Val-Asn-Asp-Ala-Asn-Lys-x-Gln-Gly-Ile (SEQ ID No: 5) particularly where X is Lys (SEQ ID No: 18), for _Moraxella catarrhalis_ strain 4223 or containing the corresponding amino acid sequence from other Moraxella strains.

In a further aspect of the present invention, there is provided a purified and isolated nucleic acid molecule having a sequence selected from the group consisting of (a) a DNA sequence as set out in FIG. 6 (SEQ ID Nos: 1 or 2), or the complementary sequence thereto; (b) a DNA sequence encoding an about 200 kDa protein of a strain of Moraxella and containing the amino acid sequence NH$_2$-Asn-Val-Lys-Ser-Val-Ile-Asn-Lys-Glu-Gln-Val-Asn-Asp-Ala-Asn-Lys-x-

Gln-Gly-Ile (SEQ ID No: 5), particularly where x is Lys (SEQ ID No: 18) or the complementary sequence thereto; (c) a DNA sequence encoding the deduced amino acid sequence as set out in FIG. 6 (SEQ ID No: 3) or the complementary sequence thereto; and (d) a nucleotide sequence which hybridizes under stringent conditions to any one of the sequences defined in (a), (b) or (c). The nucleic acid preferably defined in (d) has at least about 90% sequence identity with any one of the sequences defined in (a), (b) or (c).

The nucleic acid molecules provided herein may be included in a vector adapted for transformation of a host. The nucleic acid molecules provided herein also may be included in an expression vector adapted for transformation of a host along with expression means operatively coupled to the nucleic acid molecule for expression by the host of the about 200 kDa outer membrane protein of a strain of Moraxella or the fragment or the analog of the outer membrane protein. A transformed host containing the expression vector is included within the invention, along with a recombinant outer membrane protein or fragment or analog thereof producible by the transformed host.

The expression means may include a nucleic acid portion encoding a leader sequence for secretion from the host of the outer membrane protein or the fragment or the analog of the outer membrane protein. The expression means may include a nucleic acid portion encoding a lipidation signal for expression from the host of a lipidated form of the outer membrane protein or the fragment or analog thereof.

The present invention further includes a live vector for delivery of the outer membrane protein of the invention or a fragment or analog thereof, comprising a vector containing the nucleic acid molecule provided herein. The live vector may be selected from the group consisting of *E. coli*, Salmonella, BCG, adenovirus, poxvirus, vaccinia and poliovirus.

In accordance with a further aspect of the present invention, there is provided a peptide having no less than six amino acids and no more than 150 amino acids and containing an amino acid sequence corresponding to a portion only of the outer membrane protein of the invention, or a fragment or analog thereof. The peptide may be one having the amino acid sequence NH$_2$-Asn-Val-Lys-Ser-Val-Ile-Asn-Lys-Glu-Gln-Val-Asn-Asp-Ala-Asn-Lys-Lys-Gln-Gly-Ile (SEQ ID No: 18) for the *Moraxella catarrhalis* 4223 strain or the amino acid sequence for the corresponding peptide for other strains of Moraxella.

The present invention also provides an immunogenic composition comprising an immunoeffective amount of an active component, which may be the outer membrane protein or fragment or analog thereof, nucleic acid molecules, recombinant outer membrane proteins, fragments or analogs thereof, live vectors, and/or peptides, as provided herein, along with a pharmaceutically acceptable carrier therefor with the active component producing an immune response when administered to a host, which may be a primate, particularly a human.

The immunogenic composition may be formulated as a vaccine for in vivo administration to a host to confer protection against diseases caused by a bacterial pathogen that produces the about 200 kDa outer membrane protein or produces a protein capable of inducing antibodies in the host specifically reactive with the about 200 kDa outer membrane protein. In particular, the bacterial pathogen is a strain of Moraxella, particularly *M. catarrhalis*.

The immunogenic composition may be formulated as a microparticle capsule, ISCOM or liposome preparation. The immunogenic composition may be used in combination with a targeting molecule for delivery to specific cells of the immune system as to mucosal surfaces. Some targeting molecules include vitamin B12 and fragments of bacterial toxins, as described in WO 92/17167 (Biotech Australia Pty. Ltd.) and monoclonal antibodies, as described in U.S. Pat. No. 5,194,254 (Barber et al). The immunogenic compositions of the invention (including vaccines) may further comprise at least one other immunogenic or immunostimulating material and the immunostimulating material may be at least one adjuvant.

Suitable adjuvants for use in the present invention include, (but are not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of an amino acid, a muramyl dipeptide, polyphosphazene, ISCOPREP, DC-chol, DDBA and a lipoprotein. Advantageous combinations of adjuvants are described in copending U.S. patent application Ser. Nos. 08/261,194 filed Jun. 16, 1994 and 08/483,856, filed Jun. 7, 1995, assigned to the assignee hereof and the disclosures of which is incorporated herein by reference thereto. The invention further includes an antibody specific for the outer membrane protein provided herein producible by immunizing a host with an immunogenic composition as provided herein.

In a further aspect of the invention, there is provided a method of generating an immune response in a host comprising administering thereto an immuno-effective amount of the immunogenic composition as provided herein. The immune response may be a humoral or a cell-mediated immune response. The immune response may provide protection to the host against diseases caused by a bacterial pathogen that produces the about 200 kDa outer membrane protein or produces a protein capable of inducing antibodies in the host specifically reactive with the about 200 kDa outer membrane protein. In particular, the pathogen is a strain of Moraxella, including *M. catarrhalis*. Hosts in which protection against disease may be conferred include primates, including humans.

The present invention provides, in an additional aspect thereof, a method of producing a vaccine comprising administering the immunogenic composition provided herein to a test host to determine an amount and a frequency of administration of the active component to confer protection against disease caused by a bacterial pathogen that produces the about 200 kDa outer membrane protein or produces a protein capable of inducing antibodies in the host specifically reactive with the about 200 kDa outer membrane protein, and formulating the active component in a form and amount suitable for administration to a treated host in accordance with said determined amount and frequency of administration. In particular, the pathogen is a strain of Moraxella, including *M. catarrhalis*. The treated host may be a human.

A further aspect of the present invention provides a method of determining the presence of nucleic acid encoding an outer membrane protein of a strain of Moraxella having a molecular mass of about 200 kDa, as determined by SDS-PAGE, or fragment or analog thereof, in a sample, comprising the steps of:

(a) contacting the sample with the nucleic acid molecule provided herein to produce duplexes comprising the nucleic acid molecule and any said nucleic acid molecule encoding the outer membrane protein present in the sample and specifically hybridizable therewith; and (b) determining the production of the duplexes.

In yet a further aspect of the invention, there is provided a method of determining the presence of antibodies specifically reactive with outer membrane protein of a strain of Moraxella having a molecular mass of about 200 kDa, in a sample, comprising the steps of:

(a) contacting the sample with the outer membrane protein as provided herein to produce complexes comprising the outer membrane protein and any said antibodies present in the sample specifically reactive therewith; and (b) determining production of the complexes.

In a further aspect of the invention, there is also provided a method of determining the presence of an outer membrane protein of a strain of Moraxella having a molecular mass of about 200 kDa, in a sample comprising the steps of:

(a) immunizing a subject with the immunogenic composition as provided herein, to produce antibodies specific for the outer membrane protein;

(b) contacting the sample with the antibodies to produce complexes comprising any outer membrane protein present in the sample and said outer membrane protein specific antibodies; and (c) determining production of the complexes.

The outer membrane protein may be part of a *Moraxella catarrhalis* strain.

The present invention provides, in a yet further aspect, a diagnostic kit for determining the presence of nucleic acid encoding an outer membrane protein of a strain of Moraxella having a molecular mass of about 200 kDa, as determined by SDS-PAGE, or fragment or analog thereof, in a sample, comprising:

(a) the nucleic acid molecule as provided herein;

(b) means for contacting the nucleic acid with the sample to produce duplexes comprising the nucleic acid molecule and any said nucleic acid present in the sample and hybridizable with the nucleic acid molecule; and (c) means for determining production of the duplexes.

In yet a further aspect of the invention, there is provided a diagnostic kit for determining the presence of antibodies in a sample specifically reactive with the outer membrane protein of a strain of Moraxella having a molecular mass of about 200 kDa, as determined by SDS-PAGE, comprising:

(a) the outer membrane protein as provided herein;

(b) means for contacting the outer membrane protein with the sample to produce complexes comprising the outer membrane protein and any said antibodies present in the sample; and (c) means for determining production of the complexes.

The invention also provides a diagnostic kit for detecting the presence of an outer membrane protein of a strain of Moraxella having a molecular mass of about 200 kDa, in a sample, comprising:

(a) an antibody specific for the about 200 kDa outer membrane protein as provided herein;

(b) means for contacting the antibody with the sample to produce a complex comprising the outer membrane protein and outer membrane-specific antibody; and (c) means for determining production of the complex.

In a further aspect of the invention, there is provided a method of producing an isolated and purified outer membrane protein of a strain of Moraxella having a molecular mass of about 200 kDa, as determined by SDS-PAGE, comprising the steps of:

(a) providing a cell mass of the Moraxella strain;

(b) disrupting the cell mass to provide a cell lysate;

(c) fractionating the cell lysate to provide a fraction containing the outer membrane protein substantially free from other cell lysate components, and (d) recovering said outer membrane protein.

The bacterial strain may be *M. catarrhalis*. The cell lysate may be fractionated by gel electrophoresis.

In this application, the term "about 200 kDa protein" is used to define a family of outer membrane proteins of Moraxella having a molecular mass of between about 160 and about 230 kDa and includes proteins having variations in their amino acid sequences including those naturally occurring in various strains of Moraxella. The purified and isolated DNA molecules comprising a gene encoding the about 200 kDa protein of the present invention also include those encoding functional analogs of the about 200 kDa protein. In this application, a first protein is a "functional analog" of a second protein if the first protein is immunologically related to and/or has the same function as the second protein. The functional analog may be, for example, a fragment of the protein or a substitution, addition, deletion mutant thereof or a fusion with a second protein.

Advantages of the present invention include:

a method for isolating purified about 200 kDa outer membrane protein of a Moraxella strain that produces the outer membrane protein, including *M. catarrhalis*;

a gene encoding an about 200 kDa outer membrane protein of *M. catarrhalis*;

an isolated and purified about 200 kDa outer membrane protein isolatable from a Moraxella strain; and diagnostic kits and immunological reagents for specific identification of Moraxella and hosts infected thereby.

BRIEF DESCRIPTION OF THE DRAWINGS

FIGS. 6A to 6K show the nucleotide sequence (SEQ ID No: 1—entire sequence, SEQ ID No: 2—coding sequence) of the gene encoding the about 200 kDa outer membrane protein of *M. catarrhalis* and the deduced amino acid sequence (SEQ ID No: 3—identified GTG start codon, SEQ ID No: 4—putative ATG start codon). Peptide 1 (SEQ ID No: 11) and Peptide 2 (SEQ ID No: 12) are identified by underlining;

GENERAL DESCRIPTION OF THE INVENTION

Figure 1A:
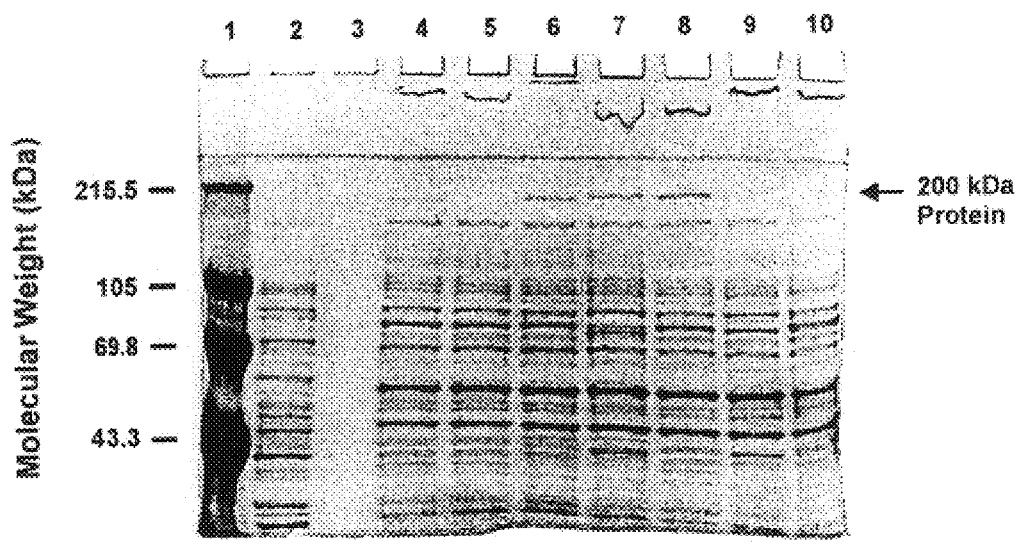
FIGS. 1A and 1B show an analysis of *Moraxella catarrhalis* cell proteins by SDS-PAGE. The identification of the lanes and the sources of the proteins are given in Example 2 below.
Figure 1B:
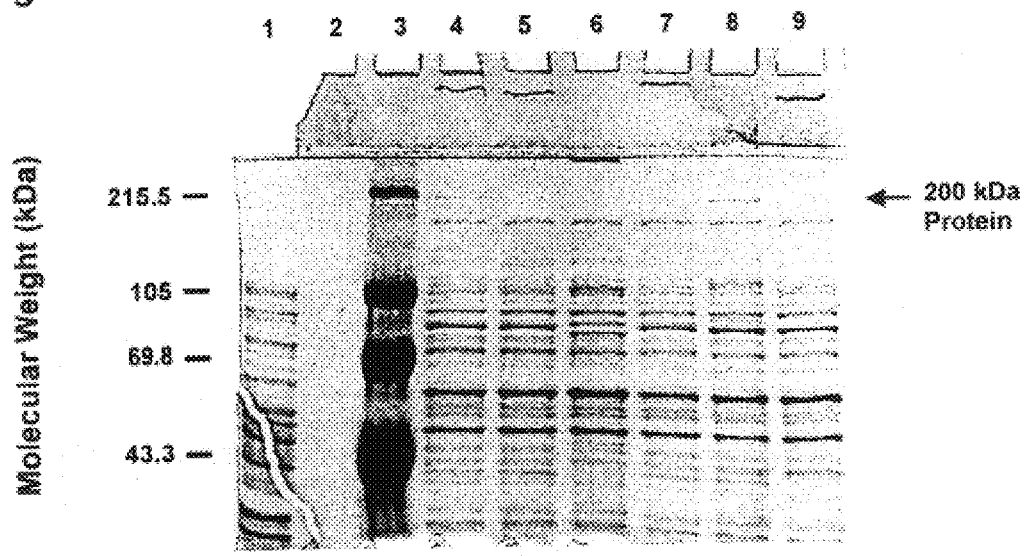
Figure 2:
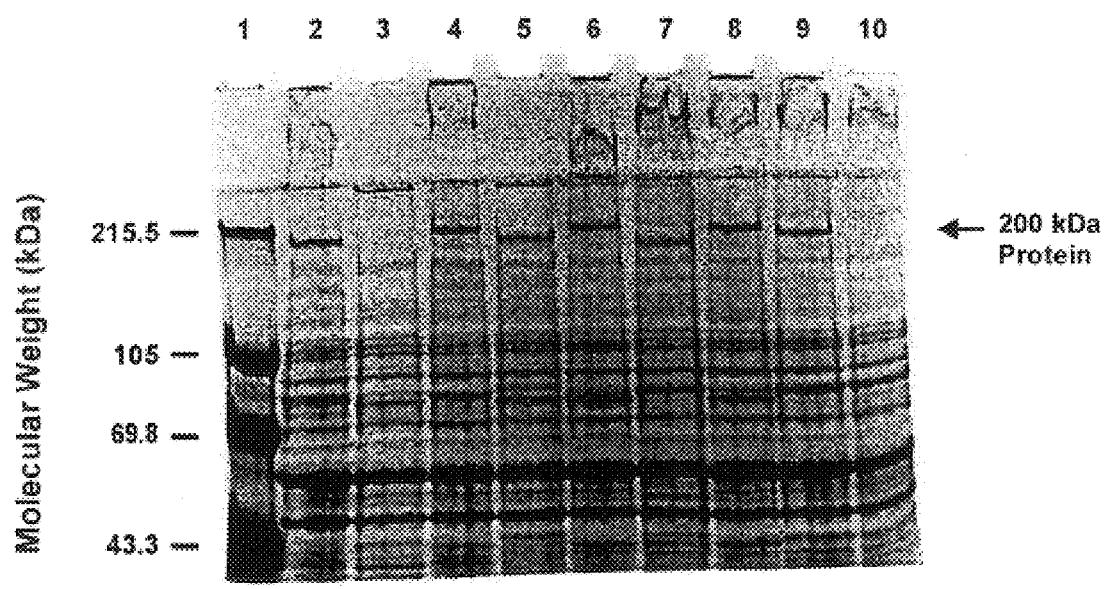
FIG. 2 shows a comparative analysis of cell proteins from a number of *M. catarrhalis* strains by SDS-PAGE analysis and shows the variability in the molecular weight of the about 200 kDa protein in different strains of Moraxella. The identification of the lanes and the sources of the proteins are given in Example 4 below.
Figure 3:
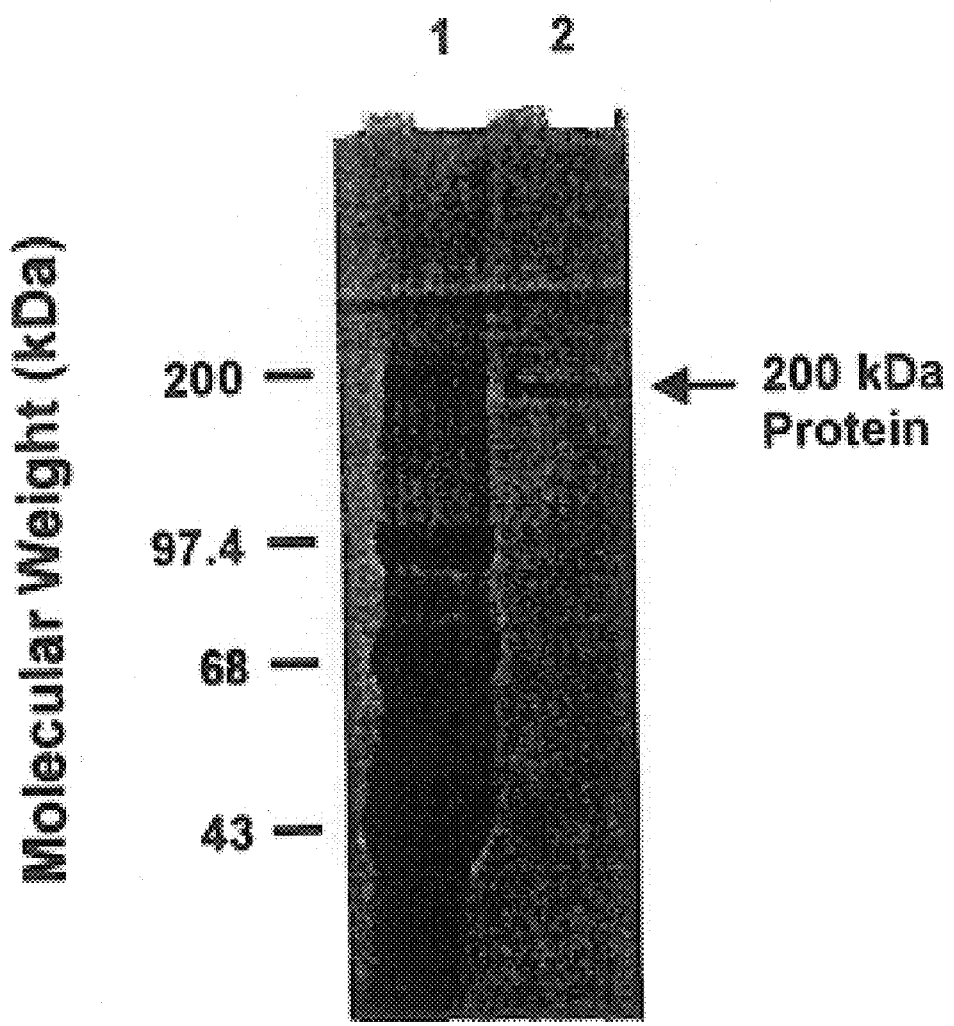
FIG. 3 shows an analysis of isolated and purified about 200 kDa outer membrane protein of *M. catarrhalis* by SDS-PAGE.

Referring to FIGS. 1A and 1B and FIG. 2, there is illustrated the separation of a novel outer membrane protein from a variety of strains of *M. catarrhalis* having a molecular mass about 200 kDa. The presence of this about 200 kDa protein in a variety of *M. catarrhalis* strains and, in particular, the almost-universal presence in strains isolated from patients suffering from otitis media is shown in Table I. FIG. 3 shows the isolated and purified outer membrane protein.

Purified protein was eluted from a gel and used to raise antibodies in guinea pigs. The antibodies specifically recognize only strains of *M. catarrhalis* which produce the outer membrane protein (Table I below).

Figure 4:
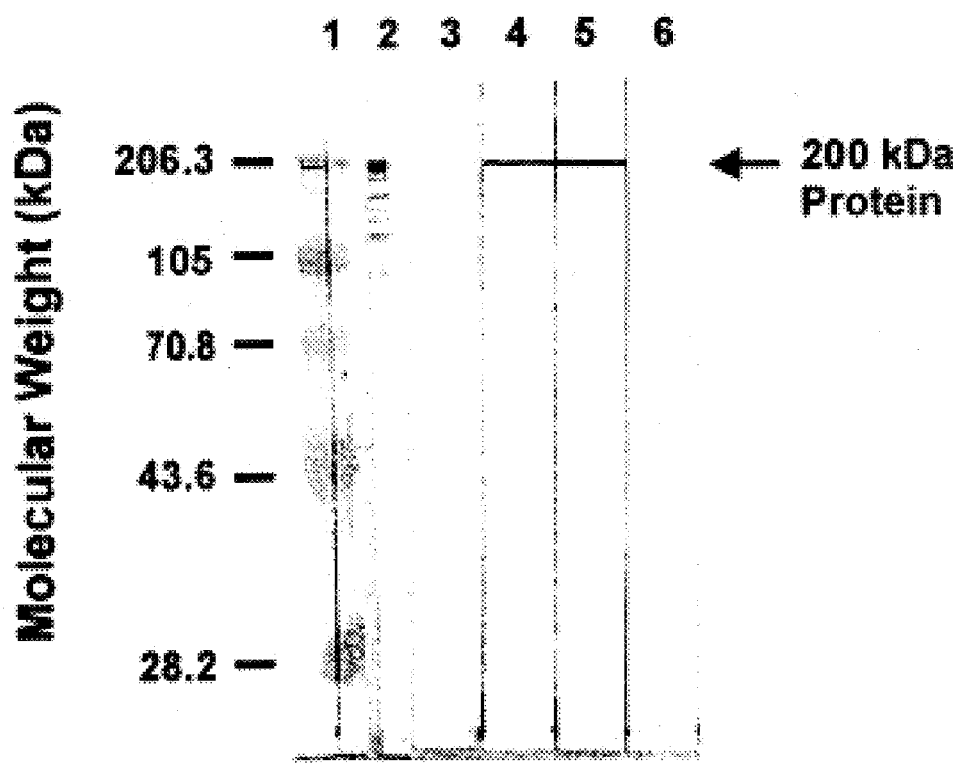
FIG. 4 shows the specific recognition of about 200 kDa outer membrane protein by anti-peptide antiserum. The identification of the lanes and antiserum are given in Example 8 below.

Referring to FIG. 4, there is shown the recognition of the about 200 kDa outer membrane protein by antibodies raised in guinea pigs to a synthesized peptide corresponding to an internal fragment of the about 200 kDa protein. The synthesized peptide had the amino acid sequence NH$_2$-Asn-Val-Lys-Ser-Val-Ile-Asn-Lys-Glu-Gln-Val-Asn-Asp-Ala-Asn-Lys (SEQ ID No: 6).

Figure 5:
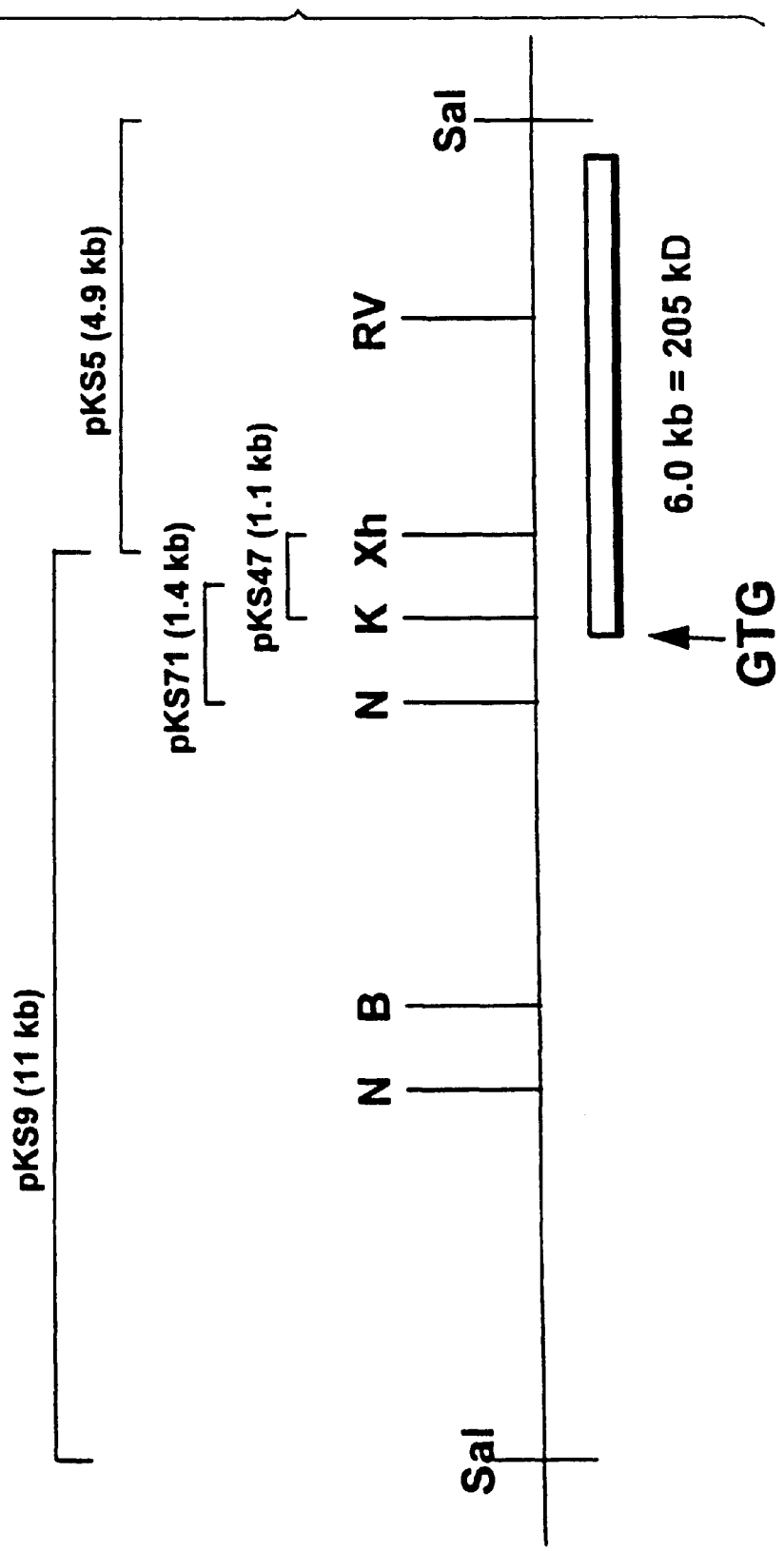
FIG. 5 shows restriction maps of clones containing a gene encoding the about 200 kDa outer membrane protein of *M. catarrhalis*. The open reading frame of the about 200 kDa outer membrane protein is indicated by the shaded box. Restriction sites are Sal: SalI, N: NcoI, B: BglII, K: KpnI, Xh: XhoI, RV: EcoRV.
Figure 7A:
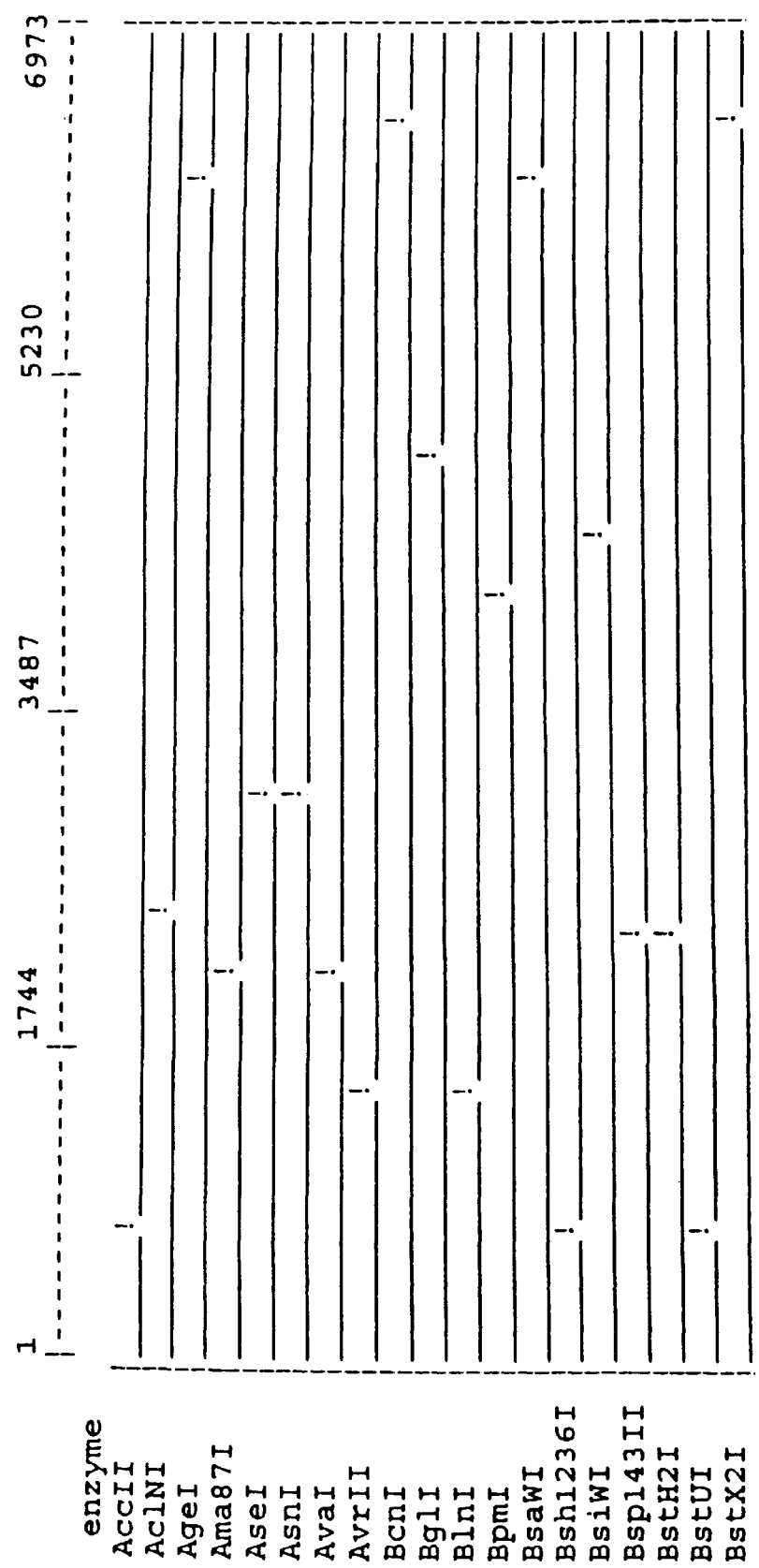
FIG. 7A is a restriction enzyme map of the gene encoding the about 200 kDa outer membrane protein of *M. catarrhalis* (SEQ ID No: 1) showing single cutting restriction enzymes.
Figure 7B:
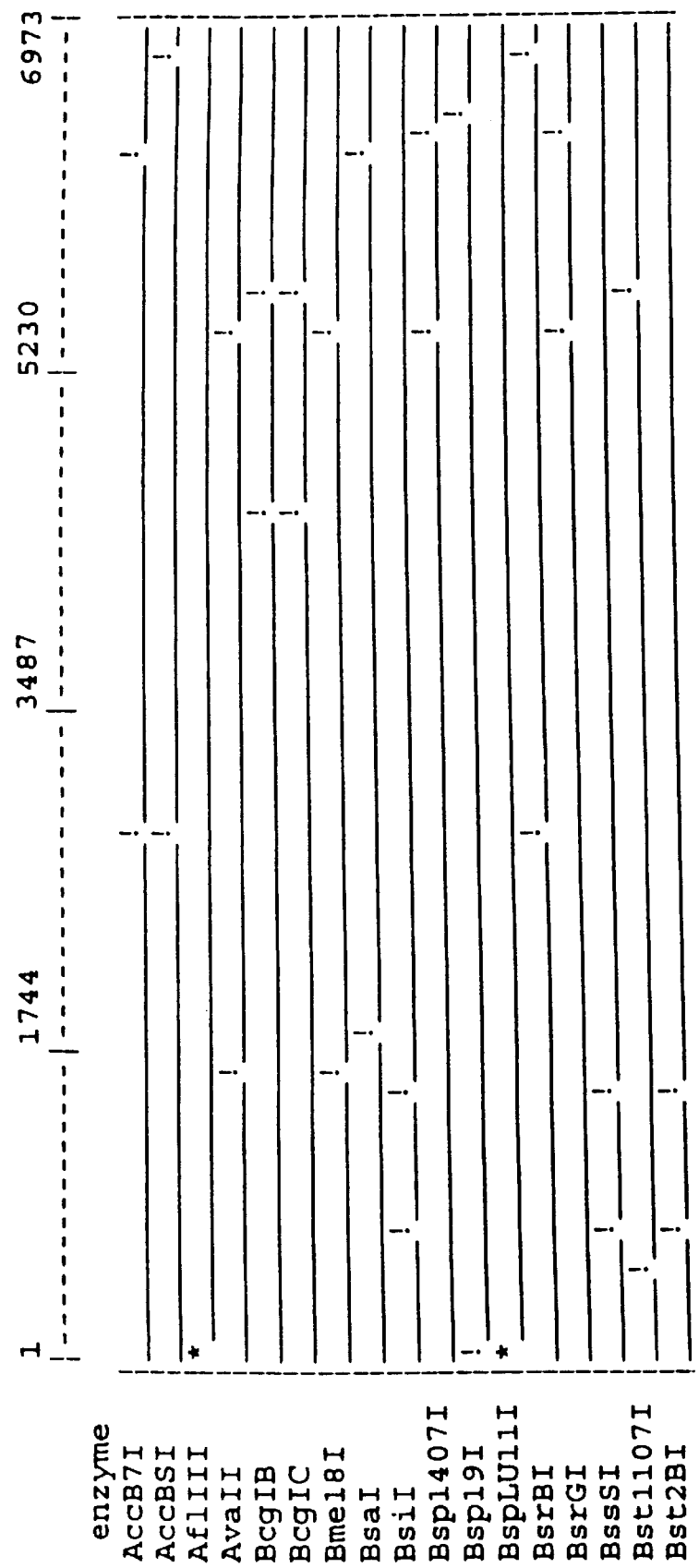
FIG. 7B is a restriction enzyme map of the gene encoding about 200 kDa outer membrane protein of *M. catarrhalis* (SEQ ID No: 1) showing double cutting restriction enzymes.

Referring to FIG. 5, there is shown restriction maps of clones containing a gene encoding the about 200 kDa outer membrane protein. In FIG. 5, the open reading frame of the about 200 kDa gene is shown as a solid box and the GTG start codon is indicated. The nucleotide sequence (SEQ ID No: 1 and 2) of the gene encoding the about 200 kDa outer membrane protein is shown in FIG. 6, along with the deduced amino acid sequence (SEQ ID No: 3) of the protein. Restriction enzyme maps of the gene encoding the about 200 kDa protein are shown in FIGS. 7(A) and 7(B). The amino acid composition of the about 200 kDa protein is shown in Table III.

In one embodiment of the present invention, the isolated and purified about 200 kDa outer membrane protein as provided herein is useful for generating antibodies that can be used to specifically distinguish *M. catarrhalis* from other bacterial pathogens that cause otitis media and other diseases. Thus referring to FIG. 14, there is illustrated an immunoblot showing the specific reactivity of a guinea pig monospecific anti-200 kDa outer membrane protein antiserum produced by immunizing mice with the purified about 200 kDa outer membrane protein as provided herein. The bacterial lysates analyzed were as follows:

| Lane | Bacterium | Source |
|---|---|---|
| 1. | Molecular Weight Standard | |
| 2. | *M. catarrhalis* 4223 | middle ear fluid |
| 3. | *M. catarrhalis* RH408 | non-clumping variant of strain 4223 |
| 4. | *H. influenzae*, MinnA strain | meningitis isolate |
| 5. | non-typable *H. influenzae*, SB12 strain | otitis media isolate |
| 6. | non-typable *H. influenzae*, SB33 strain | otitis media isolate |
| 7. | *S. pneumoniae* type 6 | ATCC 6306 |
| 8. | *S. pneumoniae* type 14 | ATCC 6314 |
| 9. | *P. aeruginosa* | |
| 10. | *E. coli* DH5α | |

Figure 14:
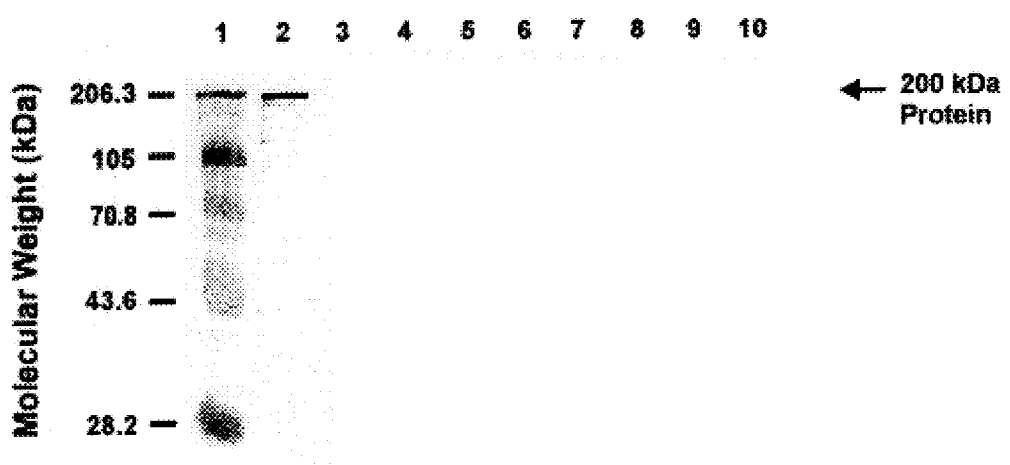
FIG. 14 shows the specific identification of *M. catarrhalis* expressing the about 200 kDa outer membrane protein by guinea pig anti-200 kDa specific antiserum in contrast to other bacteria. Identification of the lanes and bacteria appears below.

The results shown in FIG. 14 clearly show the usefulness of outer membrane-specific antisera as provided herein to distinguish between bacterial pathogens that produce diseases with similar clinical symptoms.

In accordance with another aspect of the present invention, there is provided a vaccine against Moraxella, comprising an immunogenically-effective amount of the outer membrane protein as provided herein and a physiologically-acceptable carrier therefor. The outer membrane protein provided herein also may be used as a carrier protein for hapten, polysaccharides or peptides to make a conjugate vaccine against antigenic determinants unrelated to the about 200 kDa outer membrane protein.

The about 200 kDa outer membrane protein provided herein is useful as a diagnostic reagent, as an antigen for the generation of anti-outer membrane protein antibodies, or as an antigen for vaccination against the diseases caused by species of Moraxella or for detecting infection by Moraxella.

In additional embodiments of the present invention, the about 200 kDa outer membrane protein as provided herein may be used as a carrier molecule to prepare chimeric molecules and conjugate vaccines (including glycoconjugates) against pathogenic bacteria, including encapsulated bacteria. Thus, for example, glycoconjugates of the present invention may be used to confer protection against disease and infection caused by any bacteria having polysaccharide antigens including lipooligosaccharides (LOS) and polyribosylphosphate (PRP). Such bacterial pathogens may include, for example, *Haemophilus influenzae, Streptococcus pneumoniae, Escherichia coli, Neisseria meningitidis, Salmonella typhi, Streptococcus mutants, Cryptococcus neoformans*, Klebsiella, *Staphylococcus aureus* and *Pseudomonas aeruginosa*. Particular antigens which can be conjugated to outer membrane protein and methods to achieve such conjugations are described in published PCT application WO 94/12641, assigned to the assignee hereof and the disclosure of which is hereby incorporated by reference thereto.

In another embodiment, the carrier function of the outer membrane protein may be used, for example, to induce immunity toward abnormal polysaccharides of tumor cells, or to produce anti-tumor antibodies that can be conjugated to chemotherapeutic or bioactive agents.

The present invention extends to the use of the nucleic acid molecules and proteins provided herein as a medicament and in the manufacture of a medicament for the treatment of Moraxella infections.

Figure 11:
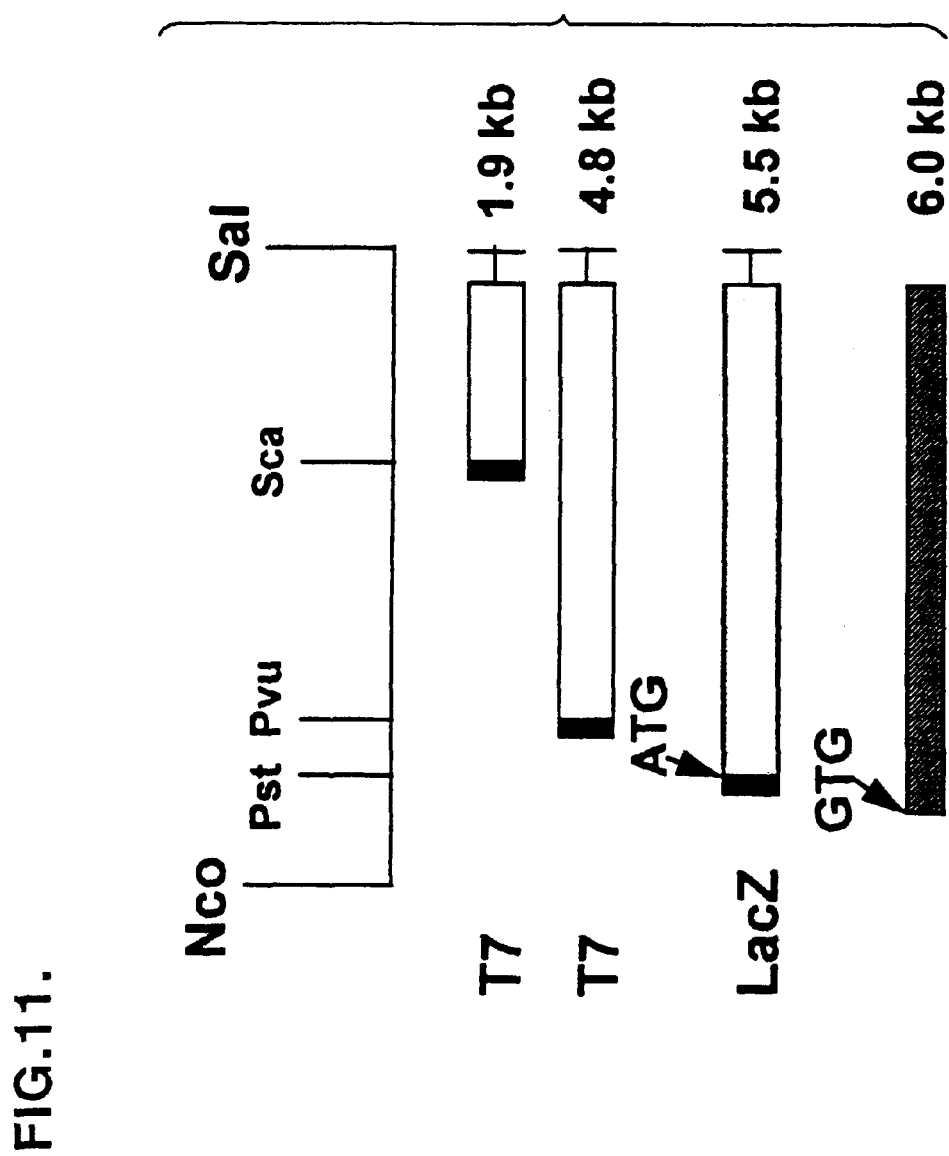
FIG. 11 shows the construction of vectors for the expression of the about 200 kDa outer membrane protein of *M. catarrhalis* from *E. coli*. Nco: NcoI, Pst: PstI, Pvu: PvuII, Sca: ScaI, Sal: SalI.

In a particular embodiment of the invention, there is provided a recombinant about 200 kDa outer membrane protein of Moraxella or fragment or analog thereof or a fusion protein producible by a transformed host containing at least a portion of the gene encoding the about 200 kDa protein. Referring to FIG. 11, there is shown recombinant vectors for the production of such proteins. In FIG. 11, the filled boxes show 1.9 kb and 4.8 kb C-terminal regions of 200 kD protein gene, that were inserted into a vector, pT7—7, under the control of the bacteriophage T7 promoter. The small open boxes show seven N- terminal amino acids from the vector in the same reading frame. The shaded box shows 5.5 kb C-terminal region of 200 kD protein, which contained ATG codon very close to the N-terminus. This gene fragment was fused to lacZ α peptide gene (shown in filled box) under the control of lacZ promoter. The full-length gene, that starts from GTG, is shown in a hatched box.

Figure 12:
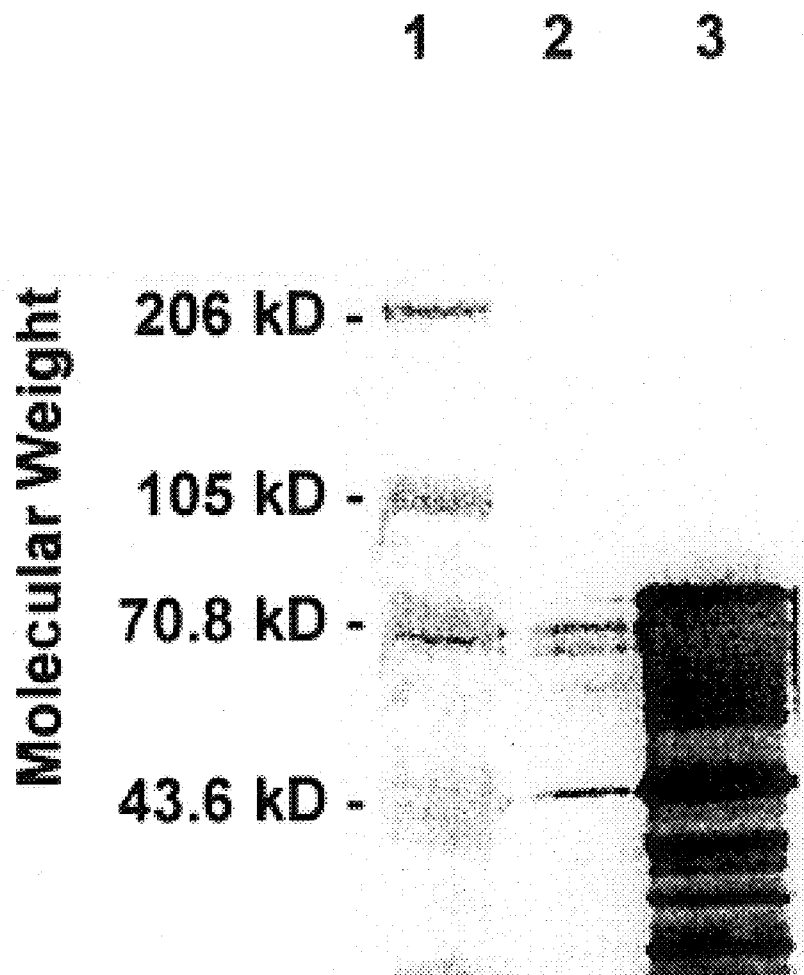
FIG. 12 shows the expression of N-terminal truncations of the about 200 kDa outer membrane protein of *M. catarrhalis* in *E. coli* using the bacteriophage T7 promoter.

Referring to FIG. 12, there is shown the expression of N-terminal truncations of the about 200 kDa protein in *E. coli*. *E. coli* strain, BL21(DE3)/pLysS, carrying plasmid, pKS94, was grown in LB broth containing 100 μg/ml ampicillin to the early log phase and then IPTG was added. After culturing for 2 more hours, the bacteria were harvested and lysed. The lysates were assayed on Western blot using anti-200 kD protein guinea pig serum as a first antibody. Other procedures were as in FIG. 5. Lane 1: prestained molecular weight marker, Lane 2: BL21(DE3)/pLysS carrying pT7—7 with an incorrect insert. Lane 3: L21(DE3)/pLysS carrying pKS94.

Figure 13:
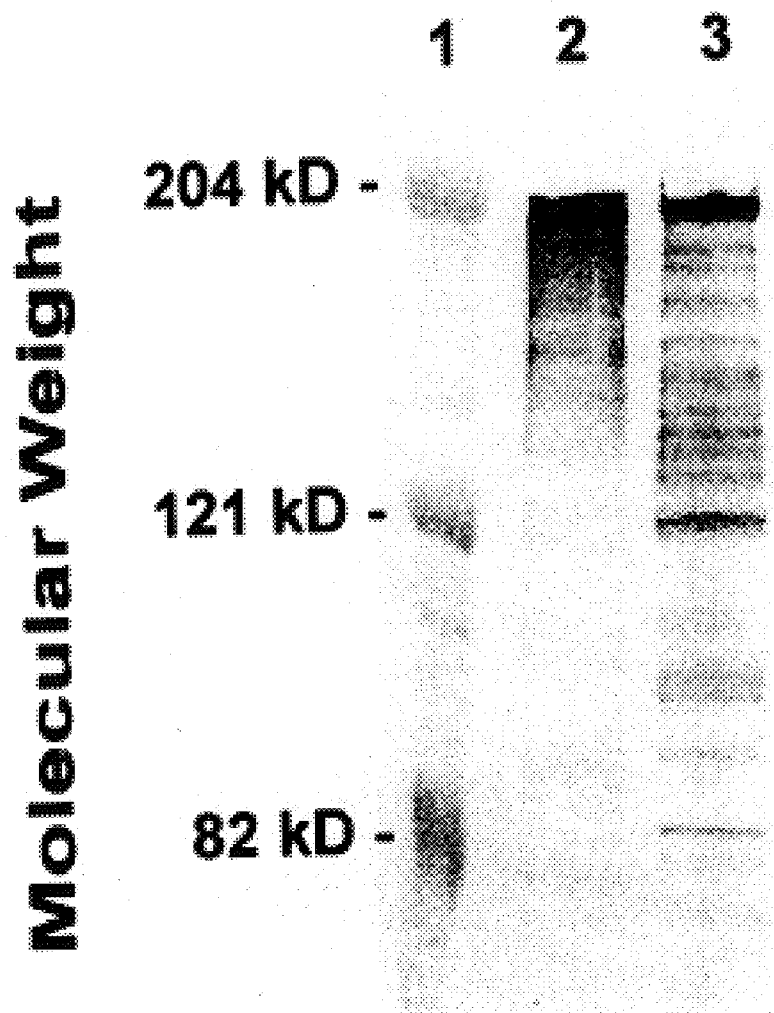
FIG. 13 shows the expression of the about 200 kDa outer membrane protein of *M. catarrhalis* fused with the LacZ-α-peptide in *E. coli*.

Referring to FIG. 13, there is shown the expression of fusion protein comprising the β-galactosidase α peptide and a portion of the about 200 kDa protein in *E. coli*. *E. coli* strain, DH5α, carried pKS140. The plasmid pKS140 carried the C-terminal 5.5 kb fragment of 200 kD protein gene after a N-terminal portion of LacZ-α-peptide in the same reading frame. The *E. coli* strain was grown to the stationary phase, harvested and then lysed. The lysate was assayed by Western blotting. Lane 1: prestained molecular weight marker, Lane 2: DH5α carrying pKS140 (total protein, 0.5 μg), Lane 3: sonicate of *M. catarrhalis*, strain 4223 (total protein, 10 μg).

It is clearly apparent to one skilled in the art, that the various embodiments of the present invention have many applications in the fields of vaccination, diagnosis, treatment of Moraxella infections, and in the generation of immunological reagents. A further non-limiting discussion of such uses is further presented below.

1. Vaccine Preparation and Use

Immunogenic compositions, including those suitable to be used as vaccines, may be prepared from the about 200 kDa outer membrane protein as disclosed herein, as well as immunological fragments and fusions thereof, which may be purified from the bacteria or which may be produced recombinantly. The vaccine elicits an immune response in a subject which produces antibodies, including anti-200 kDa outer membrane protein antibodies and antibodies that are opsonizing or bactericidal. Should the vaccinated subject be challenged by Moraxella or other bacteria that produce proteins capable of producing antibodies that specifically recognize 200 kDa outer membrane protein, the antibodies bind to and inactivate the bacterium. Furthermore, opsonizing or bactericidal anti-200 kDa outer membrane protein antibodies may also provide protection by alternative mechanisms.

Immunogenic compositions including vaccines may be prepared as injectables, as liquid solutions or emulsions. The about 200 kDa outer membrane protein may be mixed with pharmaceutically acceptable excipients which are compatible with the about 200 kDa outer membrane protein. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 1 to 95% of the about 200 kDa outer membrane protein. The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the about 200 kDa outer membrane protein. Suitable regimes for initial administration and booster doses are also variable, but may include an initial administration followed by subsequent administrations. The dosage may also depend on the route of administration and will vary according to the size of the host.

The immunogenic preparations including vaccines may comprise as the immunostimulating material a nucleotide vector comprising at least a portion of the gene encoding the about 200 kDa protein, or the at least a portion of the gene may be used directly for immunization.

The concentration of the about 200 kDa outer membrane antigen in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the antigens are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum. While the usefulness of alum is well established for some applications, it has limitations. For example, alum is ineffective for influenza vaccination and inconsistently elicits a cell mediated immune response.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are typically emulsified in adjuvants. Many adjuvants are toxic, inducing granulomas, acute and chronic inflammations (Freund's complete adjuvant) FCA, cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes, if required;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto, teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. (U.S. Pat. No. 4,855,283 and ref. 27) reported that N-glycolipid analogs displaying structural similarities to the naturally-occurring glycolipids, such as glycosphospholipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functioned as an adjuvant when complexed with tetanus toxoid and formalin inactivated type I, II and III poliomyelitis virus vaccine. Also, Nixon-George et al. (ref. 24), reported that octadecyl esters of aromatic amino acids complexed with a recombinant hepatitis B surface antigen, enhanced the host immune responses against hepatitis B virus.

Lipidation of synthetic peptides has also been used to increase their immunogenicity. Thus, Wiesmuller (ref. 25) describes a peptide with a sequence homologous to a foot-and-mouth disease viral protein coupled to an adjuvant tripalmityl-S-glyceryl-cysteinylserylserine, being a synthetic analogue of the N-terminal part of the lipoprotein from Gram negative bacteria. Furthermore, Deres et al. (ref. 26) reported in vivo priming of virus-specific cytotoxic T lymphocytes with synthetic lipopeptide vaccine which comprised of modified synthetic peptides derived from influenza virus nucleoprotein by linkage to a lipopeptide, N-palmityl-S-[2,3-bis(palmitylxy)-(2RS)-propyl-[R]-cysteine (TPC).

2. Immunoassays

The about 200 kDa outer membrane protein of the present invention is useful as an immunogen for the generation of anti-200 kDa outer membrane protein antibodies, as an antigen in immunoassays including enzyme-linked immunosorbent assays (ELISA), RIAs and other non-enzyme linked antibody binding assays or procedures known in the art for the detection of anti-bacterial, anti-Moraxella, and anti-200 kDa outer membrane protein antibodies. In ELISA assays, the about 200 kDa outer membrane protein is immobilized onto a selected surface, for example, a surface capable of binding proteins such as the wells of a polystyrene microtiter plate. After washing to remove incompletely adsorbed about 200 kDa outer membrane protein, a nonspecific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures such as of the order of about 20° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound about 200 kDa outer membrane protein, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a colour development upon incubating with an appropriate chromogenic substrate. Quantification may then be achieved by measuring the degree of colour generation using, for example, a visible spectrophotometer.

3. Use of Sequences as Hybridization Probes

The nucleotide sequences of the present invention, comprising the sequence of the about 200 kDa protein gene, now allow for the identification and cloning of the about 200 kDa protein gene from any species of Moraxella.

The nucleotide sequences comprising the sequence of the about 200 kDa protein gene of the present invention are useful for their ability to selectively form duplex molecules with complementary stretches of other about 200 kDa protein genes. Depending on the application, a variety of hybridization conditions may be employed to achieve varying degrees of selectivity of the probe toward the other genes. For a high degree of selectivity, relatively stringent conditions are used to form the duplexes, such as low salt and/or high temperature conditions, such as provided by 0.02 M to 0.15 M NaCl at temperatures of between about 50° C. to 70° C. For some applications, less stringent hybridization conditions are required such as 0.15 M to 0.9 M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results. In general, convenient hybridization temperatures in the presence of 50% formamide are: 42° C. for a probe which is 95 to 100% homologous to the target fragment, 37° C. for 90 to 95% homology and 32° C. for 85 to 90% homology.

In a clinical diagnostic embodiment, the nucleic acid sequences of the about 200 kDa protein genes of the present invention may be used in combination with an appropriate means, such as a label, for determining hybridization. A wide variety of appropriate indicator means are known in the art, including radioactive, enzymatic or other ligands, such as avidin/biotin and digoxigenin-labelling, which are capable of providing a detectable signal. In some diagnostic embodiments, an enzyme tag such as urease, alkaline phosphatase or peroxidase, instead of a radioactive tag may be used. In the case of enzyme tags, colorimetric indicator substrates are known which can be employed to provide a means visible to the human eye or spectrophotometrically, to identify specific hybridization with samples containing about 200 kDa protein gene sequences.

The nucleic acid sequences of the about 200 kDa protein genes of the present invention are useful as hybridization probes in solution hybridizations and in embodiments employing solid-phase procedures. In embodiments involving solid-phase procedures, the test DNA (or RNA) from samples, such as clinical samples, including exudates, body fluids (e.g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the about 200 kDa protein encoding genes or fragments or analogs thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. It is preferred to select nucleic acid sequence portions which are conserved among species of Moraxella. The selected probe may be at least 18 bp and may be in the range of about 30 to 90 bp.

4. Expression of the About 200 kDa Protein Gene

Plasmid vectors containing replicon and control sequences which are derived from species compatible with the host cell may be used for the expression of the genes encoding the about 200 kDa protein in expression systems. The vector ordinarily carries a replication site, as well as marking sequences which are capable of providing phenotypic selection in transformed cells. For example, E. coli may be transformed using pBR322 which contains genes for ampicillin and tetracycline resistance and thus provides easy means for identifying transformed cells. The plasmids or phage, must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as E. coli LE392.

Promoters commonly used in recombinant DNA construction include the β-lactamase (penicillinase) and lactose promoter systems and other microbial promoters, such as the T7 promoter system as described in U.S. Pat. No. 4,952,496. Details concerning the nucleotide sequences of promoters are known, enabling a skilled worker to ligate them functionally with genes. The particular promoter used will generally be a matter of choice depending upon the desired results. Hosts that are appropriate for expression of the about 200 kDa protein genes, fragments, analogs or variants thereof, may include E. coli, Bacillus species, Haemophilus, fungi, yeast, Bordetella, or the baculovirus expression system may be used.

In accordance with this invention, it is preferred to make the protein by recombinant methods, particularly when the naturally occurring about 200 kDa protein as purified from a culture of a species of Moraxella may include trace amounts of toxic materials or other contaminants. This problem can be avoided by using recombinantly produced protein in heterologous systems which can be isolated from the host in a manner to minimize contaminants in the purified material. Particularly desirable hosts for expression in this regard include Gram positive bacteria which do not have LPS and are, therefore, endotoxin free. Such hosts include species of Bacillus and may be particularly useful for the production of non-pyrogenic about 200 kDa protein, fragments or analogs thereof.

BIOLOGICAL DEPOSITS

Certain plasmids that contain portions of the gene having the open reading frame of the gene encoding the about 200 kDa outer membrane protein of M. catarrhalis strain 4223 that are described and referred to herein have been deposited with the America Type Culture Collection (ATCC) located at U.S.A., pursuant to the Budapest Treaty and pursuant to 37 CFR 1.808 and prior to the filing of this application. The identifications of the respective portions of the gene present in these plasmids are shown in FIG. 5.

Samples of the deposited plasmids will become available to the public upon grant of a patent based upon this United States patent application. The invention described and claimed herein is not to be limited in scope by plasmids deposited, since the deposited embodiment is intended only as an illustration of the invention. Any equivalent or similar plasmids that encode similar or equivalent antigens as described in this application are within the scope of the invention.

| Plasmid | ATCC Designation | Date Deposited |
|---------|------------------|----------------|
| pKS47   | 97,111           | April 7, 1995  |
| pKS5    | 97,110           | April 7, 1995  |
| pKS9    | 97,114           | April 18, 1995 |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply reported in the scientific literature and are well within the ability of those skilled in the art.

Example 1

This Example illustrates the generation of a non-clumping strain (RH408) of *M. catarrhalis*.

*M. catarrhalis* strain 4223, a clumping strain (a common property of Moraxella strains), was inoculated into several flasks containing 20 mL of brain heat infusion (BHI) broth, and the cultures were incubated with shaking (170 rpm) overnight at 37° C. Five mL of each overnight culture were transferred to five individual 1 mL tubes, and were left sitting undisturbed at room temperature for 3 to 8 hours, to allow bacteria to sediment. One hundred $\mu$L of the cleared upper phase of each culture were used to inoculate 25 mL of BHI broth and cultures were incubated overnight at 37° C., as described above. This passaging was repeated six times, using 25 $\mu$L of cleared culture to inoculate 25 mL of BHI for each overnight culture. Non-clumping bacterial cultures were identified by measuring the absorbency $A_{578}$ at intervals over a 3 hour time period, in order to compare the sedimentation rates of the passaged strains to that of the original *M. catarrhalis* strain 4223 culture. Non-clumping mutants, including *M. catarrhalis* RH408, did not aggregate during the three hour time period. On BHI agar plates, strain RH408 had a colony morphology typical for all non-clumping strains. Strain RH408 was previously deposited in connection of U.S. application Ser. No. 08/328,589 at the ATCC under the Budapest Treaty on Dec. 13, 1994 with Accession No. 55637.

Example 2

This Example illustrates the identification of the about 200 kDa outer membrane protein of *Moraxella catarrhalis*.

*M. catarrhalis* strains 4223, RH408, 5191, 8185, M2, M5, ATCC 25240, 3, 56, 135, 585 were grown in brain heart infusion (BHI) broth. The culture was incubated overnight with aeration at 37° C.

*M. catarrhalis* cells were sonicated and total protein was determined using the BCA assay system (Pierce, Rockford, Ill.). Ten $\mu$g of total protein were mixed with the SDS-PAGE sample buffer containing 0.3M Tris-HCl (pH 8.0), 50% glycerol, 10% SDS, 20% $\beta$-mercaptoethanol and 0.01% bromophenol blue, boiled for 5 minutes and loaded on each lane of SDS-PAGE gel (0.75 mm thick, 7.5% acrylamide). The gels were run at 200 V for 1 hour. Proteins were visualized by staining gels with a solution containing 0.13% Coomassie brilliant blue, 10% acetic acid and 45% methanol. Excess stain was removed with a destaining solution of 5% ethanol and 7.5% acetic acid.

The various Moraxella proteins separated by this procedure are shown in FIGS. 1A and 1B. The *M. catarrhalis* strains tested were as follows:

| Lane | Bacterial Strain | Source |
|------|------------------|--------|
| FIG. 1A | | |
| 1. | Molecular Weight Standards | |
| 2. | *E. coli* | |
| 3. | No sample | |
| 4. | *M. catarrhalis* 4223 | middle ear fluid |
| 5. | *M. catarrhalis* RH408 | non-clumping variant of 4223 |
| 6. | *M. catarrhalis* 5191 | middle ear fluid |
| 7. | *M. catarrhalis* 8185 | nasopharynx |
| 8. | *M. catarrhalis* M2 | sputum |
| 9. | *M. catarrhalis* M5 | sputum |
| 10. | *M. catarrhalis* 25240 | ATCC 25240 |
| FIG. 1B | | |
| 1. | *E. coli* | |
| 2. | No sample | |
| 3. | Molecular Weight Size Markers | |
| 4. | *M. catarrhalis* 4223 | middle ear fluid |
| 5. | *M. catarrhalis* RH408 | non-clumping variant of 4223 |
| 6. | *M. catarrhalis* 3 | sputum |
| 7. | *M. catarrhalis* 56 | sputum |
| 8. | *M. catarrhalis* 135 | middle ear fluid |
| 9. | *M. catarrhalis* 585 | Blood |

The about 200 kDa outer membrane protein was clearly seen in all otitis media strains (*M. catarrhalis* 4223, 5191, 135), in one strain isolated from the nasopharynx (8185), and in one strain isolated from sputum (M2). However, the about 200 kDa protein was not detected in three isolates from sputum (3, 56 and M5) and in one strain with unknown origin (ATCC 25240). A very narrow band was found in an isolate from blood of a bacteremia patient (585) and this band was recognized by an anti-200 kDa specific guinea pig serum on an immunoblot. Strain RH408 is a non-clumping spontaneous mutant isolated from strain 4223 (see Example 1) and was found to not express the about 200 kDa protein.

When gels were run longer, they showed heterogeneity in the apparent molecular masses of the about 200 kDa outer membrane protein in different strains of *M. catarrhalis* (FIG. 2). In FIG. 2 the strains analyzed were as follows:

| Lane | Strain | Source |
|------|--------|--------|
| 1. | Molecular Weight Size Markers | |
| 2. | *M. catarrhalis* H04 | middle ear fluid |
| 3. | *M. catarrhalis* H12 | middle ear fluid |
| 4. | *M. catarrhalis* PO34 | middle ear fluid |
| 5. | *M. catarrhalis* PO51 | middle ear fluid |

| Lane | Strain | Source |
|---|---|---|
| 6. | M. catarrhalis E-07 | middle ear fluid |
| 7. | M. catarrhalis E-22 | middle ear fluid |
| 8. | M. catarrhalis E-23 | middle ear fluid |
| 9. | M. catarrhalis RH 4223 | middle ear fluid |
| 10. | M. catarrhalis RH 408 | Non-clumping variant of 4223 |

The strain H12 (lane 3) was a natural isolate from middle ear fluid, but did not produce the about 200 kDa protein.

There may be at least three different sizes of protein in the about 200 kDa range. However, antibodies raised against the about 200 kDa outer membrane protein from one strain of M. catarrhalis (4223) did recognize all about 200 kDa proteins tested, present in different strains of M. catarrhalis. It is possible, however, that in particular immunogenic compositions, for example, as a vaccine and in particular diagnostic embodiments, that the about 200 kDa outer membrane protein from a variety of M. catarrhalis isolates (including immunogenically diverse isolates) may be required.

Example 3

This Example illustrates the detection of antibodies specific for the about 200 kDa outer membrane protein in a serum obtained from a convalescent patient having recovered from otitis media due to M. catarrhalis.

After separation by SDS-PAGE, bacterial proteins were transferred from polyacrylamide gels to prepared PVDF (polyvinylidene fluoride; Millipore) membranes at a constant voltage of 70 V for 1.5 h in a buffer system consisting of 3 g Tris, 14,4 g glycine and 200 ml methanol per liter at 4° C. Membranes with transferred proteins were blocked with Blocking Reagent (from Boehringer Mannheim) diluted in TBS (0.1M Tris, 0.15M Nacl) at room temperature for 30 min. Blots were exposed to convalescent antiserum diluted 1:500 in Blocking Reagent/TBS with 0.1% Tween 20 for 2 hours at room temperature. This patient had otitis media and the M. catarrhalis strain isolated from the patient's ear fluid was M. catarrhalis CJ7. Blots were then washed 2 times in Blocking Reagent/TBS with Tween at 15 min per wash. The reporter conjugate, horseradish peroxidase (HRP) conjugated to protein G, was diluted 1:4000 with Blocking Reagent/TBS with Tween and used to immerse the washed membranes for 30 min at room temperature. Blots were washed twice as above, followed by a TBS wash. Bound antibodies were detected using the Lumi-Glo (Kirkegaard and Perry) chemiluminescent detection system as described by the manufacturer. Treated blots were exposed to X-ray film. Antibodies were detected in this convalescent serum that reacted with the about 200 kDa outer membrane protein of M. catarrhalis CJ7. These results indicate that the about 200 kDa outer membrane protein is an immunogenic protein of M. catarrhalis to which an immune response is elicited during a natural infection by M. catarrhalis.

Example 4

This Example illustrates the isolation and purification of the about 200 kDa outer membrane protein.

M. catarrhalis 4223 cells were harvested by centrifugation at 2,000 rpm for 10 min and frozen. The frozen cells were thawed, resuspended in 20 mM sodium phosphate buffer (pH 7.2) and sonicated until the cells were disrupted. The frozen-thawed cells were also lysed in 20 mM Tris buffer (pH 8) containing 4% SDS and 0.2 mM EDTA by boiling for 5 min to produce a cell lysate. The cell sonicates and cell lysates were suspended in a SDS-polyacrylamide gel electrophoresis (SDS-PAGE) sample buffer, boiled for 5 min and separated by SDS-PAGE on a gel (1.5 mm thick, 7.5% acrylamide). The estimated position of the about 200 kDa protein on the gel was cut out and the protein extracted from the gel by electroelution using the same buffer as the SDS-PAGE running buffer. The isolated about 200 kDa outer membrane protein was shown to be a homogeneous, single band by SDS-PAGE as seen in FIG. 3. The samples analyzed in FIG. 3 are as follows:

| Lane | Sample |
|---|---|
| 1. | Molecular Weight Size Markers |
| 2. | Isolated and purified 200 kDa outer membrane protein |

The isolated and purified 200 kDa outer membrane protein of M. catarrhalis shown in FIG. 3 has a purity of at least 70%. Purified about 200 kDa outer membrane protein preparations of at least 95% could be readily achieved.

Example 5

This Example illustrates the immunization of guinea pigs with purified about 200 kDa protein from M. catarrhalis.

Approximately 30 to 40 µg of the about 200 kDa protein, which was isolated from M. catarrhalis strain 4223 by electroelution, were mixed with Freund's complete adjuvant (FCA) and subcutaneously injected into guinea pigs. After two weeks, the animals were boosted with about the same amount of the about 200 kDa protein in incomplete Freund's adjuvant (IFA). Two weeks later, blood was collected from the guinea pigs and antisera were obtained.

One antiserum was examined on Western blot for its reactivity with the about 200 kDa protein present in 54 different strains of M. catarrhalis, which were isolated in different geographical locations throughout the world (Canada, U.S. and Finland) (see Table 1 below). The about 200 kDa protein was recognized by the antiserum in all strains, in which the presence of the about 200 kDa protein band was detected on SDS-PAGE gels stained with Coomassie Blue. These results indicate that common epitopes of the about 200 kDa protein were present in all M. catarrhalis strains, which possessed this protein. As stated earlier, this protein is not present in all M. catarrhalis strains, but almost all strains, which were isolated from middle ear fluids from otitis media patients, did possess this protein (Table 1).

Example 6

This Example illustrates the specific recognition of M. catarrhalis strain 4223 with anti-200 kDa protein guinea pig serum by ELISA assay (see Table 2 below).

M. catarrhalis strains 4223, RH408 (200 kDa protein negative mutant) and H-12 were cultured in 60 mL of BHI broth overnight. E. coli strain BL21 (DE3) was cultured in 60 mL of broth overnight. The cultures were split into three tubes and centrifuged. M. catarrhalis strain 4223 was centrifuged at 1,500 rpm for 10 min., H-12 at 2,000 rpm for 10 min., and RH408 and E. coli BL21 (DE3) at 3,000 rpm for 15 min. The pellet in one tube was suspended in 20 ml of Dulbecco's phosphate buffered saline (D-PBS) and diluted to 1/500 with coating buffer (0.05M carbonate/bicarbonate buffer) pH 9.6. One hundred μL of the bacteria suspension were placed in each well and incubated for 1 hour at room temperature. One hundred μL of 0.2% glutaraldehyde was added to each well and incubated at room temperature for 10 min. to fix the cells on the well. The wells were washed with PBS containing 0.1% Tween 20 and 0.1% BSA (washing buffer), and then blocked with PBS containing 0.1% BSA for 30 min. at room temperature. After washing 5 times for 10 seconds with the washing buffer, serial dilutions of guinea pig antiserum with the washing buffer were added to the wells and incubation at room temperature was continued for 60 min. After washing, goat anti-guinea pig IgG conjugated with horseradish peroxidase was added to each well at the dilution of 1/20,000. After incubation at room temperature for 60 minutes, the wells were washed and then color reaction was developed using 3,3-5,5-tetramethylbenzidene (TMB) and hydrogen peroxide.

The ELISA plate wells were also coated with sonicates containing 10 μg/mL of total proteins in the coating buffer, blocked without the fixation process and then assayed as described above.

The results shown in Table 2 indicate that the about 200 kDa outer membrane protein specific guinea pig antiserum specifically recognizes strains of *M. catarrhalis* which produce the about 200 kDa protein. The ability of the antiserum to recognize whole cells indicates that the protein is present on the surface of the bacterial cells.

Example 7

This Example describes the determination of an internal amino acid sequence of the 200 kDa outer membrane protein.

The about 200 kDa outer membrane protein was isolated from *M. catarrhalis* 4223 by electroelution as described above. The protein was subjected to CNBr degradation, the proteolytic digests subjected to SDS-PAGE and transferred onto PVDF membrane. A peptide band migrating at a position corresponding to approximately 40 kDa was cut out from the membrane and its N-terminal amino acid sequence was determined. In another experiment, the CNBr degradation products of the about 200 kDa protein were subjected to a direct determination of N-terminal amino acid sequencing without separating by SDS-PAGE. Both analyses gave an identical, N-terminal sequence of 20 amino acids with one unidentified amino acid at the 17th position. The internal sequence of the 200 kDa outer membrane protein was:

NH$_2$-Asn-Val-Lys-Ser-Val-Ile-Asn-Lys-Glu-Gln-Val-Asn-Asp-Ala-Asn-Lys-X-Gln-Gly-Ile (SEQ ID No: 5).

Example 8

This Example describes the immunization of guinea pigs with a peptide corresponding to an internal fragment of the about 200 kDa outer membrane protein and the analysis of the antiserum generated.

Based upon the determination of the amino acid sequence of an internal fragment of the about 200 kDa outer membrane protein as described above, a 16 amino acid long peptide of sequence:

NH$_2$-Asn-Val-Lys-Ser-Val-Ile-Asn-Lys-Glu-Gln-Val-Asn-Asp-Ala-Asn-Lys (SEQ ID No: 6)

was synthesized using standard procedures. This 16-mer peptide was conjugated to KLH using Imject Maleimide Activated KLH (Pierce, Rockford, Ill.) and approximately 500 μg of the conjugate was injected into guinea pigs using the same immunization and boosting schedule as described above. The guinea pig anti-serum raised against the 16-mer internal amino acid sequence (SEQ ID No: 6) was examined by immunoblot analysis and found to specifically recognize 200 kDa outer membrane protein in cell sonicates of *M. catarrhalis* 4223. The results are shown in FIG. 4 and indicate that the anti-peptide guinea pig antiserum specifically recognizes the 200 kDa protein of *M. catarrhalis* 4223. The samples analyzed in FIG. 4 were as follows:

| Lane | Sample | Antiserum |
|---|---|---|
| 1. | Molecular Weight Markers | |
| 2. | Purified 200 kDa outer membrane protein | Anti-200 kDa protein |
| 3. | *M. catarrhalis* cell sonicate | Anti-peptide 1:5000 |
| 4. | *M. catarrhalis* cell sonicate | Anti-peptide 1:1000 |
| 5. | *M. catarrhalis* cell sonicate | Anti-peptide 1:500 |
| 6. | *M. catarrhalis* cell sonicate | Pre-immune serum |

The results obtained confirm that the peptide corresponding to SEQ ID Nos: 5 and 6 are derived from the 200 kDa outer membrane protein.

Example 9

This Example describes the preparation of a *M. catarrhalis* genomic library.

Chromosomal DNA was isolated as follows:

An *M. catarrhalis* cell pellet was resuspended in 20 mL of Tris-EDTA (TE) buffer, pH 7.5. Pronase (final concentration 500 μg/mL) and SDS (final concentration 1%) were added and the suspension was incubated at 37° C. for 2 hours. DNA was isolated by sequential extractions once with phenol, twice with phenol-chloroform (1:1), and once with chloroform-isoamyl alcohol (24:1). Extracted DNA was dialyzed against 1M NaCl at 4° C. for 4 hours. This was followed by dialysis against TE buffer, pH 7.5, at 4° C. for 48 hours (3 buffer changes). DNA was ethanol precipitated from the dialysate. Large-size DNA was collected by spooling on a glass rod, air dried and dissolved in 3 mL water. Small scale Sau3A (New England BioLabs) restriction digests of chromosomal DNA (final volume 10 μl) were done to establish conditions required to obtain maximal amounts of chromosomal DNA with a size range of 15–23 kb. Large scale digests were prepared once the optimal digestion conditions were determined. The large scale digests consisted of 50 μL of chromosomal DNA (290 μg/mL), 33 μL water, 10 μL Sau3A buffer (New England BioLabs), 1 μL BSA (10 mg/ml, New England BioLabs) and 6.3 μL Sau3A (0.04 U/μL), and were incubated at 37° C. for 15 min. Reactions were stopped by the addition of 10 μL 10X loading buffer (100 mM Tris-HCl pH 8, 10 mM EDTA, 0.1% bromophenol blue, 50% glycerol). Digested DNA was applied to 0.5% agarose gels (prepared in Tris-acetate-EDTA (TAE)) and separated according to size at 50 V for 6 hours. The region of the gel encompassing DNA of size 15–23 kb was cut from the gel and placed in dialysis tubing (BRL) with 3 mL of TAE. DNA was electroeluted from the gel-slice overnight at a field strength of 1 V/cm. Electroeluted DNA in TAE was extracted once with phenol, once with phenol-chloroform (1:1), and precipitated with ethanol. The dried DNA pellet was dissolved in 5 μL water. Size-fractionated chromosomal DNA was ligated with BamHI cut EMBL3 arms (Promega) using T4 DNA ligase in a final volume of 9 μL. The entire ligation reaction was packaged into phage λ using a commercial packaging kit (Amersham) following the manufacturer's protocol.

The packaged DNA library was amplified on solid medium. This was accomplished by incubating 0.1 ml *E. coli* strain NM539 plating cells suspended in 10 mM MgSO$_4$ with 15–25 μL of the packaged DNA library at 37° C. for 15 minutes. Bacteria with adsorbed phage were plated onto BBL plates (10 g BBL trypticase peptone, 5 g NaCl and 15 g agar per liter) using 3 mL of BBL top-agarose (same as BBL plates except agar replaced with 0.6% agarose) and plates were incubated overnight at 37° C. Phage were eluted from the top-agarose by adding 3 mL SM buffer (50 mM Tris-HCl, pH 7.5, 8 mM MgSO$_4$, 100 mM NaCl, 0.01% gelatin) to the plates and leaving them at 4° C. for 7 hours. SM buffer containing phage was collected from the plates, transferred to a screwcap tube and stored at 4° C. over chloroform.

Example 10

This Example describes the cloning of a gene encoding the *M. catarrhalis* 200 kDa outer membrane protein.

The *M. catarrhalis* genomic library in phage lambda EMBL3 was screened using an anti-200 kDa protein guinea pig antiserum. A lambda phage clone 8II, which expressed an about 200 kDa protein, was confirmed by immunoblotting of the phage lysate using the about 200 kDa outer membrane-specific antiserum.

Plate lysate cultures of this recombinant phage were prepared. The DNA was extracted from the plate lysates using a Wizard Lambda Preps DNA Purification System (Promega Corp, Madison, Wis.) according to the manufacturer's instructions. This phage clone carried a DNA insert of about 16 kb in size (the restriction map for which is shown in FIG. 5). The phage DNA was digested with a mixture of the restriction enzymes SalI and XhoI, and separated by agarose gel electrophoresis. Two DNA bands, approximately 5 kb and 11 kb in size, respectively, were cut out from the gel and extracted using a Geneclean kit (BIO 101 Inc., LaJolla, Calif.) according to the manufacturer's direction.

The smaller 5 kb fragment was ligated into a plasmid vector, pBluescript II SK +/− (Stratagene Cloning Systems, LaJolla, Calif.), which had been previously digested with SalI and XhoI, to produce plasmid pKS5. The larger 11 kb fragment was ligated into a plasmid vector, pSP72 (Promega Corp., Madison, Wis.), to produce plasmid pKS9. Both ligated plasmids were used to transform *E. coli*, strain DH5α.

The lambda phage DNA was also digested with a mixture of XhoI and KpnI and the approximately 1.2 kb fragment was isolated after agarose gel separation as described above. This 1.2 kb fragment was ligated into a plasmid vector, pGEM-7Zf(+) (Promega Corp., Madison, Wis.), to produce plasmid pKS47. Restriction maps of the plasmid clones are shown in FIG. 5.

Example 11

This Example describes the sequencing of the gene encoding the about 200 kDa outer membrane protein of *M. catarrhalis*.

The gene encoding the about 200 kDa outer membrane protein was sequenced using an Applied Biosystems sequencer. The one strand of the insert in the plasmid pKS5, was sequenced after construction of a nested set of deletions using a Erase-a-Base system (Promega Corp., Madison, Wis.). The plasmid pKS5 was first digested with XhoI and KpnI, treated with exonuclease III to generate a nested set of deletions in the insert and then recircularized according to the manufacturer's directions. *E. coli* DH5α was transformed with a series of plasmids with deletions generated in this way. Plasmids were isolated from the transformants using a Quiagen midi plasmid isolation kit (Qiagen) and the size of plasmids examined by agarose gel electrophoresis after restriction enzyme digestion. The inserts of the plasmids with deletions were sequenced using a bacteriophage T7 promoter sequence as a primer.

Based upon the sequence, nucleotide primers were synthesized. Using the synthetic nucleotide primers, sequence gaps, which were not sequenced by the Erase-a Base system, were determined.

The sequences of the inserts in plasmids pKS47 and pKS71 were determined from both ends using synthetic nucleotide primers. The nucleotide sequence of the gene has an open reading frame of the gene coding for the about 200 kDa outer membrane protein of *M. catarrhalis* as shown in FIG. 6 (SEQ ID No: 2). This sequence included a nucleotide sequence:

5'- AATGTCAAATCAGTCATTAACAAAGAA-CAAGTAAATGATGCCAATAAAAAGCAAGGCATC-3' (SEQ ID No: 7)

which encodes the internal amino acid sequence of the about 200 kDa outer membrane protein (SEQ ID No: 5) determined above. This result confirms that the cloned gene has an open reading frame of the gene coding for the about 200 kDa outer membrane protein of *M. catarrhalis*. The gene encodes a protein having 1992 amino acids, a calculated molecular weight of 204,677 and a calculated amino acid composition as shown in Table III below. The deduced amino acid sequence of the protein is shown in FIG. 6 (SEQ ID No: 3).

Example 12

This Example describes the identification of the start codon of the gene encoding the about 200 kDa gene of *M. catarrhalis*.

To identify the translation start codon and the promoter region of the 200 kDa protein gene, a plasmid, pKS80, was constructed from pKS5 and pKS47 (FIG. 5). This construct contained about 250 base pairs of DNA upstream from the ATG. The plasmid, pKS5, was digested with KpnI and XhoI. The digest was separated on 0.8% agarose gel and the about 8 kb DNA fragment was cut out from the gel and extracted. Another plasmid, pKS47, was also digested with the two enzymes and the about 1.1 kb DNA fragment was extracted. The 1.1 kb fragment was ligated to the 8 kb fragment to construct pKS80. Western blots using anti-200 kD protein guinea pig serum failed to detect 200 kD protein in the lysates of the transformants carrying pKS80.

Figure 8:
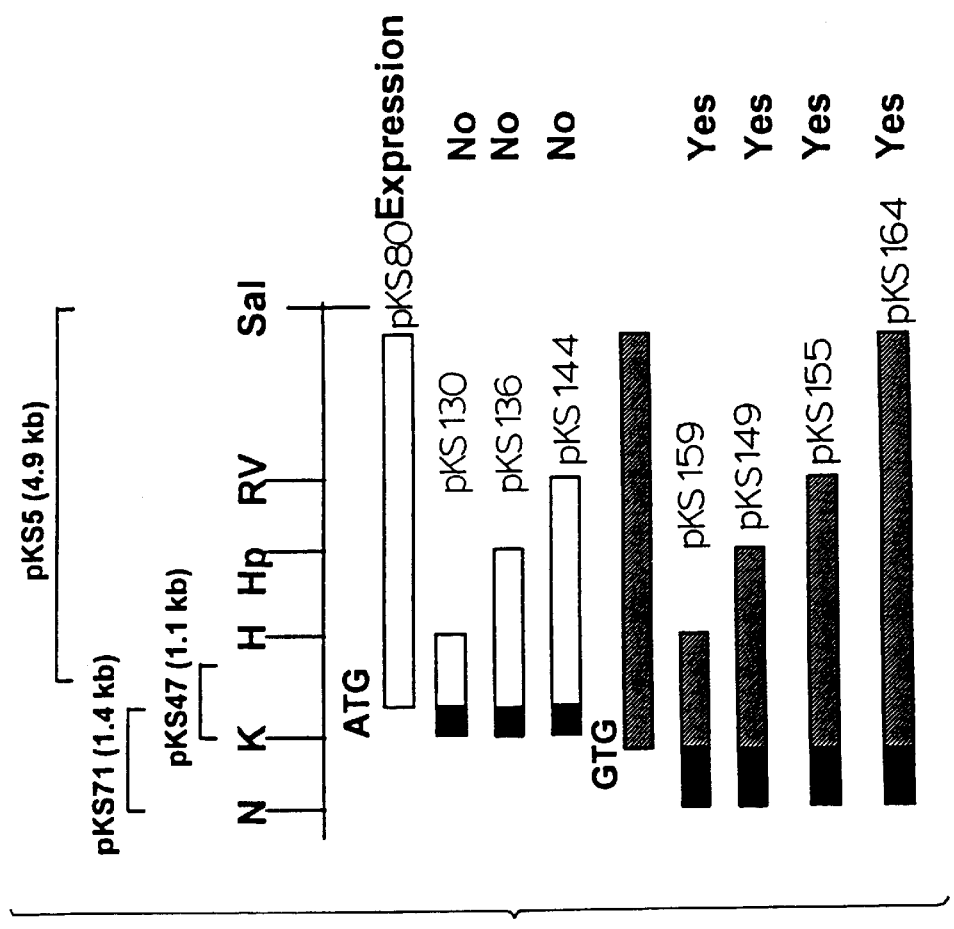
FIG. 8 shows the identification of the GTG initiation codon by expressing the C-terminal truncations of the gene encoding the about 200 kDa outer membrane protein of *M. catarrhalis*. Restriction sites are N: NcoI, K: KpnI, H: HindIII, Hp: HpaI, RV: EcoRV, Sal: SalI.

To examine if the construct was too long to be expressed in *E. coli*, three different sizes of C-terminal truncations were constructed, as shown in FIG. 8. First, the whole insert in pKS80 was cut out by digestion with KpnI and BamHI and then inserted into another vector plasmid, pGEM7Zf(+) (Promega, Madison, Wis.), which had been previously digested with the same two enzymes. The resulting plasmid, pKS105, was further digested with either one of the following enzymes, (1) HindIII, (2) HpaI and SmaI or (3) EcoRV, gel-purified and then recircularized to produce pKS130, pKS136 and pKS144, respectively. Transformants of *E. coli*, DH5α, with either one of pKS130, pKS136 or pKS144 did not produce any truncated proteins, when examined on Western blots using anti-200 kD protein guinea pig serum.

Next, to investigate if the start codon was GTG and if the promoter region was further upstream from the GTG, an about 0.9 kb fragment was cut out from pKS71 using ApaI and KpnI, and ligated into pKS130, pKS136 and pKS144, which had been previously digested with ApaI and KpnI. The 0.9 kb fragment from pKS71 carried the NcoI-KpnI fragment, which contained the possible start codon, GTG, and about 700 bp upstream region from the GTG (FIG. 8). The resulting constructs, pKS159, pKS149 and pKS155, produced truncated proteins, which were recognized by anti-200 kDa protein guinea pig serum on Western blots. The ApaI and KpnI fragment was also ligated to pKS105, which had no C-terminal truncation, to produce pKS164. The transformants carrying pKS164 produced a full-length 200 kDa protein, which was recognized by the same antiserum on Western blot. These results show that the 5'-region of the gene containing the GTG codon and its upstream sequence is necessary for expression of the about 200 kDa protein gene from its own promoter in E. coli, and indicate that a translation start codon of the about 200 kDa protein gene is GTG.

Figure 9:
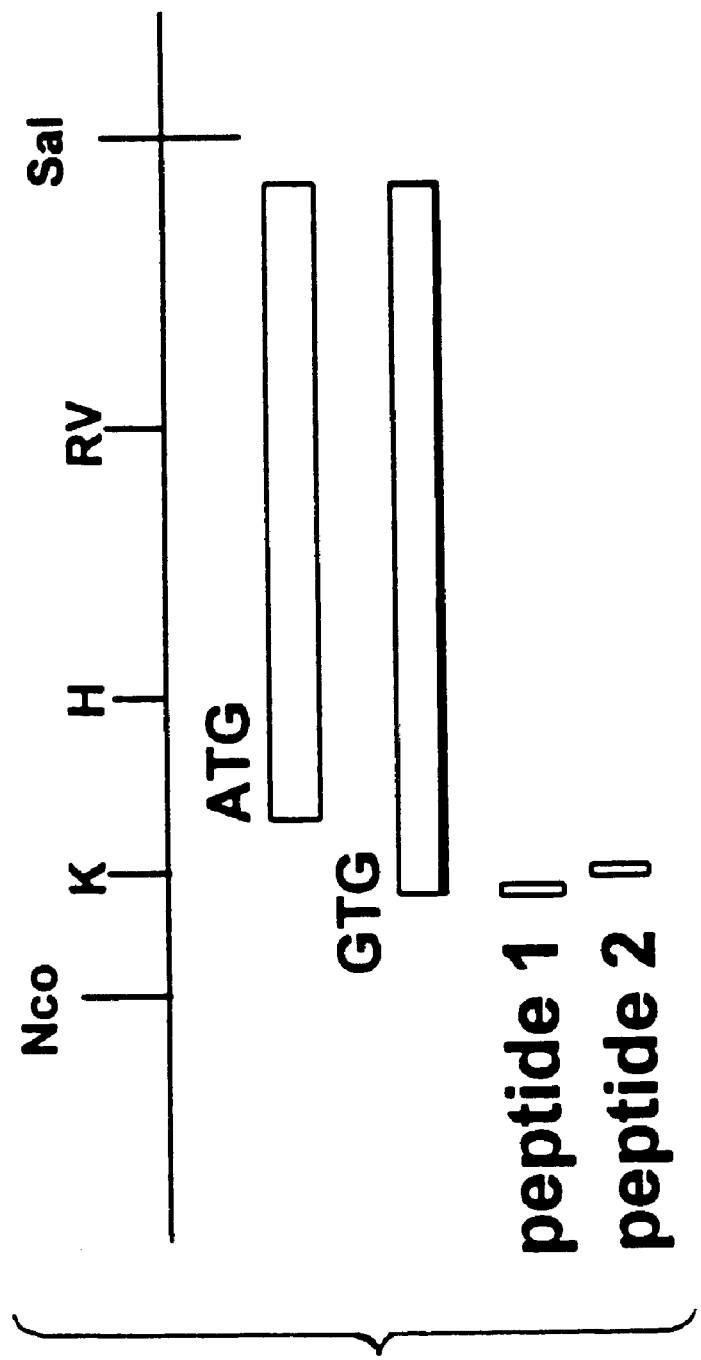
FIG. 9 shows the identification of the GTG initiation codon by utilization of anti-sera specific for N-terminal peptides of the about 200 kDa outer membrane protein of *M. catarrhalis*. Restriction sites are Nco: NcoI, K: KpnI, H: HindIII, RV: EcoRV, Sal: SalI.
Figure 10:
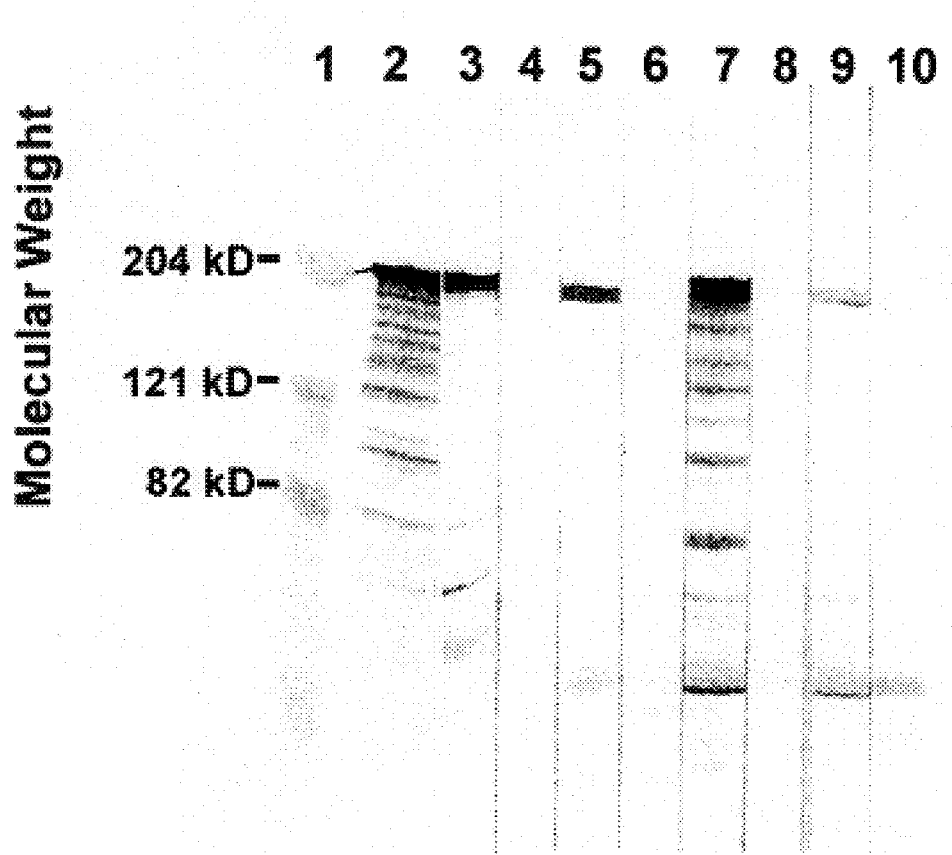
FIG. 10 shows the recognition of 200 kDa protein by anti peptide sera.

To confirm that the start codon of the gene is GTG, two peptides were synthesized, as shown in FIG. 9, according to the deduced amino acid sequence from the nucleotide sequence in FIG. 6. Peptide 1 (SEQ ID No: 9) encompasses the 30 amino acids from the GTG start codon. Peptide 2 (SEQ ID No: 10) is the next 30 amino acid peptide. The peptides are identified in FIG. 6 by underlining. Antisera were raised against these two peptides in guinea pigs and antisera were obtained. As seen in FIG. 10, antisera raised against these two peptides clearly recognized 200 kDa protein from *M. catarrhalis*, strain 4223, by Western blotting. *M. catarrhalis*, strain 4223, was sonicated. Proteins in the sonicate were separated on a SDS-PAGE gel and transferred to PVDF membrane. The membrane was cut into strips and treated with either anti-peptide 1 or anti-peptide 2 guinea pig serum as a first antibody. The second antibody was goat anti-guinea pig IgG conjugated with horse radish peroxidase (Jackson ImmunoResearch Lab. Inc., West Grove, Pa.). The membrane was finally treated with CN/DAB substrate (Pierce, Rockford, Ill.) for color development. Lane 1: prestained molecular weight marker, Lane 2: anti-200 kD protein serum, Lane 3: anti-peptide I serum from guinea pig No. 1, Lane 4: prebleed serum from guinea pig No. 1, Lane 5: anti-peptide 1 serum from guinea pig No. 2, Lane 6: prebleed serum from guinea pig No. 2, Lane 7: anti-peptide 2 serum from guinea pig No. 3, Lane 8: prebleed serum from guinea pig No. 3, Lane 9: anti-peptide 2 serum from guinea pig No. 4, Lane 10: prebleed serum from guinea pig No. 4. The results shown in FIG. 10 indicate that the GTG is the translation start codon of the gene encoding the about 200 kDa protein.

The coding sequence of the about 200 kDa protein gene, which starts at GTG, is 5976 bp and encodes a protein of 1992 amino acids and a calculated molecular weight of 204,677. The position of the 200 kDa protein gene is shown in FIG. 5. The sequence between NcoI and SalI and its amino acid translation are shown in FIG. 6. The calculated amino acid composition of the about 200 kDa protein is shown in Table III.

To construct two different sizes of N-terminal truncation genes under the control of the T7 promoter (as shown in FIG. 11), a ScaI-SalI fragment, which carried the about 1.9 kb 3'-region of the about 200 kDa protein gene, was cut out from pKS5, and the PvuII-SalI fragment, which carried the about 4.8 kb 3'-region, was cut out from pKS80. The two fragments were ligated into a plasmid, pT7—7, previously digested with SmaI and SalI, to produce pKS94 and pKS91, respectively. These ligations resulted in fusions of 1.9 kb and 4.8 kb 3'-regions with seven N-terminal amino acids from the vector. When transformants of an E. coli strain, BL21 (DE3)/pLysS, with either pKS94 or pKS91 were induced with IPTG, they produced a large quantity of N-terminally truncated 200 kDa protein. FIG. 12 shows a Western blot showing the expression of the truncated protein by one of transformants carrying the pKS94 plasmid.

A LacZ fusion of the 3'-5.5 kb fragment of the about 200 kDa protein gene, as shown in FIG. 11. The 5.8 kb fragment, which contained the 3'-5.5 kb region of about 200 kDa protein gene, was excised from pKS80 by digestion with PstI, gel-purified, and then ligated to pGEM5Zf(+) (Promega, Madison, Wis.), previously digested with the same enzyme. The E. coli DH5α clones, which carried the gene in the same direction and reading frame as the LacZ α peptide, were selected by restriction enzyme analyses. These clones constitutively expressed the fusion protein, as shown in FIG. 13.

SUMMARY OF THE DISCLOSURE

In summary of the disclosure, the present invention provides an isolated and purified outer membrane protein of a Moraxella strain, particularly *M. catarrhalis*, having a molecular weight of about 200 kDa as well as isolated and purified DNA molecules encoding the outer membrane protein. The invention also provides analogs, truncations and peptides corresponding to portions of the outer membrane protein. The protein, DNA sequences, recombinant proteins derived therefrom and peptides are useful for diagnosis, immunization and the generation of diagnostic and immunological reagents. Modifications are possible within the scope of this invention.

TABLE I

Presence of the about 200 kDa outer membrane protein in various isolates of *Moraxella catarrhalis*

| Type of Clinical Isolate | Number of isolates Examined | Number of isolates[1] containing the 200 kDa outer membrane protein |
|---|---|---|
| Otitis Media | 37 | 36 |
| Sputum/Expectoration/ Bronchial Secretion | 13 | 6 |
| Blood | 2 | 2 |
| Nasopharynx | 1 | 1 |
| Unknown | 1 | 0 |

[1]The presence of the about 200 kDa outer membrane protein was determined by immunoblot analysis using a monospecific guinea pig anti-200 kDa protein antiserum.

TABLE II

Detection of about 200 kDa outer membrane protein of *M. catarrhalis* by the monospecific anti-200 kDa outer membrane guinea pig antiserum

| Strain | Sample | Reciprocal Reactive Titre |
|---|---|---|
| 4223 | Whole cells not fixed | 800 |
| RH408 | Whole cells not fixed | <200 |
| H12 | Whole cells not fixed | <200 |
| E. coli BL21 | Whole cells not fixed | <200 |
| 4223 | Whole cells fixed | 3200 |
| RH408 | Whole cells fixed | 200 |
| H12 | Whole cells fixed | <200 |
| E. coli BL21 | Whole cells fixed | <200 |
| 4223 | Sonicate | 12,800 |

TABLE II-continued

Detection of about 200 kDa outer membrane protein of *M. catarrhalis* by the monospecific anti-200 kDa outer membrane guinea pig antiserum

| Strain | Sample | Reciprocal Reactive Titre |
|---|---|---|
| RH408 | Sonicate | 800 |
| H12 | Sonicate | 800 |
| *E. coli* BL21 | Sonicate | 200 |

TABLE III

Amino acid composition of the about 200 kDa outer membrane protein of *M. catarrhalis*

| Residue | Number | Percentage (MW) |
|---|---|---|
| N - Asparagine | 196 | 10.9 |
| T - Threonine | 221 | 10.9 |
| K - Lysine | 159 | 10.0 |
| D - Aspartic Acid | 147 | 8.3 |
| A - Alanine | 219 | 7.6 |
| V - Valine | 148 | 7.2 |
| I - Isoleucine | 116 | 6.4 |
| S - Serine | 150 | 6.4 |
| G - Glycine | 222 | 6.2 |
| L - Leucine | 111 | 6.1 |
| Q - Glutamine | 83 | 5.2 |
| E - Glutamic Acid | 55 | 3.5 |
| F - Phenylalanine | 40 | 2.9 |
| R - Arginine | 34 | 2.6 |
| Y - Tyrosine | 27 | 2.2 |
| H - Histidine | 24 | 1.6 |
| P - Proline | 30 | 1.4 |
| M - Methionine | 7 | .4 |
| W - Tryptophan | 3 | .3 |
| B - Aspartic Acid Asparagine | 0 | .0 |
| C - Cysteine | 0 | .0 |

REFERENCES

1. Van Hare, G. F., P. A. Shurin, C. D. Marchant, N. A. Cartelli, C. E. Johnson, D. Fulton, S. Carlin, and C. H. Kim. Acute otitis media caused by *Branhamella catarrhalis*: biology and therapy. Rev. Infect. Dis. 9:16–27.
2. Chapman, A. J., D. M. Musher, S. Jonsson, J. E. Clarridge, and R. J. Wallace. 1985. Development of bactericidal antibody during *Branhamella catarrhalis* infection. J. Infect. Dis. 151:878–882.
3. Hager, H., A. Verghese, S. Alvarez, and S. L. Berk. 1987. *Branhamella catarrhalis* respiratory infections. Rev. Infect. Dis. 9:1140–1149.
4. McLeod, D. T., F. Ahmad, M. J. Croughan, and M. A. Calder. 1986. Bronchopulmonary infection due to *M. catarrhalis*. Clinical features and therapeutic response. Drugs 31(Suppl.3):109–112.
5. Nicotra, B., M. Rivera, J. I. Luman, and R. J. Wallace. 1986. *Branhamella catarrhalis* as a lower respiratory tract pathogen in patients with chronic lung disease. Arch.Intern.Med. 146:890–893.
6. Ninane, G., J. Joly, and M. Kraytman. 1978. Bronchopulmonary infection due to *Branhamella catarrhalis* 11 cases assessed by transtracheal puncture. Br.Med.Jr. 1:276–278.
7. Srinivasan, G., M. J. Raff, W. C. Templeton, S. J. Givens, R. C. Graves, and J. C. Mel. 1981. *Branhamella catarrhalis* pneumonia. Report of two cases and review of the literature. Am.Rev. Respir. Dis. 123:553–555.
8. West, M., S. L. Berk, and J. K. Smith. 1982. *Branhamella catarrhalis* pneumonia. South.Med. J. 75:1021–1023.
9. Brorson, J-E., A. Axelsson, and S. E. Holm. 1976. Studies on *Branhamella catarrhalis* (*Neisseria catarrhalis*) with special reference to maxillary sinusitis. Scan. J. Infect. Dis. 8:151–155.
10. Evans, F. O., Jr., J. B. Sydnor, W. E. C. Moore, G. R. Moore, J. L. Manwaring, A. H. Brill, R. T. Jackson, S. Hanna, J. S. Skaar, L. V. Holdeman, G. S. Fitz-Hugh, M. A. Sande, and J. M. Gwaltney, Jr. 1975. Sinusitis of the maxillary antrum. N.Engl.J.Med. 293:735–739.
11. Tinkelman, D. G., and H. J. Silk. 1989. Clinical and bacteriologic features of chronic sinusitis in children. Am.J.Dis.Child. 143:938–942.
12. Wald, E. R., C. Byers, N. Guerra, M. Casselbrant, and D. Beste. 1989. Subacute sinusitis in children. J.Pediatr. 115:28–32.
13. Wald, E. R., G. J. Milmoe, A. Bowen, J. Ledesma-Medina, N. Salamon, and C. D. Bluestone. 1981. Acute maxillary sinusitis in children. N.Engl.J.Med. 304:749–754.
14. Christensen, J. J., and B. Bruun. 1985. Bacteremia caused by a beta-lactamase producing strain of *Branhamella catarrhalis*. Acta.Pathol. Microbiol. Immunol. Scand. Sect.B 93:273–275.
15. Craig, D. B., and P. A. Wehrle. 1983. *Branhamella catarrhalis* septic arthritis. J. Rheumatol. 10:985–986.
16. Gray, L. D., R. E. Van Scoy, J. P. Anhalt, and P. K. W. Yu. 1989. Wound infection caused by *Branhamella catarrhalis*. J.Clin.Microbiol. 27:818–820.
17. Guthrie, R., K. Bakenhaster, R. Nelson, and R. Woskobnick. 1988. *Branhamella catarrhalis* sepsis: a case report and review of the literature. J.Infect.Dis. 158:907–908.
18. Hiroshi, S., E. J. Anaissie, N. Khardori, and G. P. Bodey. 1988. *Branhamella catarrhalis* septicemia in patients with leukemia. Cancer 61:2315–2317.
19. O'Neill, J. H., and P. W. Mathieson. 1987. Meningitis due to *Branhamella catarrhalis*. Aust. N. Z. J. Med. 17:241–242.
20. Murphy, T. F. 1989. The surface of *Branhamella catarrhalis*: a systematic approach to the surface antigens of an emerging pathogen. Pediatr. Infect. Dis. J. 8:S75–S77.
21. Klingman, K. L., and T. F. Murphy. 1994. Purification and characterization of a high-molecular-weight outer membrane protein of *Moraxella* (*Branhamella*) *catarrhalis*. Infect. Immun. 62:1150–1155.
22. Helminen, M. E., I. Maciver, J. L. Latimer, J. Klesney-Tait, L. D. Cope, M. Paris, G. H. McCracken, Jr., and E. J. Hansen. 1994. A large, antigenically conserved protein on the surface of *Moraxella catarrhalis* is a target for protective antibodies. J. Infect. Dis. 170:867–872.
23. Panezutti H., O. James, E. J. Hanson, Y. Choi, R. E. Harkness, M. H. Klein and P. Chong, 1993. Identification of surface-exposed B-cell epitopes recognized by *Haemophilus influenzae* type b P1 specific monoclonal antibodies. Infec. Immun. 61: 1867–1872.
24. Nixon-George et al. (1990), J. Immunology 144:4798–4802.
25. Wiesmuller (1989), Vaccine 8:29–33.
26. Deres et al. (1989), Nature 342:561.
27. Lockhoff, O. Glycolipids as Immmunomodulators: Synthesis and Properties. 1991. Chem. Int. Ed. Engl. 30:1611–1620.

What we claim is:

1. A purified and isolated nucleic acid molecule having a sequence selected from the group consisting of:
   (a) a DNA sequence as set out in FIG. 6 (SEQ ID No: 2), or the complementary sequence thereto;
   (b) a DNA sequence encoding an about 200 kDa protein of a strain of Moraxella catarrhalis and containing the amino acid sequence NH$_2$-Asn-Val-Lys-Ser-Val-Ile-Asn-Lys-Glu-Gln-Val-Asn-Asp-Ala-Asn-Lys-Lys-Gln-Gly-Ile (SEQ ID No: 8), or the complementary sequence thereto;
   (c) a DNA sequence encoding a deduced amino acid sequence as set out in FIG. 6 (SEQ ID No: 3), or the complementary sequence to the DNA sequence; and
   (d) a nucleotide sequence encoding an about 200 kDa protein of a strain of Moraxella catarrhalis and which hybridizes under stringent conditions to any one of the sequences defined in (a), (b) or (c).

2. The nucleic acid molecule of claim 1, wherein the nucleotide sequence defined in (d) has at least about 90% sequence identity with any one of the sequences defined in (a), (b) or (c).

3. A vector adapted for transformation of a host comprising the nucleic acid molecule of claim 1.

4. An expression vector adapted for transformation of a host comprising the nucleic acid molecule of claim 1 and expression means operatively coupled to the nucleic acid molecule for expression by the host of said outer membrane protein of a strain of Moraxella catarrhalis.

5. The expression of claim 4, wherein the expression means includes a nucleic acid portion encoding a leader sequence for secretion from the host of the outer membrane protein.

6. The expression of claim 4, wherein the expression means includes a nucleic acid portion encoding a lipidation signal for expression from the host of a lipidated form of the outer membrane protein.

7. A transformed host containing an expression vector as claimed in claim 4.

8. A recombinant outer membrane protein producible by the transformed host of claim 7.

9. A live vector for delivery of an outer membrane protein of a strain of Moraxella catarrhalis having a molecular weight of about 200 kDa to a host, comprising a vector containing the nucleic acid molecule of claim 1.

10. The live vector of claim 8, wherein the vector is selected from the group consisting of E. coli, Salmonella, Mycobacteria, adenovirus, poxvirus, vaccinia and poliovirus.

* * * * *

SEQUENCE LISTING

<160> NUMBER OF SEQ ID NOS: 10

<210> SEQ ID NO 1
<211> LENGTH: 6973
<212> TYPE: DNA
<213> ORGANISM: Moraxella catarrhalis
<220> FEATURE:
<221> NAME/KEY: CDS
<222> LOCATION: (708)..(6683)

<400> SEQUENCE: 1

```
ccatggatat gggcaggtgt gctcgcctgc cgtatgatgg cgatgacacc ccatttgccc      60
catatctgta cgatttgaca tgtgatatga tttaacatgt gacatgattt aacattgttt     120
aatactgttg ccatcattac cataatttag taacgcattt agtaacgcat ttgtaaaaat     180
cattgcgccc ctttatgtgt atcatatgaa tagaatatta tgattgtatc tgattattgt     240
atcagaatgg tgatgctata tgatgatgcc tacgagttga tttgggttaa tcactctatg     300
atttgatata ttttgaaact aatctattga cttaaatcac catatggtta taatttagca     360
taatggtagg cttttttgtaa aaatcacatc gcaatattgt tctactgtta ctaccatgct    420
tgaatgacga tcccaatcac cagattcatt caagtgatgt gtttgtatac gcaccattta     480
ccctaattat ttcaatcaaa tgcctatgtc agcatgtatc atttttttaa ggtaaaccac     540
catgaatcac atctataaag tcatctttaa caaagccaca ggcacattta tggcagtggc     600
agagtacgcc aaatcccaca gcacgggggg ggggtagctg tgctacaggg caagttggca     660
gtgtatgcac tctgagcttt gcccgtattg ccgcgctcgc tgtcctc gtg atc ggt       716
                                                    Met Ile Gly
                                                    1 gca acg ctc agt ggc agt gct tat gct caa aaa aaa gat acc aaa cat      764
Ala Thr Leu Ser Gly Ser Ala Tyr Ala Gln Lys Lys Asp Thr Lys His
    5                  10                  15 atc gca att ggt gaa caa aac cag cca aga cgc tca ggc act gcc aag      812
Ile Ala Ile Gly Glu Gln Asn Gln Pro Arg Arg Ser Gly Thr Ala Lys
 20                  25                  30                  35 gcg gac ggt gat cga gcc att gct att ggt gaa aat gct aac gca cag      860
Ala Asp Gly Asp Arg Ala Ile Ala Ile Gly Glu Asn Ala Asn Ala Gln
                40                  45                  50 ggc ggt caa gcc atc gcc atc ggt agt agt aat aaa act gtc aat gga      908
Gly Gly Gln Ala Ile Ala Ile Gly Ser Ser Asn Lys Thr Val Asn Gly
            55                  60                  65 agc agt ttg gat aag ata ggt acc gat gct acg ggt caa gag tcc atc      956
Ser Ser Leu Asp Lys Ile Gly Thr Asp Ala Thr Gly Gln Glu Ser Ile
        70                  75                  80 gcc atc ggt ggt gat gta aag gct agt ggt gat gcc tcg att gcc atc     1004
Ala Ile Gly Gly Asp Val Lys Ala Ser Gly Asp Ala Ser Ile Ala Ile
    85                  90                  95 ggt agt gat gac tta cat ttg ctt gat cag cat ggt aat cct aaa cat     1052
Gly Ser Asp Asp Leu His Leu Leu Asp Gln His Gly Asn Pro Lys His
100                 105                 110                 115 ccg aaa ggt act ctg att aac gat ctt att aac ggc cat gca gta tta     1100
Pro Lys Gly Thr Leu Ile Asn Asp Leu Ile Asn Gly His Ala Val Leu
                120                 125                 130 aaa gaa ata cga agc tca aag gat aat gat gta aaa tat aga cgc aca     1148
Lys Glu Ile Arg Ser Ser Lys Asp Asn Asp Val Lys Tyr Arg Arg Thr
            135                 140                 145 acc gca agc gga cac gcc agt act gca gtg gga gcc atg tca tat gca     1196
Thr Ala Ser Gly His Ala Ser Thr Ala Val Gly Ala Met Ser Tyr Ala
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 150 |     |     |     |     | 155 |     |     |     |     |     | 160 |     |     |      |
| cag | ggt | cat | ttt | tcc | aac | gcc | ttt | ggt | aca | cgg | gca | aca | gct | aaa | agt | 1244 |
| Gln | Gly | His | Phe | Ser | Asn | Ala | Phe | Gly | Thr | Arg | Ala | Thr | Ala | Lys | Ser |      |
|     |     | 165 |     |     |     |     | 170 |     |     |     |     |     | 175 |     |     |      |
| gcc | tat | tcc | ttg | gca | gtg | ggt | ctt | gcc | gcc | aca | gcc | gag | ggc | caa | tct | 1292 |
| Ala | Tyr | Ser | Leu | Ala | Val | Gly | Leu | Ala | Ala | Thr | Ala | Glu | Gly | Gln | Ser |      |
| 180 |     |     |     |     | 185 |     |     |     |     | 190 |     |     |     |     | 195 |      |
| aca | atc | gct | att | ggt | tct | gat | gca | aca | tct | agc | tcg | ttg | gga | gcg | ata | 1340 |
| Thr | Ile | Ala | Ile | Gly | Ser | Asp | Ala | Thr | Ser | Ser | Ser | Leu | Gly | Ala | Ile |      |
|     |     |     |     | 200 |     |     |     |     | 205 |     |     |     |     | 210 |     |      |
| gcc | ctt | ggt | gca | ggt | act | cgt | gct | cag | cta | cag | ggc | agt | att | gcc | cta | 1388 |
| Ala | Leu | Gly | Ala | Gly | Thr | Arg | Ala | Gln | Leu | Gln | Gly | Ser | Ile | Ala | Leu |      |
|     |     |     |     | 215 |     |     |     |     | 220 |     |     |     |     | 225 |     |      |
| ggt | caa | ggt | tct | gtt | gtc | act | cag | agt | gat | aat | aat | tct | aga | ccg | gcc | 1436 |
| Gly | Gln | Gly | Ser | Val | Val | Thr | Gln | Ser | Asp | Asn | Asn | Ser | Arg | Pro | Ala |      |
|     |     | 230 |     |     |     |     | 235 |     |     |     |     |     | 240 |     |     |      |
| tat | aca | cca | aat | acc | cag | gca | cta | gac | ccc | aag | ttt | caa | gcc | acc | aat | 1484 |
| Tyr | Thr | Pro | Asn | Thr | Gln | Ala | Leu | Asp | Pro | Lys | Phe | Gln | Ala | Thr | Asn |      |
|     |     | 245 |     |     |     |     | 250 |     |     |     |     |     | 255 |     |     |      |
| aat | acg | aag | gcg | ggt | cca | ctt | tcc | att | ggt | agt | aac | tct | atc | aaa | cgt | 1532 |
| Asn | Thr | Lys | Ala | Gly | Pro | Leu | Ser | Ile | Gly | Ser | Asn | Ser | Ile | Lys | Arg |      |
| 260 |     |     |     |     | 265 |     |     |     |     | 270 |     |     |     |     | 275 |      |
| aaa | atc | atc | aat | gtc | ggt | gca | ggt | gtt | aat | aaa | acc | gat | gcg | gtc | aat | 1580 |
| Lys | Ile | Ile | Asn | Val | Gly | Ala | Gly | Val | Asn | Lys | Thr | Asp | Ala | Val | Asn |      |
|     |     |     |     | 280 |     |     |     |     | 285 |     |     |     |     | 290 |     |      |
| gtg | gca | cag | cta | gaa | gcg | gtg | gtg | aag | tgg | gct | aag | gag | cgt | aga | att | 1628 |
| Val | Ala | Gln | Leu | Glu | Ala | Val | Val | Lys | Trp | Ala | Lys | Glu | Arg | Arg | Ile |      |
|     |     |     |     | 295 |     |     |     |     | 300 |     |     |     |     | 305 |     |      |
| act | ttt | cag | ggt | gat | gat | aac | agt | act | gac | gta | aaa | ata | ggt | ttg | gat | 1676 |
| Thr | Phe | Gln | Gly | Asp | Asp | Asn | Ser | Thr | Asp | Val | Lys | Ile | Gly | Leu | Asp |      |
|     |     |     |     | 310 |     |     |     |     | 315 |     |     |     |     | 320 |     |      |
| aat | act | tta | act | att | aaa | ggt | ggt | gca | gag | acc | aac | gca | tta | acc | gat | 1724 |
| Asn | Thr | Leu | Thr | Ile | Lys | Gly | Gly | Ala | Glu | Thr | Asn | Ala | Leu | Thr | Asp |      |
|     |     |     |     | 325 |     |     |     |     | 330 |     |     |     |     | 335 |     |      |
| aat | aat | atc | ggt | gtg | gta | aaa | gag | gct | gat | aat | agt | ggt | ctg | aaa | gtt | 1772 |
| Asn | Asn | Ile | Gly | Val | Val | Lys | Glu | Ala | Asp | Asn | Ser | Gly | Leu | Lys | Val |      |
| 340 |     |     |     |     | 345 |     |     |     |     | 350 |     |     |     |     | 355 |      |
| aaa | ctt | gct | aaa | act | tta | aac | aat | ctt | act | gag | gtg | aat | aca | act | aca | 1820 |
| Lys | Leu | Ala | Lys | Thr | Leu | Asn | Asn | Leu | Thr | Glu | Val | Asn | Thr | Thr | Thr |      |
|     |     |     |     | 360 |     |     |     |     | 365 |     |     |     |     | 370 |     |      |
| tta | aat | gcc | aca | acc | aca | gtt | aag | gta | ggt | agt | agt | agt | act | aca |     | 1868 |
| Leu | Asn | Ala | Thr | Thr | Thr | Val | Lys | Val | Gly | Ser | Ser | Ser | Thr | Thr |     |      |
|     |     |     | 375 |     |     |     |     | 380 |     |     |     |     | 385 |     |     |      |
| gct | gaa | tta | ttg | agt | gat | agt | tta | acc | ttt | acc | cag | ccc | aat | aca | ggc | 1916 |
| Ala | Glu | Leu | Leu | Ser | Asp | Ser | Leu | Thr | Phe | Thr | Gln | Pro | Asn | Thr | Gly |      |
|     |     |     | 390 |     |     |     |     | 395 |     |     |     |     | 400 |     |     |      |
| agt | caa | agc | aca | agc | aaa | acc | gtc | tat | ggc | gtt | aat | ggg | gtg | aag | ttt | 1964 |
| Ser | Gln | Ser | Thr | Ser | Lys | Thr | Val | Tyr | Gly | Val | Asn | Gly | Val | Lys | Phe |      |
|     |     | 405 |     |     |     |     | 410 |     |     |     |     |     | 415 |     |     |      |
| act | aat | aat | gca | gaa | aca | aca | gca | gca | atc | ggc | act | act | cgt | att | acc | 2012 |
| Thr | Asn | Asn | Ala | Glu | Thr | Thr | Ala | Ala | Ile | Gly | Thr | Thr | Arg | Ile | Thr |      |
| 420 |     |     |     |     | 425 |     |     |     |     | 430 |     |     |     |     | 435 |      |
| aga | gat | aaa | att | ggc | ttt | gct | cga | gat | ggt | gat | gtt | gat | gaa | aaa | caa | 2060 |
| Arg | Asp | Lys | Ile | Gly | Phe | Ala | Arg | Asp | Gly | Asp | Val | Asp | Glu | Lys | Gln |      |
|     |     |     |     | 440 |     |     |     |     | 445 |     |     |     |     | 450 |     |      |
| gca | cca | tat | ttg | gat | aaa | aaa | caa | ctt | aaa | gtg | ggt | agt | gtt | gca | att | 2108 |
| Ala | Pro | Tyr | Leu | Asp | Lys | Lys | Gln | Leu | Lys | Val | Gly | Ser | Val | Ala | Ile |      |
|     |     |     | 455 |     |     |     |     | 460 |     |     |     |     | 465 |     |     |      |
| acc | ata | gac | aat | ggc | att | gat | gca | ggt | aat | aaa | aag | atc | agt | aat | ctt | 2156 |

```
                Thr Ile Asp Asn Gly Ile Asp Ala Gly Asn Lys Lys Ile Ser Asn Leu
                                470                 475                 480 gcc aaa ggt agc agt gct aac gat gcg gtt acc atc gaa cag ctc aaa            2204
Ala Lys Gly Ser Ser Ala Asn Asp Ala Val Thr Ile Glu Gln Leu Lys
485                 490                 495 gcc gcc aag cct act tta aac gca ggc gct ggc atc agt gtc aca cct            2252
Ala Ala Lys Pro Thr Leu Asn Ala Gly Ala Gly Ile Ser Val Thr Pro
500                 505                 510                 515 act gaa ata tca gtt gat gct aag agt ggc aat gtt acc gcc cca act            2300
Thr Glu Ile Ser Val Asp Ala Lys Ser Gly Asn Val Thr Ala Pro Thr
                520                 525                 530 tac aac att ggc gtg aaa acc acc gag ctt aac agt gat ggc act agt            2348
Tyr Asn Ile Gly Val Lys Thr Thr Glu Leu Asn Ser Asp Gly Thr Ser
                535                 540                 545 gat aaa ttt agt gtt aag ggt agt ggt acg aac aat agc tta gtt acc            2396
Asp Lys Phe Ser Val Lys Gly Ser Gly Thr Asn Asn Ser Leu Val Thr
550                 555                 560 gcc gaa cat ttg gca agc tat cta aat gaa gtc aat cga acg gct gac            2444
Ala Glu His Leu Ala Ser Tyr Leu Asn Glu Val Asn Arg Thr Ala Asp
565                 570                 575 agt gct cta caa agc ttt acc gtt aaa gaa gaa gac gat gat gac gcc            2492
Ser Ala Leu Gln Ser Phe Thr Val Lys Glu Glu Asp Asp Asp Asp Ala
580                 585                 590                 595 aac gct atc acc gtg gct aaa gat acg aca aaa aat gcc ggc gca gtc            2540
Asn Ala Ile Thr Val Ala Lys Asp Thr Thr Lys Asn Ala Gly Ala Val
                600                 605                 610 agc atc tta aaa ctc aaa ggt aaa aac ggt cta acg gtt gct acc aaa            2588
Ser Ile Leu Lys Leu Lys Gly Lys Asn Gly Leu Thr Val Ala Thr Lys
                615                 620                 625 aaa gat ggt acg gtt acc ttt ggg ctt agc caa gat agc ggt ctg acc            2636
Lys Asp Gly Thr Val Thr Phe Gly Leu Ser Gln Asp Ser Gly Leu Thr
                630                 635                 640 att ggc aaa agc acc cta aac aac gat ggc ttg act gtt aaa gat acc            2684
Ile Gly Lys Ser Thr Leu Asn Asn Asp Gly Leu Thr Val Lys Asp Thr
645                 650                 655 aac gaa caa atc caa gtc ggt gct aat ggc att aaa ttt act aat gtg            2732
Asn Glu Gln Ile Gln Val Gly Ala Asn Gly Ile Lys Phe Thr Asn Val
660                 665                 670                 675 aat ggt agt aat cca ggt act ggc att gca aat acc gct cgc att acc            2780
Asn Gly Ser Asn Pro Gly Thr Gly Ile Ala Asn Thr Ala Arg Ile Thr
                680                 685                 690 aga gat aaa att ggc ttt gct ggt tct gat ggt gca gtt gat aca aac            2828
Arg Asp Lys Ile Gly Phe Ala Gly Ser Asp Gly Ala Val Asp Thr Asn
                695                 700                 705 aaa cct tat ctt gat caa gac aag cta caa gtt ggc aat gtt aag att            2876
Lys Pro Tyr Leu Asp Gln Asp Lys Leu Gln Val Gly Asn Val Lys Ile
                710                 715                 720 acc aac act ggc att aac gca ggt ggt aaa gcc atc aca ggg ctg tcc            2924
Thr Asn Thr Gly Ile Asn Ala Gly Gly Lys Ala Ile Thr Gly Leu Ser
                725                 730                 735 cca aca ctg cct agc att gcc gat caa agt agc cgc aac ata gaa ctg            2972
Pro Thr Leu Pro Ser Ile Ala Asp Gln Ser Ser Arg Asn Ile Glu Leu
740                 745                 750                 755 ggc aat aca atc caa gac aaa gac aaa tcc aac gct gcc agc att aat            3020
Gly Asn Thr Ile Gln Asp Lys Asp Lys Ser Asn Ala Ala Ser Ile Asn
                760                 765                 770 gat ata tta aat aca ggc ttt aac cta aaa aat aat aac aac ccc att            3068
Asp Ile Leu Asn Thr Gly Phe Asn Leu Lys Asn Asn Asn Asn Pro Ile
                775                 780                 785
```

```
gac ttt gtc tcc act tat gac att gtt gac ttt gcc aat ggc aat gcc   3116
Asp Phe Val Ser Thr Tyr Asp Ile Val Asp Phe Ala Asn Gly Asn Ala
        790                 795                 800 acc acc gcc aca gta acc cat gat acc gct aac aaa acc agt aaa gtg   3164
Thr Thr Ala Thr Val Thr His Asp Thr Ala Asn Lys Thr Ser Lys Val
    805                 810                 815 gta tat gat gtg aat gtg gat gat aca acc att cat cta aca ggc act   3212
Val Tyr Asp Val Asn Val Asp Asp Thr Thr Ile His Leu Thr Gly Thr
820                 825                 830                 835 gat gac aat aaa aaa ctt ggc gtc aaa acc acc aaa ctg aac aaa aca   3260
Asp Asp Asn Lys Lys Leu Gly Val Lys Thr Thr Lys Leu Asn Lys Thr
            840                 845                 850 agt gct aat ggt aat aca gca act aac ttt aat gtt aac tct agt gat   3308
Ser Ala Asn Gly Asn Thr Ala Thr Asn Phe Asn Val Asn Ser Ser Asp
        855                 860                 865 gaa gat gcc ctt gtt aac gcc aaa gac atc gcc gaa aat cta aac acc   3356
Glu Asp Ala Leu Val Asn Ala Lys Asp Ile Ala Glu Asn Leu Asn Thr
    870                 875                 880 cta gcc aag gaa att cac acc acc aaa ggc aca gca gac acc gcc cta   3404
Leu Ala Lys Glu Ile His Thr Thr Lys Gly Thr Ala Asp Thr Ala Leu
885                 890                 895 caa acc ttt acc gtt aaa aag gta gat gaa aat aat aat gct gat gac   3452
Gln Thr Phe Thr Val Lys Lys Val Asp Glu Asn Asn Asn Ala Asp Asp
900                 905                 910                 915 gcc aac gcc atc acc gtg ggt caa aag aac gca aat aat caa gtc aac   3500
Ala Asn Ala Ile Thr Val Gly Gln Lys Asn Ala Asn Asn Gln Val Asn
            920                 925                 930 acc cta aca ctc aaa ggt gaa aac ggt ctt aat att aaa acc gac aaa   3548
Thr Leu Thr Leu Lys Gly Glu Asn Gly Leu Asn Ile Lys Thr Asp Lys
        935                 940                 945 aat ggt acg gtt acc ttt ggc att aac acc aca agc ggt ctt aaa gcc   3596
Asn Gly Thr Val Thr Phe Gly Ile Asn Thr Thr Ser Gly Leu Lys Ala
    950                 955                 960 ggc aaa agc acc cta aac gac ggt ggc ttg tct att aaa aac ccc act   3644
Gly Lys Ser Thr Leu Asn Asp Gly Gly Leu Ser Ile Lys Asn Pro Thr
965                 970                 975 ggt agc gaa caa atc caa gtc ggt gct gat ggc gtg aag ttt gcc aag   3692
Gly Ser Glu Gln Ile Gln Val Gly Ala Asp Gly Val Lys Phe Ala Lys
980                 985                 990                 995 gtt aat aat aat ggt gtt gta ggt gct ggc att gat ggc aca act cgc   3740
Val Asn Asn Asn Gly Val Val Gly Ala Gly Ile Asp Gly Thr Thr Arg
            1000                1005                1010 att acc aga gat gaa att ggc ttt act ggg act aat ggc tca ctt gat   3788
Ile Thr Arg Asp Glu Ile Gly Phe Thr Gly Thr Asn Gly Ser Leu Asp
        1015                1020                1025 aaa agc aaa ccc cac cta agc aaa gac ggc att aac gca ggt ggt aaa   3836
Lys Ser Lys Pro His Leu Ser Lys Asp Gly Ile Asn Ala Gly Gly Lys
    1030                1035                1040 aag att acc aac att caa tca ggt gag att gcc caa aac agc cat gat   3884
Lys Ile Thr Asn Ile Gln Ser Gly Glu Ile Ala Gln Asn Ser His Asp
1045                1050                1055 gct gtg aca ggc ggc aag att tat gat tta aaa acc gaa ctt gaa aac   3932
Ala Val Thr Gly Gly Lys Ile Tyr Asp Leu Lys Thr Glu Leu Glu Asn
1060                1065                1070                1075 aaa atc agc agt act gcc aaa aca gca caa aac tca tta cac gaa ttc   3980
Lys Ile Ser Ser Thr Ala Lys Thr Ala Gln Asn Ser Leu His Glu Phe
            1080                1085                1090 tca gta gca gat gaa caa ggt aat aac ttt acg gtt agt aac cct tac   4028
Ser Val Ala Asp Glu Gln Gly Asn Asn Phe Thr Val Ser Asn Pro Tyr
        1095                1100                1105
```

```
tcc agt tat gac acc tca aag acc tct gat gtc atc acc ttt gca ggt      4076
Ser Ser Tyr Asp Thr Ser Lys Thr Ser Asp Val Ile Thr Phe Ala Gly
        1110                1115                1120 gaa aac ggc att acc acc aag gta aat aaa ggt gtg gtg cgt gtg ggc      4124
Glu Asn Gly Ile Thr Thr Lys Val Asn Lys Gly Val Val Arg Val Gly
    1125                1130                1135 att gac caa acc aaa ggc tta acc acg cct aag ctg acc gtg ggt aat      4172
Ile Asp Gln Thr Lys Gly Leu Thr Thr Pro Lys Leu Thr Val Gly Asn
1140                1145                1150                1155 aat aat ggc aaa ggc att gtc att gac agc caa aat ggt caa aat acc      4220
Asn Asn Gly Lys Gly Ile Val Ile Asp Ser Gln Asn Gly Gln Asn Thr
            1160                1165                1170 atc aca gga cta agc aac act cta gct aat gtt acc aat gat aaa ggt      4268
Ile Thr Gly Leu Ser Asn Thr Leu Ala Asn Val Thr Asn Asp Lys Gly
                1175                1180                1185 agc gta cgc acc aca gaa cag ggc aat ata atc aaa gac gaa gac aaa      4316
Ser Val Arg Thr Thr Glu Gln Gly Asn Ile Ile Lys Asp Glu Asp Lys
        1190                1195                1200 acc cgt gcc gcc agc att gtt gat gtg cta agc gca ggc ttt aac ttg      4364
Thr Arg Ala Ala Ser Ile Val Asp Val Leu Ser Ala Gly Phe Asn Leu
    1205                1210                1215 caa ggc aat ggt gaa gcg gtt gac ttt gtc tcc act tat gac acc gtc      4412
Gln Gly Asn Gly Glu Ala Val Asp Phe Val Ser Thr Tyr Asp Thr Val
1220                1225                1230                1235 aac ttt gcc gat ggc aat gcc acc acc gct aag gtg acc tat gat gac      4460
Asn Phe Ala Asp Gly Asn Ala Thr Thr Ala Lys Val Thr Tyr Asp Asp
            1240                1245                1250 aca agc aaa acc agt aaa gtg gtc tat gat gtc aat gtg gat gat aca      4508
Thr Ser Lys Thr Ser Lys Val Val Tyr Asp Val Asn Val Asp Asp Thr
                1255                1260                1265 acc att gaa gtt aaa gat aaa aaa ctt ggc gta aaa acc acc aca ttg      4556
Thr Ile Glu Val Lys Asp Lys Lys Leu Gly Val Lys Thr Thr Thr Leu
        1270                1275                1280 acc agt act ggc aca ggt gct aat aaa ttt gcc cta agc aat caa gct      4604
Thr Ser Thr Gly Thr Gly Ala Asn Lys Phe Ala Leu Ser Asn Gln Ala
    1285                1290                1295 act ggc gat gcg ctt gtc aag gcc agt gat atc gtt gct cat cta aac      4652
Thr Gly Asp Ala Leu Val Lys Ala Ser Asp Ile Val Ala His Leu Asn
1300                1305                1310                1315 acc tta tct ggc gac atc caa act gcc aaa ggg gca agc caa gcg aac      4700
Thr Leu Ser Gly Asp Ile Gln Thr Ala Lys Gly Ala Ser Gln Ala Asn
            1320                1325                1330 aac tca gca ggc tat gtg gat gct gat ggc aat aag gtc atc tat gac      4748
Asn Ser Ala Gly Tyr Val Asp Ala Asp Gly Asn Lys Val Ile Tyr Asp
                1335                1340                1345 agt acc gat aac aag tac tat caa gcc aaa aat gat ggc aca gtt gat      4796
Ser Thr Asp Asn Lys Tyr Tyr Gln Ala Lys Asn Asp Gly Thr Val Asp
        1350                1355                1360 aaa acc aaa gaa gtt gcc aaa gac aaa ctg gtc gcc caa gcc caa acc      4844
Lys Thr Lys Glu Val Ala Lys Asp Lys Leu Val Ala Gln Ala Gln Thr
    1365                1370                1375 cca gat ggc aca ttg gct caa atg aat gtc aaa tca gtc att aac aaa      4892
Pro Asp Gly Thr Leu Ala Gln Met Asn Val Lys Ser Val Ile Asn Lys
1380                1385                1390                1395 gaa caa gta aat gat gcc aat aaa aag caa ggc atc aat gaa gac aac      4940
Glu Gln Val Asn Asp Ala Asn Lys Lys Gln Gly Ile Asn Glu Asp Asn
            1400                1405                1410 gcc ttt gtt aaa gga ctt gaa aaa gcc gct tct gat aac aaa acc aaa      4988
Ala Phe Val Lys Gly Leu Glu Lys Ala Ala Ser Asp Asn Lys Thr Lys
```

-continued

|  |  |  |
|---|---|---|
| 1415 | 1420 | 1425 |

```
aac gcc gca gta act gtg ggt gat tta aat gcc gtt gcc caa aca ccg     5036
Asn Ala Ala Val Thr Val Gly Asp Leu Asn Ala Val Ala Gln Thr Pro
        1430                1435                1440 ctg acc ttt gca ggg gat aca ggc aca acg gct aaa aaa ctg ggc gag     5084
Leu Thr Phe Ala Gly Asp Thr Gly Thr Thr Ala Lys Lys Leu Gly Glu
    1445                1450                1455 act ttg acc atc aaa ggt ggg caa aca gac acc aat aag cta acc gat     5132
Thr Leu Thr Ile Lys Gly Gly Gln Thr Asp Thr Asn Lys Leu Thr Asp
1460                1465                1470                1475 aat aac atc ggt gtg gta gca ggt act gat ggc ttc act gtc aaa ctt     5180
Asn Asn Ile Gly Val Val Ala Gly Thr Asp Gly Phe Thr Val Lys Leu
            1480                1485                1490 gcc aaa gac cta acc aat ctt aac agc gtt aat gca ggt ggc acc aaa     5228
Ala Lys Asp Leu Thr Asn Leu Asn Ser Val Asn Ala Gly Gly Thr Lys
        1495                1500                1505 att gat gac aaa ggc gtg tct ttt gta gac tca agc ggt caa gcc aaa     5276
Ile Asp Asp Lys Gly Val Ser Phe Val Asp Ser Ser Gly Gln Ala Lys
    1510                1515                1520 gca aac acc cct gtg cta agt gcc aat ggg ctg gac ctg ggt ggc aag     5324
Ala Asn Thr Pro Val Leu Ser Ala Asn Gly Leu Asp Leu Gly Gly Lys
1525                1530                1535 gtc atc agt aat gtg ggc aaa ggc aca aaa gat acc gac gct gcc aat     5372
Val Ile Ser Asn Val Gly Lys Gly Thr Lys Asp Thr Asp Ala Ala Asn
1540                1545                1550                1555 gta caa cag tta aac gaa gta cgc aac ttg ttg ggt ctt ggt aat gct     5420
Val Gln Gln Leu Asn Glu Val Arg Asn Leu Leu Gly Leu Gly Asn Ala
            1560                1565                1570 ggt aat gat aac gct gac ggc aat cag gta aac att gcc gac atc aaa     5468
Gly Asn Asp Asn Ala Asp Gly Asn Gln Val Asn Ile Ala Asp Ile Lys
        1575                1580                1585 aaa gac cca aat tca ggt tca tca tct aac cgc act gtc atc aaa gca     5516
Lys Asp Pro Asn Ser Gly Ser Ser Ser Asn Arg Thr Val Ile Lys Ala
    1590                1595                1600 ggc acg gta ctt ggc ggt aaa ggt aat aac gat acc gaa aaa ctt gcc     5564
Gly Thr Val Leu Gly Gly Lys Gly Asn Asn Asp Thr Glu Lys Leu Ala
1605                1610                1615 act ggt ggt ata caa gtg ggc gtg gat aaa gac ggc aac gct aac ggc     5612
Thr Gly Gly Ile Gln Val Gly Val Asp Lys Asp Gly Asn Ala Asn Gly
1620                1625                1630                1635 gat tta agc aat gtt tgg gtc aaa acc caa aaa gat ggc agc aaa aaa     5660
Asp Leu Ser Asn Val Trp Val Lys Thr Gln Lys Asp Gly Ser Lys Lys
            1640                1645                1650 gcc ctg ctc gcc act tat aac gcc gca ggt cag acc aac tat ttg acc     5708
Ala Leu Leu Ala Thr Tyr Asn Ala Ala Gly Gln Thr Asn Tyr Leu Thr
        1655                1660                1665 aac aac ccc gca gaa gcc att gac aga ata aat gaa caa ggt atc cgc     5756
Asn Asn Pro Ala Glu Ala Ile Asp Arg Ile Asn Glu Gln Gly Ile Arg
    1670                1675                1680 ttc ttc cat gtc aac gat ggc aat caa gag cct gtg gta caa ggg cgt     5804
Phe Phe His Val Asn Asp Gly Asn Gln Glu Pro Val Val Gln Gly Arg
1685                1690                1695 aac ggc att gac tca agt gcc tca ggc aag cac tca gtg gcg ata ggt     5852
Asn Gly Ile Asp Ser Ser Ala Ser Gly Lys His Ser Val Ala Ile Gly
1700                1705                1710                1715 ttc cag gcc aag gca gat ggt gaa gcc gcc gtt gcc ata ggc aga caa     5900
Phe Gln Ala Lys Ala Asp Gly Glu Ala Ala Val Ala Ile Gly Arg Gln
            1720                1725                1730 acc caa gca ggc aac caa tcc atc gcc atc ggt gat aac gca caa gcc     5948
```

-continued

```
Thr Gln Ala Gly Asn Gln Ser Ile Ala Ile Gly Asp Asn Ala Gln Ala
              1735                1740                1745 acg ggc gat caa tcc atc gcc atc ggt aca ggc aat gtg gta gca ggt    5996
Thr Gly Asp Gln Ser Ile Ala Ile Gly Thr Gly Asn Val Val Ala Gly
1750                1755                1760 aag cac tct ggt gcc atc ggc gac cca agc act gtt aag gct gat aac    6044
Lys His Ser Gly Ala Ile Gly Asp Pro Ser Thr Val Lys Ala Asp Asn
       1765                1770                1775 agt tac agt gtg ggt aat aac aac cag ttt acc gat gcc act caa acc    6092
Ser Tyr Ser Val Gly Asn Asn Asn Gln Phe Thr Asp Ala Thr Gln Thr
1780                1785                1790                1795 gat gtc ttt ggt gtg ggc aat aac atc acc gtg acc gaa agt aac tcg    6140
Asp Val Phe Gly Val Gly Asn Asn Ile Thr Val Thr Glu Ser Asn Ser
            1800                1805                1810 gtt gcc tta ggt tca aac tct gcc atc agt gca ggc aca cac gca ggc    6188
Val Ala Leu Gly Ser Asn Ser Ala Ile Ser Ala Gly Thr His Ala Gly
       1815                1820                1825 aca caa gcc aaa aaa tct gac ggc aca gca ggt aca acc acc aca gca    6236
Thr Gln Ala Lys Lys Ser Asp Gly Thr Ala Gly Thr Thr Thr Thr Ala
1830                1835                1840 ggt gca acc ggt acg gtt aaa ggc ttt gct gga caa acg gcg gtt ggt    6284
Gly Ala Thr Gly Thr Val Lys Gly Phe Ala Gly Gln Thr Ala Val Gly
        1845                1850                1855 gcg gtc tcc gtg ggt gcc tca ggt gct gaa cgc cgt atc caa aat gtg    6332
Ala Val Ser Val Gly Ala Ser Gly Ala Glu Arg Arg Ile Gln Asn Val
1860                1865                1870                1875 gca gca ggt gag gtc agt gcc acc agc acc gat gcg gtc aat ggt agc    6380
Ala Ala Gly Glu Val Ser Ala Thr Ser Thr Asp Ala Val Asn Gly Ser
            1880                1885                1890 cag ttg tac aaa gcc acc caa agc att gcc aac gca acc aat gag ctt    6428
Gln Leu Tyr Lys Ala Thr Gln Ser Ile Ala Asn Ala Thr Asn Glu Leu
       1895                1900                1905 gac cat cgt atc cac caa aac gaa aat aag gcc aat gca ggg att tca    6476
Asp His Arg Ile His Gln Asn Glu Asn Lys Ala Asn Ala Gly Ile Ser
1910                1915                1920 tca gcg atg gcg atg gcg tcc atg cca caa gcc tac att cct ggc aga    6524
Ser Ala Met Ala Met Ala Ser Met Pro Gln Ala Tyr Ile Pro Gly Arg
        1925                1930                1935 tcc atg gtt acc ggg ggt att gcc acc cac aac ggt caa ggt gcg gtg    6572
Ser Met Val Thr Gly Gly Ile Ala Thr His Asn Gly Gln Gly Ala Val
1940                1945                1950                1955 gca gtg gga ctg tcg aag ctg tcg gat aat ggt caa tgg gta ttt aaa    6620
Ala Val Gly Leu Ser Lys Leu Ser Asp Asn Gly Gln Trp Val Phe Lys
            1960                1965                1970 atc aat ggt tca gcc gat acc caa ggc cat gta ggg gcg gca gtt ggt    6668
Ile Asn Gly Ser Ala Asp Thr Gln Gly His Val Gly Ala Ala Val Gly
       1975                1980                1985 gca ggt ttt cac ttt taagccataa atcgcaagat tttacttaaa aatcaatctc    6723
Ala Gly Phe His Phe
        1990 accatagttg tataaaacag catcagcatc agtcatatta ctgatgctga tgttttttat   6783 cacttaaacc attttaccgc tcaagtgatt ctctttcacc atgaccaaat cgccattgat   6843 cataggtaaa cttattgagt aaattttatc aatgtagttg ttagatatgg ttaaaattgt   6903 gccattgacc aaaaaatgac cgatttatcc cgaaaatttc tgattatgat ccgttgacct   6963 gcaggtcgac                                                         6973
```

<210> SEQ ID NO 2

<211> LENGTH: 5976
<212> TYPE: DNA
<213> ORGANISM: Moraxella catarrhalis

<400> SEQUENCE: 2

| | | | | | |
|---|---|---|---|---|---|
| gtgatcggtg | caacgctcag | tggcagtgct | tatgctcaaa | aaaagatac | caaacatatc | 60 |
| gcaattggtg | aacaaaacca | gccaagacgc | tcaggcactg | ccaaggcgga | cggtgatcga | 120 |
| gccattgcta | ttggtgaaaa | tgctaacgca | cagggcggtc | aagccatcgc | catcggtagt | 180 |
| agtaataaaa | ctgtcaatgg | aagcagtttg | gataagatag | gtaccgatgc | tacgggtcaa | 240 |
| gagtccatcg | ccatcggtgg | tgatgtaaag | gctagtggtg | atgcctcgat | tgccatcggt | 300 |
| agtgatgact | tacatttgct | tgatcagcat | ggtaatccta | aacatccgaa | aggtactctg | 360 |
| attaacgatc | ttattaacgg | ccatgcagta | ttaaaagaaa | tacgaagctc | aaaggataat | 420 |
| gatgtaaaat | atagacgcac | aaccgcaagc | ggacacgcca | gtactgcagt | gggagccatg | 480 |
| tcatatgcac | agggtcattt | tccaacgcc | tttggtacac | gggcaacagc | taaaagtgcc | 540 |
| tattccttgg | cagtgggtct | tgccgccaca | gccagggcc | aatctacaat | cgctattggt | 600 |
| tctgatgcaa | catctagctc | gttgggagcg | atagcccttg | gtgcaggtac | tcgtgctcag | 660 |
| ctacagggca | gtattgccct | aggtcaaggt | tctgttgtca | ctcagagtga | taataattct | 720 |
| agaccggcct | atacaccaaa | tacccaggca | ctagacccca | agtttcaagc | caccaataat | 780 |
| acgaaggcgg | gtccactttc | cattggtagt | aactctatca | aacgtaaaat | catcaatgtc | 840 |
| ggtgcaggtg | ttaataaaac | cgatgcggtc | aatgtggcac | agctagaagc | ggtggtgaag | 900 |
| tgggctaagg | agcgtagaat | tacttttcag | ggtgatgata | acagtactga | cgtaaaaata | 960 |
| ggtttggata | atactttaac | tattaaaggt | ggtgcagaga | ccaacgcatt | aaccgataat | 1020 |
| aatatcggtg | tggtaaaaga | ggctgataat | agtggtctga | agttaaaact | tgctaaaact | 1080 |
| ttaaacaatc | ttactgaggt | gaatacaact | acattaaatg | ccacaaccac | agttaaggta | 1140 |
| ggtagtagta | gtagtactac | agctgaatta | ttgagtgata | gtttaacctt | tacccagccc | 1200 |
| aatacaggca | gtcaaagcac | aagcaaaacc | gtctatggcg | ttaatggggt | gaagtttact | 1260 |
| aataatgcag | aaacaacagc | agcaatcggc | actactcgta | ttaccagaga | taaaattggc | 1320 |
| tttgctcgag | atggtgatgt | tgatgaaaaa | caagcaccat | atttggataa | aaaacaactt | 1380 |
| aaagtgggta | gtgttgcaat | taccatagac | aatggcattg | atgcaggtaa | taaaaagatc | 1440 |
| agtaatcttg | ccaaaggtag | cagtgctaac | gatgcggtta | ccatcgaaca | gctcaaagcc | 1500 |
| gccaagccta | ctttaaacgc | aggcgctggc | atcagtgtca | cacctactga | aatatcagtt | 1560 |
| gatgctaaga | gtggcaatgt | taccgcccca | acttacaaca | ttggcgtgaa | accaccgag | 1620 |
| cttaacagtg | atggcactag | tgataaattt | agtgttaagg | gtagtggtac | gaacaatagc | 1680 |
| ttagttaccg | ccgaacattt | ggcaagctat | ctaaatgaag | tcaatcgaac | ggctgacagt | 1740 |
| gctctacaaa | gctttaccgt | taaagaagaa | gacgatgatg | acgccaacgc | tatcaccgtg | 1800 |
| gctaaagata | cgacaaaaaa | tgccggcgca | gtcagcatct | taaaactcaa | aggtaaaaac | 1860 |
| ggtctaacgg | ttgctaccaa | aaaagatggt | acggttacct | ttgggcttag | ccaagatagc | 1920 |
| ggtctgacca | ttggcaaaag | caccctaaac | aacgatggct | tgactgttaa | agataccaac | 1980 |
| gaacaaatcc | aagtcggtgc | taatggcatt | aaatttacta | atgtgaatgg | tagtaatcca | 2040 |
| ggtactggca | ttgcaaatac | cgctcgcatt | accagagata | aaattggctt | tgctggttct | 2100 |
| gatggtgcag | ttgatacaaa | caaaccttat | cttgatcaag | acaagctaca | agttggcaat | 2160 |
| gttaagatta | ccaacactgg | cattaacgca | ggtggtaaag | ccatcacagg | gctgtcccca | 2220 |

```
acactgccta gcattgccga tcaaagtagc cgcaacatag aactgggcaa tacaatccaa    2280
gacaaagaca aatccaacgc tgccagcatt aatgatatat taaatacagg ctttaaccta    2340
aaaaataata acaaccccat tgactttgtc tccacttatg acattgttga ctttgccaat    2400
ggcaatgcca ccaccgccac agtaacccat gataccgcta acaaaaccag taaagtggta    2460
tatgatgtga atgtggatga tacaaccatt catctaacag gcactgatga caataaaaaa    2520
cttggcgtca aaaccaccaa actgaacaaa acaagtgcta atggtaatac agcaactaac    2580
tttaatgtta actctagtga tgaagatgcc cttgttaacg ccaaagacat cgccgaaaat    2640
ctaaacaccc tagccaagga aattcacacc accaaaggca cagcagacac cgccctacaa    2700
acctttaccg ttaaaaaggt agatgaaaat aataatgctg atgacgccaa cgccatcacc    2760
gtgggtcaaa agaacgcaaa taatcaagtc aacaccctaa cactcaaagg tgaaaacggt    2820
cttaatatta aaaccgacaa aaatggtacg gttacctttg gcattaacac cacaagcggt    2880
cttaaagccg gcaaaagcac cctaaacgac ggtggcttgt ctattaaaaa ccccactggt    2940
agcgaacaaa tccaagtcgg tgctgatggc gtgaagtttg ccaaggttaa taataatggt    3000
gttgtaggtg ctggcattga tggcacaact cgcattacca gagatgaaat tggctttact    3060
gggactaatg gctcacttga taaaagcaaa ccccacctaa gcaaagacgg cattaacgca    3120
ggtggtaaaa agattaccaa cattcaatca ggtgagattg cccaaaacag ccatgatgct    3180
gtgacaggcg gcaagattta tgatttaaaa accgaacttg aaaacaaaat cagcagtact    3240
gccaaaacag cacaaaactc attacacgaa ttctcagtag cagatgaaca aggtaataac    3300
tttacggtta gtaaccctta ctccagttat gacacctcaa agacctctga tgtcatcacc    3360
tttgcaggtg aaaacggcat taccaccaag gtaaataaag gtgtggtgcg tgtgggcatt    3420
gaccaaacca aaggcttaac cacgcctaag ctgaccgtgg gtaataataa tggcaaaggc    3480
attgtcattg acagccaaaa tggtcaaaat accatcacag gactaagcaa cactctagct    3540
aatgttacca atgataaagg tagcgtacgc accacagaac agggcaatat aatcaaagac    3600
gaagacaaaa cccgtgccgc cagcattgtt gatgtgctaa gcgcaggctt taacttgcaa    3660
ggcaatggtg aagcggttga ctttgtctcc acttatgaca ccgtcaactt tgccgatggc    3720
aatgccacca ccgctaaggt gacctatgat gacacaagca aaaccagtaa agtggtctat    3780
gatgtcaatg tggatgatac aaccattgaa gttaaagata aaaaacttgg cgtaaaaacc    3840
accacattga ccagtactgg cacaggtgct aataaatttg ccctaagcaa tcaagctact    3900
ggcgatgcgc ttgtcaaggc cagtgatatc gttgctcatc taaacacctt atctggcgac    3960
atccaaactg ccaaaggggc aagccaagcg aacaactcag caggctatgt ggatgctgat    4020
ggcaataagg tcatctatga cagtaccgat aacaagtact atcaagccaa aaatgatggc    4080
acagttgata aaaccaaaga agttgccaaa gacaaactgg tcgcccaagc ccaaaccccca    4140 gatggcacat tggctcaaat gaatgtcaaa tcagtcatta acaaagaaca agtaaatgat    4200
gccaataaaa agcaaggcat caatgaagac aacgcctttg ttaaaggact tgaaaaagcc    4260
gcttctgata caaaaccaa aaacgccgca gtaactgtgg gtgatttaaa tgccgttgcc    4320
caaacaccgc tgacctttgc aggggataca ggcacaacgg ctaaaaaact gggcgagact    4380
ttgaccatca aggtgggca aacagacacc aataagctaa ccgataataa catcggtgtg    4440
gtagcaggta ctgatggctt cactgtcaaa cttgccaaag acctaaccaa tcttaacagc    4500
gttaatgcag gtggcaccaa aattgatgac aaaggcgtgt cttttgtaga ctcaagcggt    4560
```

-continued

```
caagccaaag caaacacccc tgtgctaagt gccaatgggc tggacctggg tggcaaggtc    4620
atcagtaatg tgggcaaagg cacaaaagat accgacgctg ccaatgtaca acagttaaac    4680
gaagtacgca acttgttggg tcttggtaat gctggtaatg ataacgctga cggcaatcag    4740
gtaaacattg ccgacatcaa aaaagaccca aattcaggtt catcatctaa ccgcactgtc    4800
atcaaagcag gcacggtact tggcggtaaa ggtaataacg ataccgaaaa acttgccact    4860
ggtggtatac aagtgggcgt ggataaagac ggcaacgcta acggcgattt aagcaatgtt    4920
tgggtcaaaa cccaaaaaga tggcagcaaa aaagccctgc tcgccactta taacgccgca    4980
ggtcagacca actatttgac caacaacccc gcagaagcca ttgacagaat aaatgaacaa    5040
ggtatccgct tcttccatgt caacgatggc aatcaagagc tgtggtaca agggcgtaac    5100 ggcattgact caagtgcctc aggcaagcac tcagtggcga taggtttcca ggccaaggca    5160
gatggtgaag ccgccgttgc cataggcaga caaacccaag caggcaacca atccatcgcc    5220
atcggtgata acgcacaagc cacgggcgat caatccatcg ccatcggtac aggcaatgtg    5280
gtagcaggta agcactctgg tgccatcggc gacccaagca ctgttaaggc tgataacagt    5340
tacagtgtgg gtaataacaa ccagtttacc gatgccactc aaaccgatgt ctttggtgtg    5400
ggcaataaca tcaccgtgac cgaaagtaac tcggttgcct taggttcaaa ctctgccatc    5460
agtgcaggca cacgcagg cacacaagcc aaaaaatctg acggcacagc aggtacaacc    5520
accacagcag gtgcaaccgg tacgttaaa ggctttgctg acaaacggc ggttggtgcg    5580 gtctccgtgg gtgcctcagg tgctgaacgc cgtatccaaa atgtgcagc aggtgaggtc    5640 agtgccacca gcaccgatgc ggtcaatggt agccagttgt acaaagccac ccaaagcatt    5700
gccaacgcaa ccaatgagct tgaccatcgt atccaccaaa acgaaaataa ggccaatgca    5760
gggatttcat cagcgatggc gatggcgtcc atgccacaag cctacattcc tggcagatcc    5820
atggttaccg ggggtattgc cacccacaac ggtcaaggtg cggtggcagt gggactgtcg    5880
aagctgtcgg ataatggtca atgggtattt aaaatcaatg gttcagccga tacccaaggc    5940
catgtagggg cggcagttgg tgcaggtttt cactttt                             5976
```

<210> SEQ ID NO 3
<211> LENGTH: 1992
<212> TYPE: PRT
<213> ORGANISM: Moraxella catarrhalis

<400> SEQUENCE: 3

```
Met Ile Gly Ala Thr Leu Ser Gly Ser Ala Tyr Ala Gln Lys Lys Asp
 1               5                  10                  15

Thr Lys His Ile Ala Ile Gly Glu Gln Asn Gln Pro Arg Arg Ser Gly
            20                  25                  30

Thr Ala Lys Ala Asp Gly Asp Arg Ala Ile Ala Ile Gly Glu Asn Ala
        35                  40                  45

Asn Ala Gln Gly Gly Gln Ala Ile Ala Ile Gly Ser Ser Asn Lys Thr
    50                  55                  60

Val Asn Gly Ser Ser Leu Asp Lys Ile Gly Thr Asp Ala Thr Gly Gln
65                  70                  75                  80

Glu Ser Ile Ala Ile Gly Gly Asp Val Lys Ala Ser Gly Asp Ala Ser
                85                  90                  95

Ile Ala Ile Gly Ser Asp Asp Leu His Leu Leu Asp Gln His Gly Asn
            100                 105                 110

Pro Lys His Pro Lys Gly Thr Leu Ile Asn Asp Leu Ile Asn Gly His
        115                 120                 125
```

-continued

```
Ala Val Leu Lys Glu Ile Arg Ser Ser Lys Asp Asn Asp Val Lys Tyr
    130                 135                 140
Arg Arg Thr Thr Ala Ser Gly His Ala Ser Thr Ala Val Gly Ala Met
145                 150                 155                 160
Ser Tyr Ala Gln Gly His Phe Ser Asn Ala Phe Gly Thr Arg Ala Thr
                165                 170                 175
Ala Lys Ser Ala Tyr Ser Leu Ala Val Gly Leu Ala Ala Thr Ala Glu
                180                 185                 190
Gly Gln Ser Thr Ile Ala Ile Gly Ser Asp Ala Thr Ser Ser Ser Leu
                195                 200                 205
Gly Ala Ile Ala Leu Gly Ala Gly Thr Arg Ala Gln Leu Gln Gly Ser
    210                 215                 220
Ile Ala Leu Gly Gln Gly Ser Val Val Thr Gln Ser Asp Asn Asn Ser
225                 230                 235                 240
Arg Pro Ala Tyr Thr Pro Asn Thr Gln Ala Leu Asp Pro Lys Phe Gln
                245                 250                 255
Ala Thr Asn Asn Thr Lys Ala Gly Pro Leu Ser Ile Gly Ser Asn Ser
                260                 265                 270
Ile Lys Arg Lys Ile Ile Asn Val Gly Ala Gly Val Asn Lys Thr Asp
    275                 280                 285
Ala Val Asn Val Ala Gln Leu Glu Ala Val Val Lys Trp Ala Lys Glu
    290                 295                 300
Arg Arg Ile Thr Phe Gln Gly Asp Asp Asn Ser Thr Asp Val Lys Ile
305                 310                 315                 320
Gly Leu Asp Asn Thr Leu Thr Ile Lys Gly Gly Ala Glu Thr Asn Ala
                325                 330                 335
Leu Thr Asp Asn Asn Ile Gly Val Val Lys Glu Ala Asp Asn Ser Gly
                340                 345                 350
Leu Lys Val Lys Leu Ala Lys Thr Leu Asn Asn Leu Thr Glu Val Asn
                355                 360                 365
Thr Thr Thr Leu Asn Ala Thr Thr Thr Val Lys Val Gly Ser Ser Ser
    370                 375                 380
Ser Thr Thr Ala Glu Leu Leu Ser Asp Ser Leu Thr Phe Thr Gln Pro
385                 390                 395                 400
Asn Thr Gly Ser Gln Ser Thr Ser Lys Thr Val Tyr Gly Val Asn Gly
                405                 410                 415
Val Lys Phe Thr Asn Asn Ala Glu Thr Thr Ala Ala Ile Gly Thr Thr
                420                 425                 430
Arg Ile Thr Arg Asp Lys Ile Gly Phe Ala Arg Asp Gly Asp Val Asp
    435                 440                 445
Glu Lys Gln Ala Pro Tyr Leu Asp Lys Lys Gln Leu Lys Val Gly Ser
    450                 455                 460
Val Ala Ile Thr Ile Asp Asn Gly Ile Asp Ala Gly Asn Lys Lys Ile
465                 470                 475                 480
Ser Asn Leu Ala Lys Gly Ser Ser Ala Asn Asp Ala Val Thr Ile Glu
                485                 490                 495
Gln Leu Lys Ala Ala Lys Pro Thr Leu Asn Ala Gly Ala Gly Ile Ser
                500                 505                 510
Val Thr Pro Thr Glu Ile Ser Val Asp Ala Lys Ser Gly Asn Val Thr
    515                 520                 525
Ala Pro Thr Tyr Asn Ile Gly Val Lys Thr Thr Glu Leu Asn Ser Asp
    530                 535                 540
```

-continued

```
Gly Thr Ser Asp Lys Phe Ser Val Lys Gly Gly Thr Asn Asn Ser
545                 550                 555                 560

Leu Val Thr Ala Glu His Leu Ala Ser Tyr Leu Asn Glu Val Asn Arg
            565                 570                 575

Thr Ala Asp Ser Ala Leu Gln Ser Phe Thr Val Lys Glu Glu Asp Asp
        580                 585                 590

Asp Asp Ala Asn Ala Ile Thr Val Ala Lys Asp Thr Thr Lys Asn Ala
        595                 600                 605

Gly Ala Val Ser Ile Leu Lys Leu Lys Gly Lys Asn Gly Leu Thr Val
    610                 615                 620

Ala Thr Lys Lys Asp Gly Thr Val Thr Phe Gly Leu Ser Gln Asp Ser
625                 630                 635                 640

Gly Leu Thr Ile Gly Lys Ser Thr Leu Asn Asn Asp Gly Leu Thr Val
            645                 650                 655

Lys Asp Thr Asn Glu Gln Ile Gln Val Gly Ala Asn Gly Ile Lys Phe
        660                 665                 670

Thr Asn Val Asn Gly Ser Asn Pro Gly Thr Gly Ile Ala Asn Thr Ala
        675                 680                 685

Arg Ile Thr Arg Asp Lys Ile Gly Phe Ala Gly Ser Asp Gly Ala Val
    690                 695                 700

Asp Thr Asn Lys Pro Tyr Leu Asp Gln Asp Lys Leu Gln Val Gly Asn
705                 710                 715                 720

Val Lys Ile Thr Asn Thr Gly Ile Asn Ala Gly Gly Lys Ala Ile Thr
            725                 730                 735

Gly Leu Ser Pro Thr Leu Pro Ser Ile Ala Asp Gln Ser Ser Arg Asn
        740                 745                 750

Ile Glu Leu Gly Asn Thr Ile Gln Asp Lys Asp Lys Ser Asn Ala Ala
        755                 760                 765

Ser Ile Asn Asp Ile Leu Asn Thr Gly Phe Asn Leu Lys Asn Asn Asn
    770                 775                 780

Asn Pro Ile Asp Phe Val Ser Thr Tyr Asp Ile Val Asp Phe Ala Asn
785                 790                 795                 800

Gly Asn Ala Thr Thr Ala Thr Val Thr His Asp Thr Ala Asn Lys Thr
            805                 810                 815

Ser Lys Val Val Tyr Asp Val Asn Val Asp Asp Thr Thr Ile His Leu
        820                 825                 830

Thr Gly Thr Asp Asp Asn Lys Lys Leu Gly Val Lys Thr Thr Lys Leu
        835                 840                 845

Asn Lys Thr Ser Ala Asn Gly Asn Thr Ala Thr Asn Phe Asn Val Asn
850                 855                 860

Ser Ser Asp Glu Asp Ala Leu Val Asn Ala Lys Asp Ile Ala Glu Asn
865                 870                 875                 880

Leu Asn Thr Leu Ala Lys Glu Ile His Thr Thr Lys Gly Thr Ala Asp
            885                 890                 895

Thr Ala Leu Gln Thr Phe Thr Val Lys Lys Val Asp Glu Asn Asn Asn
        900                 905                 910

Ala Asp Asp Ala Asn Ala Ile Thr Val Gly Gln Lys Asn Ala Asn Asn
        915                 920                 925

Gln Val Asn Thr Leu Thr Leu Lys Gly Glu Asn Gly Leu Asn Ile Lys
    930                 935                 940

Thr Asp Lys Asn Gly Thr Val Thr Phe Gly Ile Asn Thr Thr Ser Gly
945                 950                 955                 960

Leu Lys Ala Gly Lys Ser Thr Leu Asn Asp Gly Gly Leu Ser Ile Lys
```

-continued

```
                965                 970                 975
Asn Pro Thr Gly Ser Glu Gln Ile Gln Val Gly Ala Asp Gly Val Lys
            980                 985                 990
Phe Ala Lys Val Asn Asn Gly Val Val Gly Ala Gly Ile Asp Gly
            995                1000                1005
Thr Thr Arg Ile Thr Arg Asp Glu Ile Gly Phe Thr Gly Thr Asn Gly
    1010                1015                1020
Ser Leu Asp Lys Ser Lys Pro His Leu Ser Lys Asp Gly Ile Asn Ala
1025                1030                1035                1040
Gly Gly Lys Lys Ile Thr Asn Ile Gln Ser Gly Glu Ile Ala Gln Asn
                1045                1050                1055
Ser His Asp Ala Val Thr Gly Gly Lys Ile Tyr Asp Leu Lys Thr Glu
            1060                1065                1070
Leu Glu Asn Lys Ile Ser Ser Thr Ala Lys Thr Ala Gln Asn Ser Leu
        1075                1080                1085
His Glu Phe Ser Val Ala Asp Glu Gln Gly Asn Asn Phe Thr Val Ser
        1090                1095                1100
Asn Pro Tyr Ser Ser Tyr Asp Thr Ser Lys Thr Ser Asp Val Ile Thr
1105                1110                1115                1120
Phe Ala Gly Glu Asn Gly Ile Thr Thr Lys Val Asn Lys Gly Val Val
                1125                1130                1135
Arg Val Gly Ile Asp Gln Thr Lys Gly Leu Thr Thr Pro Lys Leu Thr
            1140                1145                1150
Val Gly Asn Asn Gly Lys Gly Ile Val Ile Asp Ser Gln Asn Gly
        1155                1160                1165
Gln Asn Thr Ile Thr Gly Leu Ser Asn Thr Leu Ala Asn Val Thr Asn
    1170                1175                1180
Asp Lys Gly Ser Val Arg Thr Thr Glu Gln Gly Asn Ile Ile Lys Asp
1185                1190                1195                1200
Glu Asp Lys Thr Arg Ala Ala Ser Ile Val Asp Val Leu Ser Ala Gly
                1205                1210                1215
Phe Asn Leu Gln Gly Asn Gly Glu Ala Val Asp Phe Val Ser Thr Tyr
            1220                1225                1230
Asp Thr Val Asn Phe Ala Asp Gly Asn Ala Thr Thr Ala Lys Val Thr
        1235                1240                1245
Tyr Asp Asp Thr Ser Lys Thr Ser Lys Val Val Tyr Asp Val Asn Val
    1250                1255                1260
Asp Asp Thr Thr Ile Glu Val Lys Asp Lys Lys Leu Gly Val Lys Thr
1265                1270                1275                1280
Thr Thr Leu Thr Ser Thr Gly Thr Gly Ala Asn Lys Phe Ala Leu Ser
                1285                1290                1295
Asn Gln Ala Thr Gly Asp Ala Leu Val Lys Ala Ser Asp Ile Val Ala
            1300                1305                1310
His Leu Asn Thr Leu Ser Gly Asp Ile Gln Thr Ala Lys Gly Ala Ser
        1315                1320                1325
Gln Ala Asn Asn Ser Ala Gly Tyr Val Asp Ala Asp Gly Asn Lys Val
    1330                1335                1340
Ile Tyr Asp Ser Thr Asp Asn Lys Tyr Tyr Gln Ala Lys Asn Asp Gly
1345                1350                1355                1360
Thr Val Asp Lys Thr Lys Glu Val Ala Lys Asp Lys Leu Val Ala Gln
                1365                1370                1375
Ala Gln Thr Pro Asp Gly Thr Leu Ala Gln Met Asn Val Lys Ser Val
            1380                1385                1390
```

-continued

```
Ile Asn Lys Glu Gln Val Asn Asp Ala Asn Lys Lys Gln Gly Ile Asn
        1395                1400                1405
Glu Asp Asn Ala Phe Val Lys Gly Leu Glu Lys Ala Ala Ser Asp Asn
    1410                1415                1420
Lys Thr Lys Asn Ala Ala Val Thr Val Gly Asp Leu Asn Ala Val Ala
1425                1430                1435                1440
Gln Thr Pro Leu Thr Phe Ala Gly Asp Thr Gly Thr Ala Lys Lys
            1445                1450                1455
Leu Gly Glu Thr Leu Thr Ile Lys Gly Gly Gln Thr Asp Thr Asn Lys
            1460                1465                1470
Leu Thr Asp Asn Asn Ile Gly Val Val Ala Gly Thr Asp Gly Phe Thr
    1475                1480                1485
Val Lys Leu Ala Lys Asp Leu Thr Asn Leu Asn Ser Val Asn Ala Gly
    1490                1495                1500
Gly Thr Lys Ile Asp Asp Lys Gly Val Ser Phe Val Asp Ser Ser Gly
1505                1510                1515                1520
Gln Ala Lys Ala Asn Thr Pro Val Leu Ser Ala Asn Gly Leu Asp Leu
        1525                1530                1535
Gly Gly Lys Val Ile Ser Asn Val Gly Lys Gly Thr Lys Asp Thr Asp
        1540                1545                1550
Ala Ala Asn Val Gln Gln Leu Asn Glu Val Arg Asn Leu Leu Gly Leu
        1555                1560                1565
Gly Asn Ala Gly Asn Asp Asn Ala Asp Gly Asn Gln Val Asn Ile Ala
    1570                1575                1580
Asp Ile Lys Lys Asp Pro Asn Ser Gly Ser Ser Ser Asn Arg Thr Val
1585                1590                1595                1600
Ile Lys Ala Gly Thr Val Leu Gly Gly Lys Gly Asn Asn Asp Thr Glu
            1605                1610                1615
Lys Leu Ala Thr Gly Gly Ile Gln Val Gly Val Asp Lys Asp Gly Asn
            1620                1625                1630
Ala Asn Gly Asp Leu Ser Asn Val Trp Val Lys Thr Gln Lys Asp Gly
        1635                1640                1645
Ser Lys Lys Ala Leu Leu Ala Thr Tyr Asn Ala Ala Gly Gln Thr Asn
    1650                1655                1660
Tyr Leu Thr Asn Asn Pro Ala Glu Ala Ile Asp Arg Ile Asn Glu Gln
1665                1670                1675                1680
Gly Ile Arg Phe Phe His Val Asn Asp Gly Asn Gln Glu Pro Val Val
            1685                1690                1695
Gln Gly Arg Asn Gly Ile Asp Ser Ser Ala Ser Gly Lys His Ser Val
        1700                1705                1710
Ala Ile Gly Phe Gln Ala Lys Ala Asp Gly Glu Ala Ala Val Ala Ile
            1715                1720                1725
Gly Arg Gln Thr Gln Ala Gly Asn Gln Ser Ile Ala Ile Gly Asp Asn
        1730                1735                1740
Ala Gln Ala Thr Gly Asp Gln Ser Ile Ala Ile Gly Thr Gly Asn Val
1745                1750                1755                1760
Val Ala Gly Lys His Ser Gly Ala Ile Gly Asp Pro Ser Thr Val Lys
            1765                1770                1775
Ala Asp Asn Ser Tyr Ser Val Gly Asn Asn Asn Gln Phe Thr Asp Ala
        1780                1785                1790
Thr Gln Thr Asp Val Phe Gly Val Gly Asn Asn Ile Thr Val Thr Glu
        1795                1800                1805
```

-continued

```
Ser Asn Ser Val Ala Leu Gly Ser Asn Ser Ala Ile Ser Ala Gly Thr
    1810                1815                1820

His Ala Gly Thr Gln Ala Lys Lys Ser Asp Gly Thr Ala Gly Thr Thr
1825                1830                1835                1840

Thr Thr Ala Gly Ala Thr Gly Thr Val Lys Gly Phe Ala Gly Gln Thr
        1845                1850                1855

Ala Val Gly Ala Val Ser Val Gly Ala Ser Gly Ala Glu Arg Arg Ile
        1860                1865                1870

Gln Asn Val Ala Ala Gly Glu Val Ser Ala Thr Ser Thr Asp Ala Val
    1875                1880                1885

Asn Gly Ser Gln Leu Tyr Lys Ala Thr Gln Ser Ile Ala Asn Ala Thr
    1890                1895                1900

Asn Glu Leu Asp His Arg Ile His Gln Asn Glu Asn Lys Ala Asn Ala
1905                1910                1915                1920

Gly Ile Ser Ser Ala Met Ala Met Ala Ser Met Pro Gln Ala Tyr Ile
            1925                1930                1935

Pro Gly Arg Ser Met Val Thr Gly Gly Ile Ala Thr His Asn Gly Gln
            1940                1945                1950

Gly Ala Val Ala Val Gly Leu Ser Lys Leu Ser Asp Asn Gly Gln Trp
        1955                1960                1965

Val Phe Lys Ile Asn Gly Ser Ala Asp Thr Gln Gly His Val Gly Ala
    1970                1975                1980

Ala Val Gly Ala Gly Phe His Phe
1985                1990

<210> SEQ ID NO 4
<211> LENGTH: 1833
<212> TYPE: PRT
<213> ORGANISM: Moraxella catarrhalis

<400> SEQUENCE: 4

Met Ser Tyr Ala Gln Gly His Phe Ser Asn Ala Phe Gly Thr Arg Ala
  1               5                  10                  15

Thr Ala Lys Ser Ala Tyr Ser Leu Ala Val Gly Leu Ala Ala Thr Ala
             20                  25                  30

Glu Gly Gln Ser Thr Ile Ala Ile Gly Ser Asp Ala Thr Ser Ser Ser
         35                  40                  45

Leu Gly Ala Ile Ala Leu Gly Ala Gly Thr Arg Ala Gln Leu Gln Gly
     50                  55                  60

Ser Ile Ala Leu Gly Gln Gly Ser Val Val Thr Gln Ser Asp Asn Asn
 65                  70                  75                  80

Ser Arg Pro Ala Tyr Thr Pro Asn Thr Gln Ala Leu Asp Pro Lys Phe
                 85                  90                  95

Gln Ala Thr Asn Asn Thr Lys Ala Gly Pro Leu Ser Ile Gly Ser Asn
            100                 105                 110

Ser Ile Lys Arg Lys Ile Ile Asn Val Gly Ala Gly Val Asn Lys Thr
        115                 120                 125

Asp Ala Val Asn Val Ala Gln Leu Glu Ala Val Lys Trp Ala Lys
    130                 135                 140

Glu Arg Arg Ile Thr Phe Gln Gly Asp Asp Asn Ser Thr Asp Val Lys
145                 150                 155                 160

Ile Gly Leu Asp Asn Thr Leu Thr Ile Lys Gly Gly Ala Glu Thr Asn
                165                 170                 175

Ala Leu Thr Asp Asn Asn Ile Gly Val Val Lys Glu Ala Asp Asn Ser
            180                 185                 190
```

-continued

Gly Leu Lys Val Lys Leu Ala Lys Thr Leu Asn Asn Leu Thr Glu Val
            195                 200                 205

Asn Thr Thr Thr Leu Asn Ala Thr Thr Val Lys Val Gly Ser Ser
210                 215                 220

Ser Ser Thr Thr Ala Glu Leu Leu Ser Asp Ser Leu Thr Phe Thr Gln
225                 230                 235                 240

Pro Asn Thr Gly Ser Gln Ser Thr Ser Lys Thr Val Tyr Gly Val Asn
                245                 250                 255

Gly Val Lys Phe Thr Asn Asn Ala Glu Thr Thr Ala Ala Ile Gly Thr
            260                 265                 270

Thr Arg Ile Thr Arg Asp Lys Ile Gly Phe Ala Arg Asp Gly Asp Val
            275                 280                 285

Asp Glu Lys Gln Ala Pro Tyr Leu Asp Lys Lys Gln Leu Lys Val Gly
290                 295                 300

Ser Val Ala Ile Thr Ile Asp Asn Gly Ile Asp Ala Gly Asn Lys Lys
305                 310                 315                 320

Ile Ser Asn Leu Ala Lys Gly Ser Ser Ala Asn Asp Ala Val Thr Ile
                325                 330                 335

Glu Gln Leu Lys Ala Ala Lys Pro Thr Leu Asn Ala Gly Ala Gly Ile
            340                 345                 350

Ser Val Thr Pro Thr Glu Ile Ser Val Asp Ala Lys Ser Gly Asn Val
            355                 360                 365

Thr Ala Pro Thr Tyr Asn Ile Gly Val Lys Thr Thr Glu Leu Asn Ser
            370                 375                 380

Asp Gly Thr Ser Asp Lys Phe Ser Val Lys Gly Ser Gly Thr Asn Asn
385                 390                 395                 400

Ser Leu Val Thr Ala Glu His Leu Ala Ser Tyr Leu Asn Glu Val Asn
                405                 410                 415

Arg Thr Ala Asp Ser Ala Leu Gln Ser Phe Thr Val Lys Glu Glu Asp
            420                 425                 430

Asp Asp Asp Ala Asn Ala Ile Thr Val Ala Lys Asp Thr Thr Lys Asn
435                 440                 445

Ala Gly Ala Val Ser Ile Leu Lys Leu Lys Gly Lys Asn Gly Leu Thr
450                 455                 460

Val Ala Thr Lys Lys Asp Gly Thr Val Thr Phe Gly Leu Ser Gln Asp
465                 470                 475                 480

Ser Gly Leu Thr Ile Gly Lys Ser Thr Leu Asn Asn Asp Gly Leu Thr
                485                 490                 495

Val Lys Asp Thr Asn Glu Gln Ile Gln Val Gly Ala Asn Gly Ile Lys
            500                 505                 510

Phe Thr Asn Val Asn Gly Ser Asn Pro Gly Thr Gly Ile Ala Asn Thr
            515                 520                 525

Ala Arg Ile Thr Arg Asp Lys Ile Gly Phe Ala Gly Ser Asp Gly Ala
            530                 535                 540

Val Asp Thr Asn Lys Pro Tyr Leu Asp Gln Asp Lys Leu Gln Val Gly
545                 550                 555                 560

Asn Val Lys Ile Thr Asn Thr Gly Ile Asn Ala Gly Gly Lys Ala Ile
                565                 570                 575

Thr Gly Leu Ser Pro Thr Leu Pro Ser Ile Ala Asp Gln Ser Ser Arg
            580                 585                 590

Asn Ile Glu Leu Gly Asn Thr Ile Gln Asp Lys Asp Lys Ser Asn Ala
            595                 600                 605

-continued

```
Ala Ser Ile Asn Asp Ile Leu Asn Thr Gly Phe Asn Leu Lys Asn Asn
    610                 615                 620

Asn Asn Pro Ile Asp Phe Val Ser Thr Tyr Asp Ile Val Asp Phe Ala
625                 630                 635                 640

Asn Gly Asn Ala Thr Thr Ala Thr Val Thr His Asp Thr Ala Asn Lys
                645                 650                 655

Thr Ser Lys Val Val Tyr Asp Val Asn Val Asp Asp Thr Ile His
            660                 665                 670

Leu Thr Gly Thr Asp Asp Asn Lys Lys Leu Gly Val Lys Thr Thr Lys
        675                 680                 685

Leu Asn Lys Thr Ser Ala Asn Gly Asn Thr Ala Thr Asn Phe Asn Val
    690                 695                 700

Asn Ser Ser Asp Glu Asp Ala Leu Val Asn Ala Lys Asp Ile Ala Glu
705                 710                 715                 720

Asn Leu Asn Thr Leu Ala Lys Glu Ile His Thr Thr Lys Gly Thr Ala
                725                 730                 735

Asp Thr Ala Leu Gln Thr Phe Thr Val Lys Val Asp Glu Asn Asn
            740                 745                 750

Asn Ala Asp Asp Ala Asn Ala Ile Thr Val Gly Gln Lys Asn Ala Asn
        755                 760                 765

Asn Gln Val Asn Thr Leu Thr Leu Lys Gly Glu Asn Gly Leu Asn Ile
    770                 775                 780

Lys Thr Asp Lys Asn Gly Thr Val Thr Phe Gly Ile Asn Thr Thr Ser
785                 790                 795                 800

Gly Leu Lys Ala Gly Lys Ser Thr Leu Asn Asp Gly Gly Leu Ser Ile
                805                 810                 815

Lys Asn Pro Thr Gly Ser Glu Gln Ile Gln Val Gly Ala Asp Gly Val
            820                 825                 830

Lys Phe Ala Lys Val Asn Asn Asn Gly Val Val Gly Ala Gly Ile Asp
        835                 840                 845

Gly Thr Thr Arg Ile Thr Arg Asp Glu Ile Gly Phe Thr Gly Thr Asn
    850                 855                 860

Gly Ser Leu Asp Lys Ser Lys Pro His Leu Ser Lys Asp Gly Ile Asn
865                 870                 875                 880

Ala Gly Gly Lys Lys Ile Thr Asn Ile Gln Ser Gly Glu Ile Ala Gln
                885                 890                 895

Asn Ser His Asp Ala Val Thr Gly Gly Lys Ile Tyr Asp Leu Lys Thr
            900                 905                 910

Glu Leu Glu Asn Lys Ile Ser Ser Thr Ala Lys Thr Ala Gln Asn Ser
        915                 920                 925

Leu His Glu Phe Ser Val Ala Asp Glu Gln Gly Asn Asn Phe Thr Val
    930                 935                 940

Ser Asn Pro Tyr Ser Ser Tyr Asp Thr Ser Lys Thr Ser Asp Val Ile
945                 950                 955                 960

Thr Phe Ala Gly Glu Asn Gly Ile Thr Thr Lys Val Asn Lys Gly Val
                965                 970                 975

Val Arg Val Gly Ile Asp Gln Thr Lys Gly Leu Thr Thr Pro Lys Leu
            980                 985                 990

Thr Val Gly Asn Asn Gly Lys Gly Ile Val Ile Asp Ser Gln Asn
        995                 1000                1005

Gly Gln Asn Thr Ile Thr Gly Leu Ser Asn Thr Leu Ala Asn Val Thr
    1010                1015                1020

Asn Asp Lys Gly Ser Val Arg Thr Thr Glu Gln Gly Asn Ile Ile Lys
```

```
                    1025                1030                1035                1040

Asp Glu Asp Lys Thr Arg Ala Ala Ser Ile Val Asp Val Leu Ser Ala
                1045                1050                1055

Gly Phe Asn Leu Gln Gly Asn Gly Glu Ala Val Asp Phe Val Ser Thr
            1060                1065                1070

Tyr Asp Thr Val Asn Phe Ala Asp Gly Asn Ala Thr Thr Ala Lys Val
        1075                1080                1085

Thr Tyr Asp Asp Thr Ser Lys Thr Ser Lys Val Val Tyr Asp Val Asn
     1090                1095                1100

Val Asp Asp Thr Thr Ile Glu Val Lys Asp Lys Lys Leu Gly Val Lys
1105                1110                1115                1120

Thr Thr Thr Leu Thr Ser Thr Gly Thr Gly Ala Asn Lys Phe Ala Leu
                1125                1130                1135

Ser Asn Gln Ala Thr Gly Asp Ala Leu Val Lys Ala Ser Asp Ile Val
            1140                1145                1150

Ala His Leu Asn Thr Leu Ser Gly Asp Ile Gln Thr Ala Lys Gly Ala
        1155                1160                1165

Ser Gln Ala Asn Asn Ser Ala Gly Tyr Val Asp Ala Asp Gly Asn Lys
     1170                1175                1180

Val Ile Tyr Asp Ser Thr Asp Asn Lys Tyr Tyr Gln Ala Lys Asn Asp
1185                1190                1195                1200

Gly Thr Val Asp Lys Thr Lys Glu Val Ala Lys Asp Lys Leu Val Ala
                1205                1210                1215

Gln Ala Gln Thr Pro Asp Gly Thr Leu Ala Gln Met Asn Val Lys Ser
            1220                1225                1230

Val Ile Asn Lys Glu Gln Val Asn Asp Ala Asn Lys Lys Gln Gly Ile
        1235                1240                1245

Asn Glu Asp Asn Ala Phe Val Lys Gly Leu Glu Lys Ala Ala Ser Asp
     1250                1255                1260

Asn Lys Thr Lys Asn Ala Ala Val Thr Val Gly Asp Leu Asn Ala Val
1265                1270                1275                1280

Ala Gln Thr Pro Leu Thr Phe Ala Gly Asp Thr Gly Thr Thr Ala Lys
                1285                1290                1295

Lys Leu Gly Glu Thr Leu Thr Ile Lys Gly Gly Gln Thr Asp Thr Asn
            1300                1305                1310

Lys Leu Thr Asp Asn Asn Ile Gly Val Val Ala Gly Thr Asp Gly Phe
        1315                1320                1325

Thr Val Lys Leu Ala Lys Asp Leu Thr Asn Leu Asn Ser Val Asn Ala
     1330                1335                1340

Gly Gly Thr Lys Ile Asp Asp Lys Gly Val Ser Phe Val Asp Ser Ser
1345                1350                1355                1360

Gly Gln Ala Lys Ala Asn Thr Pro Val Leu Ser Ala Asn Gly Leu Asp
            1365                1370                1375

Leu Gly Gly Lys Val Ile Ser Asn Val Gly Lys Gly Thr Lys Asp Thr
        1380                1385                1390

Asp Ala Ala Asn Val Gln Gln Leu Asn Glu Val Arg Asn Leu Leu Gly
     1395                1400                1405

Leu Gly Asn Ala Gly Asn Asp Asn Ala Asp Gly Asn Gln Val Asn Ile
    1410                1415                1420

Ala Asp Ile Lys Lys Asp Pro Asn Ser Gly Ser Ser Ser Asn Arg Thr
1425                1430                1435                1440

Val Ile Lys Ala Gly Thr Val Leu Gly Gly Lys Gly Asn Asn Asp Thr
                1445                1450                1455
```

-continued

```
Glu Lys Leu Ala Thr Gly Gly Ile Gln Val Gly Val Asp Lys Asp Gly
        1460                1465                1470
Asn Ala Asn Gly Asp Leu Ser Asn Val Trp Val Lys Thr Gln Lys Asp
    1475                1480                1485
Gly Ser Lys Lys Ala Leu Leu Ala Thr Tyr Asn Ala Ala Gly Gln Thr
1490                1495                1500
Asn Tyr Leu Thr Asn Asn Pro Ala Glu Ala Ile Asp Arg Ile Asn Glu
1505                1510                1515                1520
Gln Gly Ile Arg Phe Phe His Val Asn Asp Gly Asn Gln Glu Pro Val
            1525                1530                1535
Val Gln Gly Arg Asn Gly Ile Asp Ser Ser Ala Ser Gly Lys His Ser
        1540                1545                1550
Val Ala Ile Gly Phe Gln Ala Lys Ala Asp Gly Glu Ala Ala Val Ala
    1555                1560                1565
Ile Gly Arg Gln Thr Gln Ala Gly Asn Gln Ser Ile Ala Ile Gly Asp
1570                1575                1580
Asn Ala Gln Ala Thr Gly Asp Gln Ser Ile Ala Ile Gly Thr Gly Asn
1585                1590                1595                1600
Val Val Ala Gly Lys His Ser Gly Ala Ile Gly Asp Pro Ser Thr Val
            1605                1610                1615
Lys Ala Asp Asn Ser Tyr Ser Val Gly Asn Asn Gln Phe Thr Asp
        1620                1625                1630
Ala Thr Gln Thr Asp Val Phe Gly Val Gly Asn Ile Thr Val Thr
    1635                1640                1645
Glu Ser Asn Ser Val Ala Leu Gly Ser Asn Ser Ala Ile Ser Ala Gly
1650                1655                1660
Thr His Ala Gly Thr Gln Ala Lys Lys Ser Asp Gly Thr Ala Gly Thr
1665                1670                1675                1680
Thr Thr Thr Ala Gly Ala Thr Gly Thr Val Lys Gly Phe Ala Gly Gln
            1685                1690                1695
Thr Ala Val Gly Ala Val Ser Val Gly Ala Ser Gly Ala Glu Arg Arg
        1700                1705                1710
Ile Gln Asn Val Ala Ala Gly Glu Val Ser Ala Thr Ser Thr Asp Ala
    1715                1720                1725
Val Asn Gly Ser Gln Leu Tyr Lys Ala Thr Gln Ser Ile Ala Asn Ala
1730                1735                1740
Thr Asn Glu Leu Asp His Arg Ile His Gln Asn Glu Asn Lys Ala Asn
1745                1750                1755                1760
Ala Gly Ile Ser Ser Ala Met Ala Met Ala Ser Met Pro Gln Ala Tyr
            1765                1770                1775
Ile Pro Gly Arg Ser Met Val Thr Gly Gly Ile Ala Thr His Asn Gly
        1780                1785                1790
Gln Gly Ala Val Ala Val Gly Leu Ser Lys Leu Ser Asp Asn Gly Gln
    1795                1800                1805
Trp Val Phe Lys Ile Asn Gly Ser Ala Asp Thr Gln Gly His Val Gly
1810                1815                1820
Ala Ala Val Gly Ala Gly Phe His Phe
1825                1830

<210> SEQ ID NO 5
<211> LENGTH: 20
<212> TYPE: PRT
<213> ORGANISM: Moraxella catarrhalis
<220> FEATURE:
```

```
<221> NAME/KEY: UNSURE
<222> LOCATION: (17)

<400> SEQUENCE: 5

Asn Val Lys Ser Val Ile Asn Lys Glu Gln Val Asn Asp Ala Asn Lys
 1               5                  10                  15

Xaa Gln Gly Ile
            20

<210> SEQ ID NO 6
<211> LENGTH: 16
<212> TYPE: PRT
<213> ORGANISM: Moraxella catarrhalis

<400> SEQUENCE: 6

Asn Val Lys Ser Val Ile Asn Lys Glu Gln Val Asn Asp Ala Asn Lys
 1               5                  10                  15

<210> SEQ ID NO 7
<211> LENGTH: 60
<212> TYPE: DNA
<213> ORGANISM: Moraxella catarrhalis

<400> SEQUENCE: 7
aatgtcaaat cagtcattaa caaagaacaa gtaaatgatg ccaataaaaa gcaaggcatc     60

<210> SEQ ID NO 8
<211> LENGTH: 20
<212> TYPE: PRT
<213> ORGANISM: Moraxella catarrhalis

<400> SEQUENCE: 8

Asn Val Lys Ser Val Ile Asn Lys Glu Gln Val Asn Asp Ala Asn Lys
 1               5                  10                  15

Lys Gln Gly Ile
            20

<210> SEQ ID NO 9
<211> LENGTH: 30
<212> TYPE: PRT
<213> ORGANISM: Moraxella catarrhalis

<400> SEQUENCE: 9

Met Ile Gly Ala Thr Leu Ser Gly Ser Ala Tyr Ala Gln Lys Lys Asp
 1               5                  10                  15

Thr Lys His Ile Ala Ile Gly Glu Gln Asn Gln Pro Arg Arg
            20                  25                  30

<210> SEQ ID NO 10
<211> LENGTH: 30
<212> TYPE: PRT
<213> ORGANISM: Moraxella catarrhalis

<400> SEQUENCE: 10

Ser Gly Thr Ala Lys Ala Asp Gly Asp Arg Ala Ile Ala Ile Gly Glu
 1               5                  10                  15

Asn Ala Asn Ala Gln Gly Gly Gln Ala Ile Ala Ile Gly Ser
            20                  25                  30
```